(12) United States Patent
Colombini

(10) Patent No.: US 7,897,401 B2
(45) Date of Patent: Mar. 1, 2011

(54) CONTROL OF APOPTOSIS BY CONTROLLING THE PROPENSITY OF CERAMIDE CHANNEL FORMATION

(75) Inventor: Marco Colombini, Sandy Spring, MD (US)

(73) Assignee: University of Maryland, College Park, College Park, MD (US)

( * ) Notice: Subject to any disclaimer, the term of this patent is extended or adjusted under 35 U.S.C. 154(b) by 166 days.

(21) Appl. No.: 12/092,845

(22) PCT Filed: Nov. 28, 2006

(86) PCT No.: PCT/US2006/061268

§ 371 (c)(1),
(2), (4) Date: May 7, 2008

(87) PCT Pub. No.: WO2007/065080

PCT Pub. Date: Jun. 7, 2007

(65) Prior Publication Data

US 2008/0280364 A1    Nov. 13, 2008

Related U.S. Application Data

(60) Provisional application No. 60/740,573, filed on Nov. 29, 2005, provisional application No. 60/804,501, filed on Jun. 12, 2006.

(51) Int. Cl.
*G01N 33/50*  (2006.01)
*G01N 33/92*  (2006.01)

(52) U.S. Cl. ............................. 436/63; 436/71; 435/29

(58) Field of Classification Search ................ 436/63, 436/71, 86; 435/4, 29
See application file for complete search history.

(56) References Cited

U.S. PATENT DOCUMENTS

| | | | |
|---|---|---|---|
| 6,248,904 B1 | 6/2001 | Zhang et al. | |
| 6,653,126 B1 * | 11/2003 | Steller et al. | 435/320.1 |
| 6,670,139 B1 * | 12/2003 | Fearnhead et al. | 435/7.21 |
| 6,808,873 B2 * | 10/2004 | Murphy et al. | 435/4 |
| 2004/0166545 A1 * | 8/2004 | Harr et al. | 435/7.23 |
| 2007/0184435 A1 * | 8/2007 | Garcia et al. | 435/5 |

OTHER PUBLICATIONS

Anishkin, A. et al. (2006) "Searching for the Molecular Arrangement of Transmembrane Ceramide Channels," Biophys. J. 90:2414-2426.
Antonsson, B. (2004) "Mitochondria and the Bcl-2 Family Proteins in Apoptosis Signaling Pathways," Mol. Cell Biochem. 256:141-155.
Bionda, C. et al. (2004) "Subcellular Compartmentalization of Ceramide Metabolism: MAM (Mitochondria-Associated Membrane and/or Mitochondria"? Biochem. J. 382:527-533.
Birbes, H. et al. (2002) "Mitochondria and Ceramide: Intertwined Roles in Regulation of Apoptosis," Advan. Enzyme Regul. 42:113-129.
Birbes, H. et al. (2005) "A Mitochondrial Pool of Sphingomyelin is Involved in TNFalpha-Induced Bax Translocation to Mitochondria," Biochem. J. 386:445-451.
Chen, H. et al. (2005) "Emerging Functions of Mammalian Mitochondrial Fusion and Fission," Hum Mol Genet. 14 Spec No. 2:R283-R289.
Cory, S. et al. (2003) "The BCL-2 Family: Roles in Cell Survival and Oncogenesis," Oncogene. 22:8590-8607.
Crompton, M. (1999) "The Mitochondrial Permeability Transition Pore and its Role in Cell Death," Biochem. J. 341:233-249.
Cuvillier, O. (2002) "Sphingosine in Apoptosis Signaling," Biochim. Biophys. Acta. 1585:153-162.
Danial, N. N. et al. (2004) "Cell Death: Critical Control Points," Cell 116:205-219.
Dbaibo, G.S. et al. (1997) "Cytokine Response Modifier a (CRMA) Inhibits Ceramide Formation in Response to Tumor Necrosis Factor (TNF)-Alpha: CRMA and Bcl-2 Target Distinct Components in the Apoptotic Pathway," J Exp Med. 185:481-490.
Di Paola, M. et al. (2004) "Ceramide Induces Release of Pro-Apoptotic Proteins From Mitochondria by Either a CA2+ -Dependent or a CA2+ -Independent Mechanism," J. Bioenerg. Biomembr. 36:165-170.
El Bawab, S. et al. (2000) "Molecular Cloning and Characterization of a Human Mitochondrial Ceramidase," J. Biol. Chem. 275:21508-21513.
Elrick, M.J. et al. (2006) "Sphingosine, A Product of Ceramide Hydrolysis, Influences the Formation of Ceramide Channels," Biophys. J. 1;91(5):1749-1756.
Garcia-Ruiz et al. (1997) ("Direct Effect of Ceramide on the Mitochondrial Electron Transport Chain Leads to Generation of Reactive Oxygen Species. Role of Mitochondrial Glutathione," J. Biol. Chem. 272:11369-11377.
Green D.R. et al. (2004) "The Pathophysiology of Mitochondrial Cell Death," Science 305:626-629.
Green, D.R. et al. (1998) "Mitochondria and Apoptosis," Science 281:1309-1312.
Kirkin, V. et al. (2004) "The Role of Bcl-2 Family Members in Tumorigenesis," Biochim. Biophys. Acta 1644:229-249.
Kluck, R.M. et al. (1999) "The Pro-Apoptotic Proteins, Bid and Bax, Cause a Limited Permeabilization of the Mitochondrial Outer Membrane That Is Enhanced by Cytosol," J. Cell. Biol. 147:809-822.
Kolesnick, R.N. et al. (1998) "Regulation of Ceramide Production and Apoptosis," Annu. Rev. Physiol. 60:643-665.
Kuwana, T. et al. (2002) "Bid, Bax, and Lipids Cooperate to Form Supramolecular Openings in the Outer Mitochondrial Membrane," Cell 111:331-342.
Masamune, A. et al. (1996) "Regulatory Role of Ceramide in Interleukin (IL)-1 Beta-Induced E-Selectin Expression in Human Umbilical Vein Endothelial Cells. Ceramide Enhances IL-1 Beta Action, but is Not Sufficient for E-Selectin Expression," J. Biol. Chem. 271:9368-9375.

(Continued)

*Primary Examiner*—Maureen M Wallenhorst
(74) *Attorney, Agent, or Firm*—Jeffrey I. Auerbach; Edell, Shapiro & Finnan, LLC

(57) ABSTRACT

The present invention relates to a novel target to control the apoptotic process, and to the use of this target to identify compounds capable of affecting the apoptotic process, The invention also relates to the use of such identified compounds in the treatment of cancer, stroke, neurodegenerative diseases, viral diseases and other diseases and conditions involving apoptosis.

20 Claims, 13 Drawing Sheets

OTHER PUBLICATIONS

Packham, G. et al. (2005) "Bodyguards and Assassins: Bcl-2 Family Proteins and Apoptosis Control Chronic Lymphocytic Leukaemia," Immunology. 114:441-449.

Pastorino, J.G. et al. (1999) "Functional Consequences of the Sustained or Transient Activation by Bax of the Mitochondrial Permeability Transition Pore," J. Biol. Chem. 274:31734-31739.

Perl, M. et al. (2005) "Apoptosis," Crit. Care Med. 33(12 Suppl):S526-S529.

Sawada M. et al. (2000) "Ordering of Ceramide Formation, Caspase Activation, and Bax/Bcl-2 Expression During Etoposide-Induced Apoptosis in C6 Glioma Cells," Cell Death Differ. 7:761-772.

Selzner, M. et al. (2001) "Induction of Apoptotic Cell Death and Prevention of Tumor Growth by Ceramide Analogues in Metastatic Human Colon Cancer," Cancer Res. 61:1233-1240.

Siskind, L.J. (2005) "Mitochondrial Ceramide and the Induction of Apoptosis," J. Bioenerg. Biomem. 37:143-153.

Siskind, L.J. et al. (2000) "The Lipids C2- and C16-Ceramide Form Large Stable Channels. Implications for Apoptosis," J. Biol. Chem. 275:38640-38644.

Siskind, L.J. et al. (2002) "Ceramide Channels Increase the Permeability of the Mitochondrial Outer Membrane to Small Proteins," J. Biol. Chem. 277:26796-26803.

Siskind, L.J. et al. (2003) "Enlargement and Contracture of C2-Ceramide Channels," Biophys. J. 85:1560-1575.

Siskind, L.J. (2005) "Sphingosine Forms Channels in Membranes That Differ Greatly From Those Formed by Ceramide," J. Bioenerg. Biomembr. 37:227-236.

Siskind, L.J. et al. (2006) "Ceramide Forms Channels in Mitochondrial Outer Membranes at Physiologically Relevant Concentrations," Mitochondrion 6(3):118-125 (Epub Mar. 29, 2006).

Solary, E. et al. (1996) "The Role of Apoptosis in the Pathogenesis and Treatment of Disease," Eur. Respir. J. 9:1293-1305.

Suzuki, E. et al. (2004) "Sphingosine-Dependent Apoptosis: A Unified Concept Based on Multiple Mechanisms Operating in Concert," Proc. Natl. Acad. Sci. USA 10141:14788-14793.

Terrones, O. et al. (2004) "Lipidic Pore Formation by the Concerted Action of Proapoptotic Bax and TBID," J. Biol. Chem. 279:30081-30091).

Vander Heiden, M.G. et al. (2000) "Outer Mitochondrial Membrane Permeability Can Regulate Coupled Respiration and Cell Survival," Proc. Natl. Acad. Sci. U.S.A. 97:4666-4671.

Von Haefen, C. et al. (2002) "Ceramide Induces Mitochondrial Activation and Apoptosis Via a Bax-Dependent Pathway in Human Carcinoma Cells," Oncogene 21:4009-4019.

\* cited by examiner

CONTROL OF APOPTOSIS BY CONTROLLING THE PROPENSITY OF CERAMIDE CHANNEL FORMATION

CROSS-REFERENCE TO RELATED APPLICATIONS

This application is a 371 of PCT/US06/61268, filed on Nov. 28, 2006 (now lapsed), and claims priority from United States Patent Applications Ser. Nos. 60/740,573 (filed on November 29, 2005) and 60/804,501 (filed on June 12, 2006), both of which applications are herein incorporated by reference in their entirety.

STATEMENT OF GOVERNMENTAL INTEREST

This invention was made using United States Governmental funds (NIH NS042025). The United States Government may have certain rights in this invention.

FIELD OF THE INVENTION

The present invention relates to a novel target to control the apoptotic process, and to the use of this target to identify compounds capable of affecting the apoptotic process. The invention also relates to the use of such identified compounds in the treatment of cancer, stroke, neurodegenerative diseases, viral diseases and other diseases and conditions involving apoptosis.

BACKGROUND OF THE INVENTION

Apoptosis, the morphological process leading to the controlled death of a cell, is essential for cellular homeostasis in multicellular organisms (Perl, M. et al. (2005) "APOPTOSIS," Crit. Care Med. 33(12 Suppl):S526-S529). It provides a way of eliminating cells that are damaged or differentiated cells that are no longer necessary. For example, in the brain, only about half of the embryonic neurons generated are actually present in the adult brain; those that do not survive die via apoptosis (Snyder, S. H. (1999) "DRUGS FOR A NEW MILLENNIUM," Philos. Trans. R. Soc. Lond. B Biol. Sci. 354:1985-1994 Snyder, 1999). However, apoptosis can be activated inappropriately; in stroke, heart disease, and neurodegenerative disorders and can result in the unnecessary loss of cells and their associated functions. Apoptosis can also be suppressed inappropriately in tumor cells and cells infected by viruses. Indeed, some viruses encode proteins capable of inhibiting the apoptotic process (Hardwick, J. M. (1998) "VIRAL INTERFERENCE WITH APOPTOSIS," Semin. Cell Dev. Biol. 9:339-349). Further, the major treatments used to kill cancer cells, radiation and chemotherapy, function by inducing apoptosis and cells that become resistant to these treatments often do so by inhibiting the apoptotic process (Hannun, Y. A. (1997) "APOPTOSIS AND THE DILEMMA OF CANCER CHEMOTHERAPY," Blood. 89:1845-1853). Thus, an ability to control apoptosis is of fundamental importance to the treatment of numerous diseases.

There are currently two known pathways for apoptosis: an extrinsic pathway and an intrinsic pathway. Extrinsic apoptosis signaling is mediated by the activation of so called "death receptors" which are cell surface receptors that transmit apoptotic signals after ligation with specific ligands. Death receptors belong to the tumor necrosis factor receptor (TNFR) gene superfamily, including TNFR-1, Fas/CD95, and the TRAIL receptors DR-4 and DR-5 (Ashkenazi, A (2002) "TARGETING DEATH AND DECOY RECEPTORS OF THE TUMOUR-NECROSIS FACTOR SUPERFAMILY," Nat. Rev. Cancer 2(6): 420-430).

The mitochondrion is known to act as a major hub for the regulation of intrinsic apoptosis (Chen, H. et al. (2005) "EMERGING FUNCTIONS OF MAMMALIAN MITOCHONDRIAL FUSION AND FISSION," Hum Mol Genet. 14 Spec No. 2:R283—R289; Mohamad, N. et al. (2005) "MITOCHONDRIAL APOPTOTIC PATHWAYS," Biocell. 29(2):149-61). Early in mitochondria-mediated apoptosis, there is an increase in the permeability of the mitochondrial outer membrane (MOM) that leads to the release of intermembrane space proteins, including cytochrome c, procaspases, apoptosis-inducing factor (AIF), heat shock proteins, Smac/Diablo, and endonuclease G (Saelens, X. et al. (2004) "TOXIC PROTEINS RELEASED FROM MITOCHONDRIA IN CELL DEATH," Oncogene 23:2861-2874). The release of these proapoptotic proteins into the cytoplasm is crucial for the activation of specific caspases and DNases that are responsible for the execution of apoptosis. The key event of this mitochondrial pathway is the permeabilization of the mitochondrial outer membrane (MOM) to proteins and the efflux of apoptosis-inducing intermembrane space proteins such as cytochrome c into the cytoplasm. The release of these proteins leads to the activation of the caspases that carry out the execution phase of apoptosis (Crompton, M. (1999) "THE MITOCHONDRIAL PERMEABILITY TRANSITION PORE AND ITS ROLE IN CELL DEATH," Biochem. J. 341:233-249; Susin, S. A. et al. (1998) "MITOCHONDRIA AS REGULATORS OF APOPTOSIS: DOUBT NO MORE," Biochim. Biophys. Acta. 1366:151-165). Cells can be rescued before this step but are generally fated to die once the proapoptotic proteins have been released from mitochondria. Therefore, an understanding of the mechanism for the permeabilization of the MOM to proteins is relevant to developing methods for controlling apoptosis.

A number of mechanisms have been proposed for the protein permeation pathway. Candidates for the composition of this pore include Bax oligomers (Antonsson, B. et al. (2000) "BAX OLIGOMERIZATION IS REQUIRED FOR CHANNEL-FORMING ACTIVITY IN LIPOSOMES AND TO TRIGGER CYTOCHROME C RELEASE FROM MITOCHONDRIA," Biochem. J. 345:271-278; Antonsson, B. (2001) "BAX IS PRESENT AS A HIGH MOLECULAR WEIGHT OLIGOMER/COMPLEX IN THE MITOCHONDRIAL MEMBRANE OF APOPTOTIC CELLS," J. Biol. Chem. 276:11615-11623; Saito, M. et al. (2000) "BAX-DEPENDENT TRANSPORT OF CYTOCHROME C RECONSTITUTED IN PURE LIPOSOMES," Nat. Cell Biol. 2:553-555; Pavlov, E. V. et al. (2001) "A NOVEL, HIGH CONDUCTANCE CHANNEL OF MITOCHONDRIA LINKED TO APOPTOSIS IN MAMMALIAN CELLS AND BAX EXPRESSION IN YEAST," J. Cell Biol. 155:725-73), the mitochondrial apoptosis-induced channel MAC (Pavlov, E. V. et al. (2001) "A NOVEL, HIGH CONDUCTANCE CHANNEL OF MITOCHONDRIA LINKED TO APOPTOSIS IN MAMMALIAN CELLS AND BAX EXPRESSION IN YEAST," J. Cell Biol. 155:725-731), lipidic pores induced by Bax (Basañez, G. et al. (1999) "BAX, BUT NOT BCL-XL, DECREASES THE LIFETIME OF PLANAR PHOSPHOLIPID BILAYER MEMBRANES AT SUBNANOMOLAR CONCENTRATIONS," Proc. Natl. Acad. Sci. USA 96:5492-5497), lipidic pores induced by BH3/Bax/lipid interactions (Kuwana, T. et al. (2002) "BID, BAX, AND LIPIDS COOPERATE TO FORM SUPRAMOLECULAR OPENINGS IN THE OUTER MITOCHONDRIAL MEMBRANE," Cell 111:331-342; Terrones, O. et al. (2004) "LIPIDIC PORE FORMATION BY THE CONCERTED ACTION OF PROAPOPTOTIC BAX AND TBID," J. Biol. Chem. 279:30081-30091), interactions between Bax and ceramide (Pastorino, J. G. et al. (1999) "FUNCTIONAL CONSEQUENCES OF THE SUSTAINED OR TRANSIENT ACTIVATION BY BAX OF THE MITOCHONDRIAL PERMEABILITY TRANSITION PORE," J. Biol. Chem. 274:31734-31739), and ceramide channels (Siskind, L. J. et al. (2000) "THE LIPIDS $C_2$- AND $C_{16}$-CERAMIDE FORM LARGE STABLE CHANNELS. IMPLICATIONS FOR APOPTOSIS," J. Biol. Chem. 275:38640-38644; Siskind, L. J. et al. (2002) "CERAMIDE CHANNELS INCREASE THE PERMEABILITY OF THE MITOCHONDRIAL OUTER MEMBRANE TO SMALL PROTEINS," J. Biol. Chem. 277:26796-26803; Siskind, L. J. et al. (2003) "ENLARGEMENT AND CONTRACTURE OF $C_2$-CERAMIDE CHANNELS," Biophys. J. 85:1560-1575).

A variety of assays have been developed to assess apoptosis. For example, apoptosis has been assayed using DNA stains able to detect the breakdown of the cell nucleus (see, for example, U.S. Pat. No. 6,248,904; Briant, L. et al. (1998) "INVOLVEMENT OF EXTRACELLULAR SIGNAL-REGULATED KINASE MODULE IN HIV-MEDIATED CD4 SIGNALS CONTROLLING ACTIVATION OF NUCLEAR FACTOR-KAPPA B AND AP-1 TRANSCRIPTION FACTORS," J. Immunol. 160:1875-1885); by DNA electrophoresis or flow cytometry (see, for example, Gong, J, et al. (1994) "A SELECTIVE PROCEDURE FOR DNA EXTRACTION FROM APOPTOTIC CELLS APPLICABLE FOR GEL ELECTROPHORESIS AND FLOW CYTOMETRY," Anal. Biochem. 218:314-319; Belloc, F. et al. (1994) "A FLOW CYTOMETRIC METHOD USING HOECHST 33342 AND PROPIDIUM IODIDE FOR SIMULTANEOUS CELL CYCLE ANALYSIS AND APOPTOSIS DETERMINATION IN UNFIXED CELLS," Cytometry 17:59-65; Singh, N. P. et al. (1994) "MODIFICATIONS OF ALKALINE MICROGEL ELECTROPHORESIS FOR SENSITIVE DETECTION OF DNA DAMAGE," Int. J. Radiat. Biol. 66:23-28 (1994). Apoptosis has been assayed using caspase assays (Darzynkiewicz, Z. et al. (2001) "FLOW CYTOMETRY IN ANALYSIS OF CELL CYCLE AND APOPTOSIS," Semin Hematol. 38(2):179-93); Riss, T. L. (2001) "APOPTOSIS AS A BIOMARKER IN CHEMOPREVENTION TRIALS," Urology. 57(4 Suppl 1): 141-142; Saraste, A. et al. (2000) "MORPHOLOGIC AND BIOCHEMICAL HALLMARKS OF APOPTOSIS," Cardiovasc Res. 45(3):528-537). Various assays have been developed to detect apoptosis based on changes that occur in the permeability of cell membranes (see, for example, Idziorek, T. et al. (1995) ("YOPRO-1 PERMITS CYTOFLUOROMETRIC ANALYSIS OF PROGRAMMED CELL DEATH (APOPTOSIS) WITHOUT INTERFERING WITH CELL VIABILITY," J. Immunol. Methods 185:249-258; Susin, S. A. et al. (1998) "MITOCHONDRIA AS REGULATORS OF APOPTOSIS: DOUBT NO MORE," Biochim. Biophys. Acta 1366:151-165; Green, D. R. et al. (1998) "MITOCHONDRIA AND APOPTOSIS," Science 281:1309-1312).

Despite all such progress, a need remains for improved methods for assaying apoptosis and for identifying compounds that affect apoptosis. The identification of such compounds would provide an ability to control apoptosis and thereby permit the treatment of major diseases such as cancer, stroke, heart disease, neurodegenerative diseases, and viral diseases, for which current treatments are seriously inadequate. The present invention is directed to these and other needs.

SUMMARY OF THE INVENTION

The present invention relates to a novel target to control the apoptotic process, and to the use of this target to identify compounds capable of affecting the apoptotic process. The invention also relates to the use of such identified compounds in the treatment of cancer, stroke, neurodegenerative diseases, viral diseases and other diseases and conditions involving apoptosis.

Ceramides are known to have a regulatory function in apoptosis, including the release of cytochrome c and other proapoptotic factors from the mitochondrial intermembrane space. Ceramides can form large, stable channels in the outer ritochondrial membrane, leading to the proposal that ceramide channels are the pathway through which these proteins are released. The present invention derives in part from the recognition that sphingosine, a product of ceramide hydrolysis by ceramidase, is capable of destabilizing ceramide channels, leading to their disassembly. Sphingosine is directly responsible for the disassembly of ceramide channels in planar membrane experiments and markedly reduces the ability of ceramide to induce the release of intermembrane space proteins from mitochondria in vitro. Low concentrations of both L and D sphingosine potentiate the release of intermembrane space proteins by long-chain ceramide and channel formation in liposomes. Such potentiation provides a mechanism through which ceramide channel formation is enhanced thus initiating the apoptotic cascade or increasing the likelihood that apoptosis will be initiated. Higher levels of these compounds inhibit ceramide channel formation and induce the disassembly of existing ceramide channels. All this occurs at levels of sphingosine that are at the very low micromolar range. This demonstrates that compounds exist that can either favor or disfavor the formation of ceramide channels. While sphingosine itself would not be a useful therapeutic agent, due to the presence of unwanted side effects, the identification of the novel drug target of the present invention permits the identification of compounds that would lack such side effects and thus would comprise valuable therapeutic agents. The present invention permits one to identify apoptotic effector compounds by their ability to potentiate or inhibit ceramide channel formation and as such permits one to identify compounds capable of treating diseases involving mitochondria-mediated apoptosis. Recent validation of the importance of this target is the discovery that anti-apoptotic proteins actually act at this site. Both Bcl-xL and a truncated version of CED-9, an anti-apoptotic protein found in worms, act to inhibit and reverse long-chain ceramide-induced permeabilization of mitochondrial outer membrane to cytochrome c. In addition, in a defined planar phospholipids membrane system, both of these proteins caused long-chain ceramide channel disassembly. Thus these anti-apoptotic proteins target ceramide channels. In detail, the invention provides a method for identifying an apoptotic effector compound, wherein the method comprises the steps of:

(A) incubating a phospholipid membrane under conditions sufficient to permit the formation of ceramide channels through the membrane;

(B) incubating the phospholipid membrane in the presence of a candidate apoptotic effector compound; and (C) determining whether the presence of the candidate apoptotic effector compound affects the formation or stability of the ceramide channels, relative to the extent of such formation or stability observed in the absence of the candidate apoptotic effector compound;

wherein a compound that affects the formation or stability of the ceramide channels is an apoptotic effector compound.

The invention also provides the embodiment of the above method, wherein step (B) is performed prior to performing the step (A).

The invention also provides the embodiments of the above methods, wherein the conditions (A) sufficient to permit the formation of ceramide channels comprise providing a ceramide (especially wherein the ceramide is $C_{16}$-ceramide) to the phospholipid membrane.

The invention also provides the embodiments of the above methods, wherein the phospholipid membrane is of defined composition and is a planar membrane or a liposome membrane. The invention also provides the sub-embodiments of such embodiments wherein the conditions (A) sufficient to permit the formation of ceramide channels comprise providing an agent selected from the group consisting of: nitrous oxide, etoposide, staurosporine, daunorubicin and dexamethasone.

The invention also provides the embodiments of the above methods, wherein the phospholipid membrane is a membrane of a mitochondrion, or a cellular membrane of a yeast or mammalian cell. The invention also provides the sub-embodiments of such embodiments wherein the conditions (A) sufficient to permit the formation of ceramide channels comprise: (i) providing an agent selected from the group consisting of: TNF-alpha, interleukin-1, nitrous oxide, etoposide, staurosporine, daunorubicin and dexamethasone, and/or (ii) subjecting the membrane to ionizing radiation, hypoxia or heat and/or subjecting the cell to serum withdrawal.

The invention also provides the sub-embodiments of the above embodiments, wherein the phospholipid membrane is a membrane of a mitochondrion, and especially wherein the mitochondrion lacks Bcl-2 proteins.

The invention also provides the sub-embodiments of the above embodiments, wherein the phospholipid membrane is a cellular membrane of a yeast or mammalian cell, and especially wherein the cell is Bax or Bak deficient.

The invention particularly provides the embodiments of all such methods wherein the candidate apoptotic effector compound inhibits the formation or stability of the ceramide channels, relative to the extent of such formation or stability observed in the absence of the candidate apoptotic effector compound.

The invention particularly provides the embodiments of all such methods wherein the candidate apoptotic effector compound inhibits the formation of ceramide channels but does not affect the stability of formed ceramide channels, relative to the extent of such formation or stability observed in the absence of the candidate apoptotic effector compound.

The invention particularly provides the embodiments of all such methods wherein the candidate apoptotic effector compound induces the formation of, or enhances the stability of, the ceramide channels, relative to the extent of such formation or stability observed in the absence of the candidate apoptotic effector compound.

The invention particularly provides the embodiments of all such methods wherein the candidate apoptotic effector compound inhibits the formation induces the formation of, or enhances the stability of, the ceramide channels, relative to the extent of such formation or stability observed in the absence of the candidate apoptotic effector compound.

The invention further provides an apoptotic effector compound whose apoptotic effect is measured by a method comprising the steps of:
(A) incubating a phospholipid membrane under conditions sufficient to permit the formation of ceramide channels through the membrane;
(B) incubating the phospholipid membrane in the presence of the apoptotic effector compound; and
(C) measuring the compounds apoptotic effect by determining the affect of the compound on the formation or stability of the ceramide channels, relative to the extent of such formation or stability observed in the absence of the compound.

The invention also provides an apoptotic effector compound, wherein step (B) is performed prior to performing the step (A).

The invention also provides an apoptotic effector compound, wherein the conditions (A) sufficient to permit the formation of ceramide channels comprise providing a ceramide (especially wherein the ceramide is $C_{16}$-ceramide) to the phospholipid membrane.

The invention also provides an apoptotic effector compound, wherein the phospholipid membrane is of defined composition and is a planar membrane or a liposome membrane. The invention also provides the sub-embodiments of such embodiments wherein the conditions (A) sufficient to permit the formation of ceramide channels comprise providing an agent selected from the group consisting of: nitrous oxide, etoposide, staurosporine, daunorubicin and dexamethasone.

The invention also provides an apoptotic effector compound, wherein the phospholipid membrane is a membrane of a mitochondrion, or a cellular membrane of a yeast or mammalian cell. The invention also provides the sub-embodiments of such embodiments wherein the conditions (A) sufficient to permit the formation of ceramide channels comprise: (i) providing an agent selected from the group consisting of: TNF-alpha, interleukin-1, nitrous oxide, etoposide, staurosporine, daunorubicin and dexamethasone, and/or (ii) subjecting the membrane to ionizing radiation, hypoxia or heat and/or subjecting the cell to serum withdrawal.

The invention also provides an apoptotic effector compound, wherein the phospholipid membrane is a membrane of a mitochondrion, and especially wherein the mitochondrion lacks Bcl-2 proteins.

The invention also provides an apoptotic effector compound, wherein the phospholipid membrane is a cellular membrane of a yeast or mammalian cell, and especially wherein the cell is Bax or Bak deficient.

The invention particularly provides an apoptotic effector compound which inhibits the formation or stability of the ceramide channels, relative to the extent of such formation or stability observed in the absence of the candidate apoptotic effector compound.

The invention particularly provides an apoptotic effector compound which inhibits the formation of ceramide channels but does not affect the stability of formed ceramide channels, relative to the extent of such formation or stability observed in the absence of the candidate apoptotic effector compound.

The invention particularly provides an apoptotic effector compound which induces the formation of, or enhances the stability of, the ceramide channels, relative to the extent of such formation or stability observed in the absence of the candidate apoptotic effector compound.

The invention particularly provides an apoptotic effector compound which inhibits the formation induces the formation of, or enhances the stability of, the ceramide channels, relative to the extent of such formation or stability observed in the absence of the candidate apoptotic effector compound.

The levels of adenylate kinase activity released by hypotonic shock or after addition of the vehicle alone are indicated as horizontal lines. The data is a typical result of four experiments performed on different batches of mitochondria.

Figure 3:
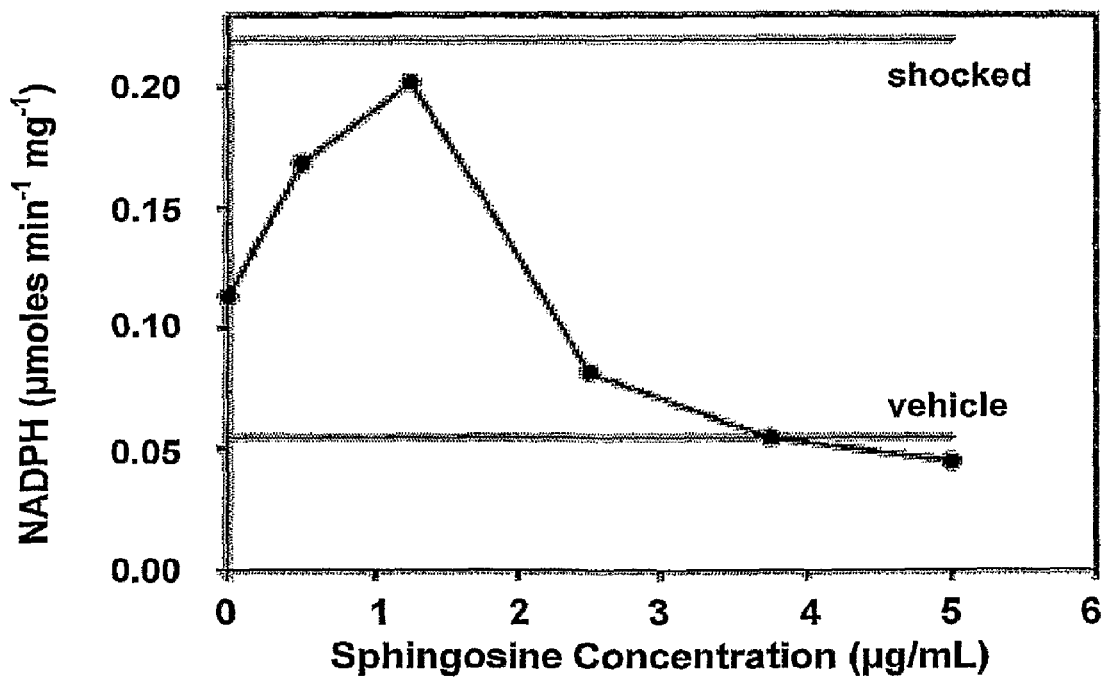
FIG. 3 shows that sphingosine inhibits the release of adenylate kinase from mitochondria induced by $C_{16}$-ceramide.
Figure 4:
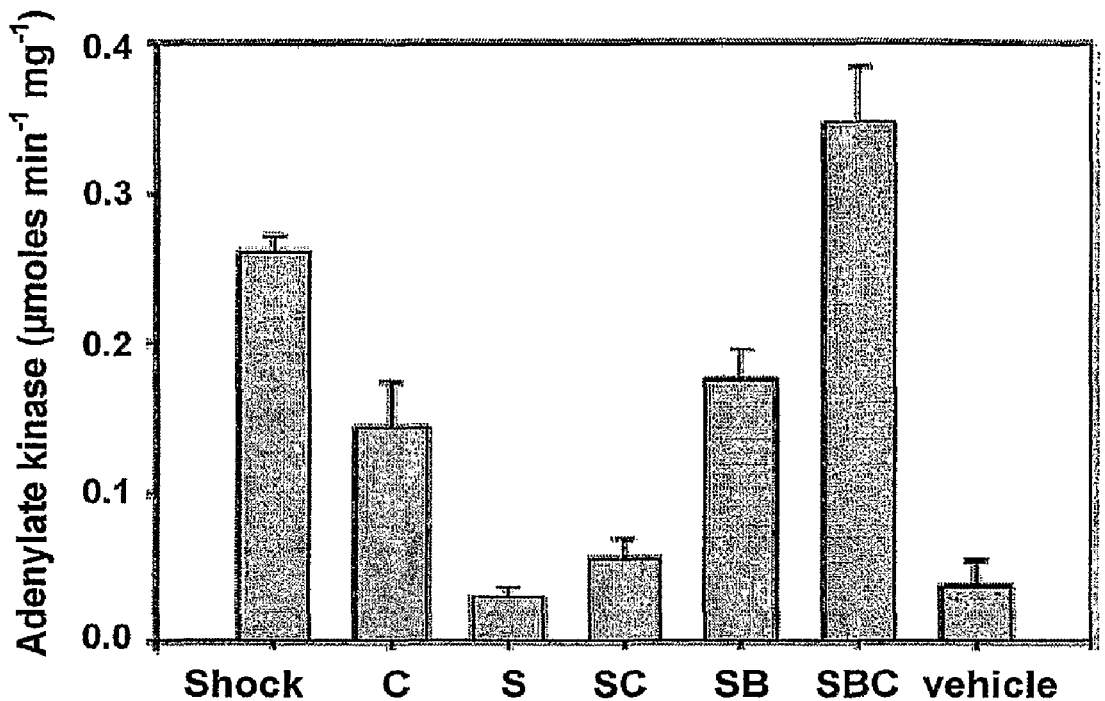

FIG. 4 shows that the removal of sphingosine by BSA reverses the inhibition by sphingosine of $C_{16}$-ceramide permeabilization of the mitochondrial outer membrane. The experiments were performed as in FIG. 3. BSA (bovine serum albumin), fatty acid depleted, was added just before addition of $C_{16}$-ceramide. The treatments were as follows: "shock", hypotonic shock only; "C", ceramide added only 40 µg/mL; "S", sphingosine 2.5 µg/mL; "SC", sphingosine 2.5 µg/mL followed by C16-ceramide 40 µg/mL; "SB", sphingosine 2.5 µg/mL for 5 min followed by BSA 7 mg/mL; "SBC", sphingosine 2.5 µg/mL for 5 min followed by BSA 7 mg/mL and C16-ceramide 40 µg/mL; and "vehicle", instead of ceramide isopropanol was added. The error bars are mean a SE of three independent experiments except for shock n=7, S n=5, and SB n=5. Student's t-tests showed that "SC" and "SBC" differ at the 99% confidence level; "S" and "SB" at the 99.9% level; "C" and "SC" at the 95% level; and "C" and "SCB" at the 95% level.

Figure 2:
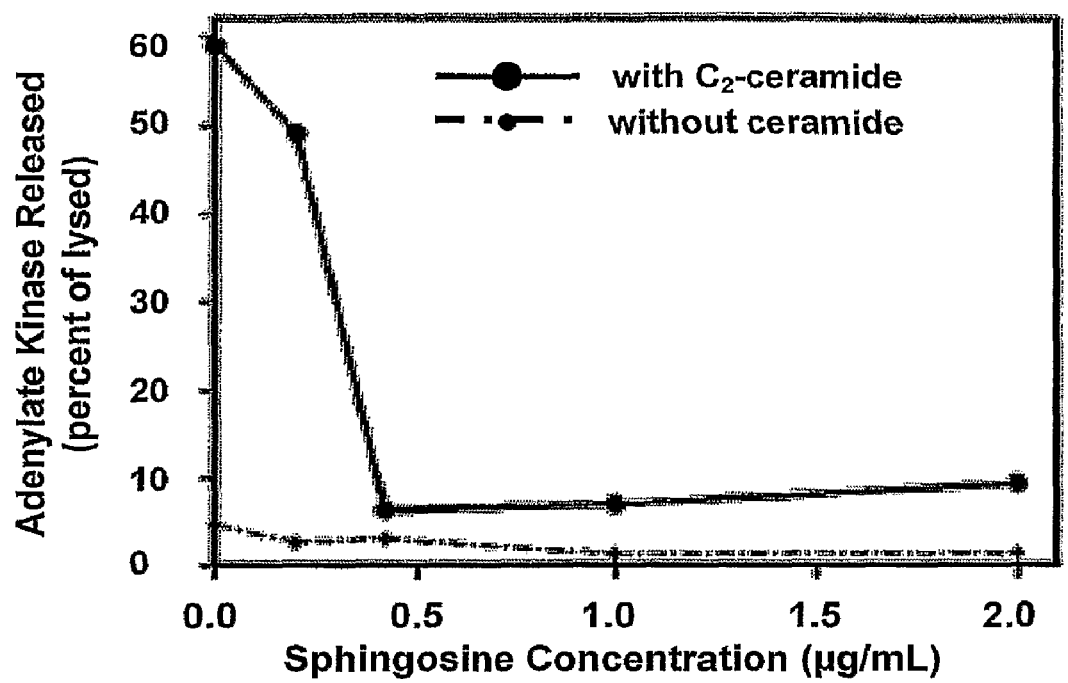
FIG. 2 shows the ability of sphingosine to inhibit the ceramide-dependent release of adenylate kinase from mitochondria. The release of adenylate kinase is expressed as a percentage of that released by hypotonic shock. The enzyme activity was recorded as the initial rate of NADPH production. The experiment was repeated without the addition of ceramide, and this data is also presented for comparison. The data shown is one representative example of three independent experiments.
Figure 5:
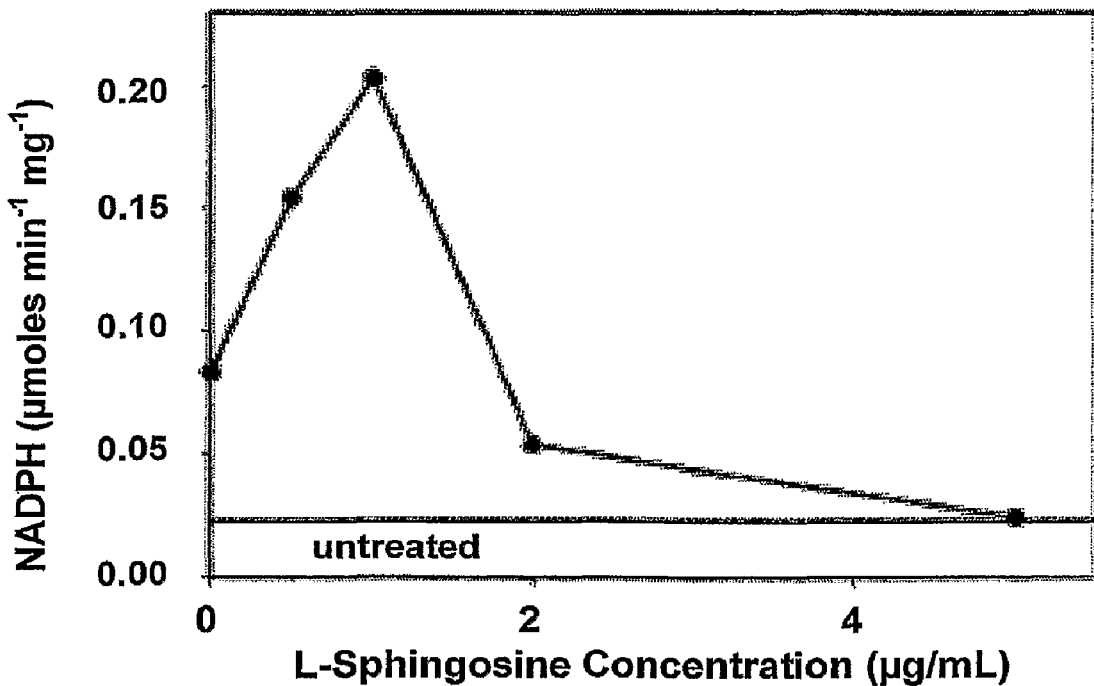

FIG. 5 shows the results of experiments performed as described in FIG. 2 except that the L isomer of sphingosine was used instead of the naturally occurring D isomer. "Untreated" refers to the level of adenylate kinase detected in the supernatant when no reagent was added. Otherwise the mitochondria were handled in exactly the same way as those treated with sphingosine.

Figure 6A:
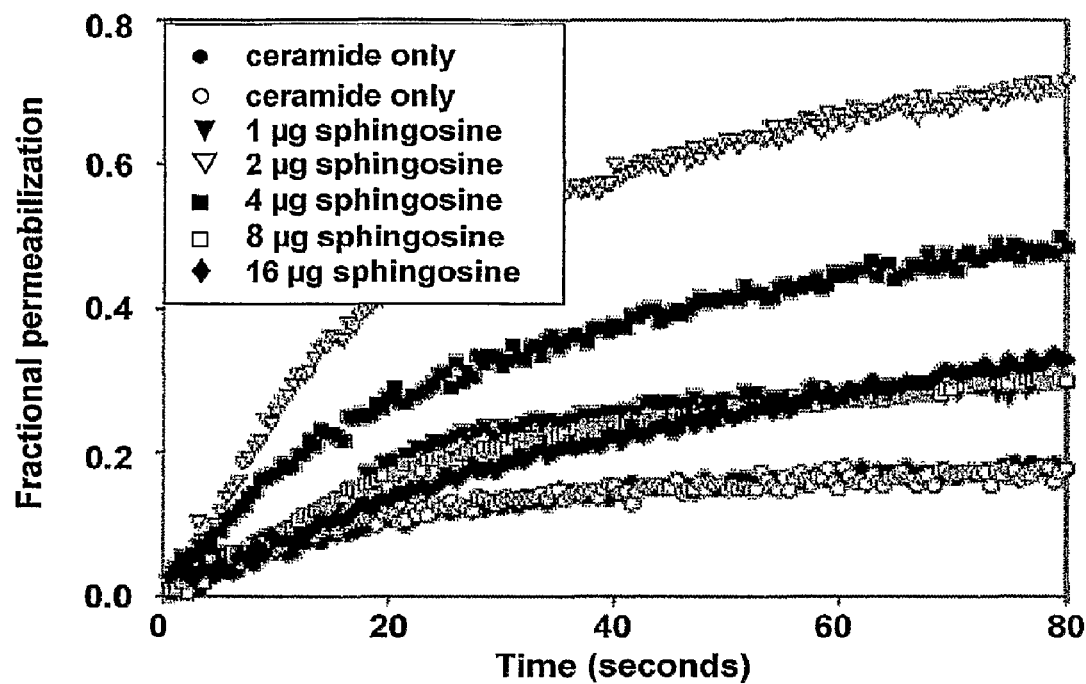
Figure 6B:
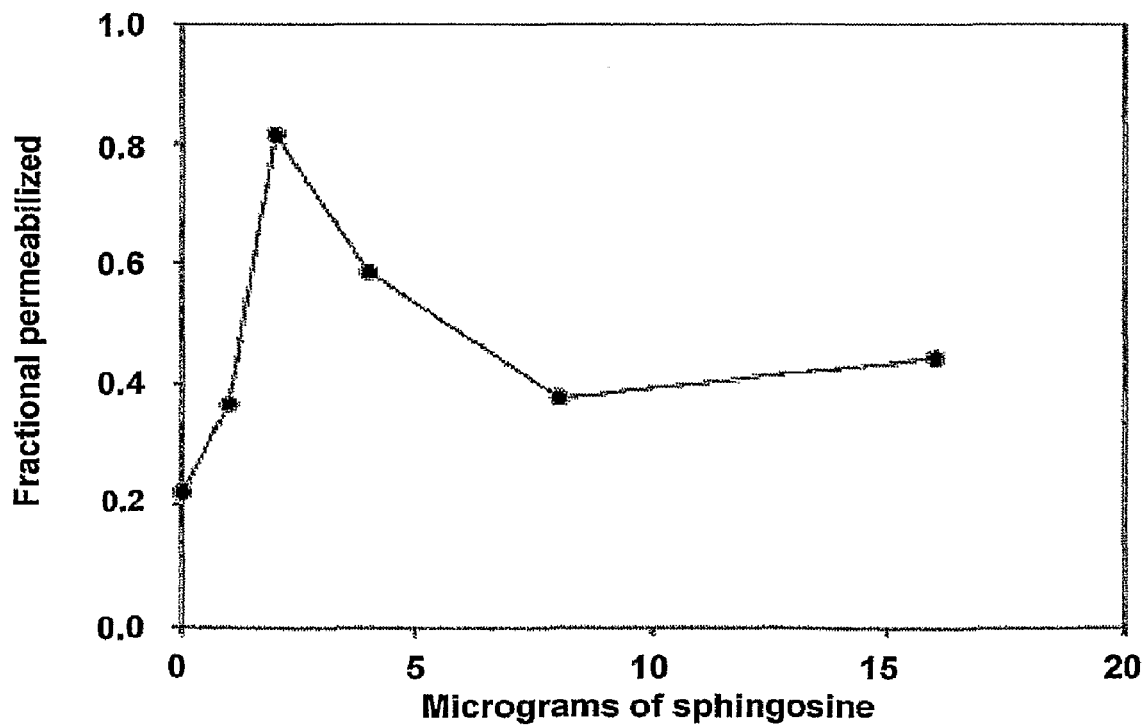

FIG. 6A and FIG. 6B show that sphingosine influences ceramide channel formation in liposomes in a biphasic fashion. (A) The release of carboxyfluorescein from liposomes by $C_{16}$-ceramide (80 µg) alone or after the liposomes (90 µg of lipid) were pretreated with the indicated amounts of sphingosine. The release is expressed as a fraction of the release achieved with 0.08% Triton X100. (B) The fluorescence level achieved in the experiments described in (A) 100 s after ceramide addition. Results are representative of two experiments.

Figure 7:
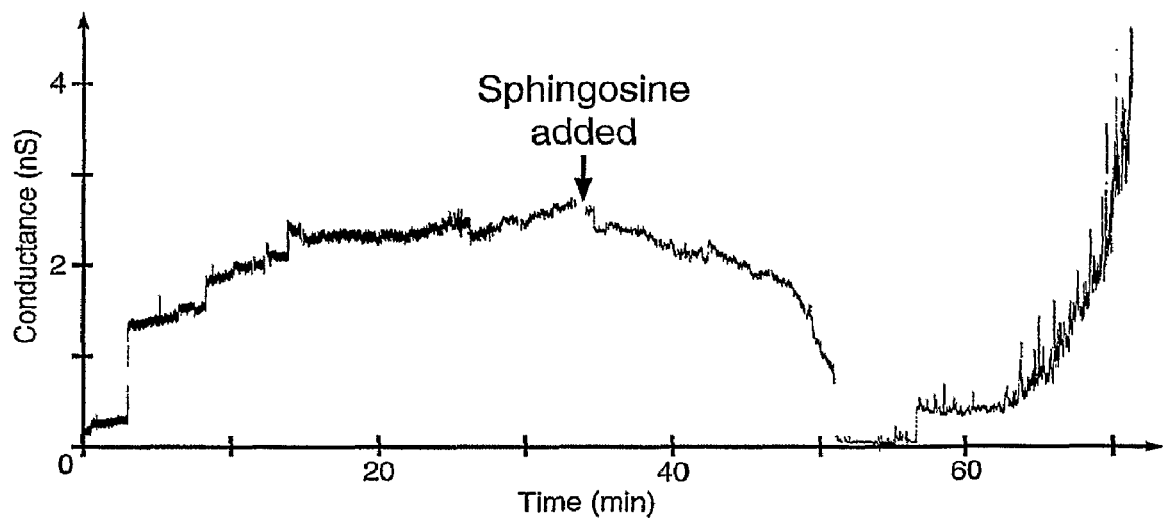

FIG. 7 shows that changes in conductance demonstrate ceramide channel disassembly. A ceramide channel was allowed to form after the addition of $C_2$-ceramide (9 µg/mL) to each side of the membrane. Once channel growth had slowed, sphingosine (4 µg/mL) was added to the cis side of the membrane, at the time indicated. FIG. 7 shows the continuous recording of conductance across the membrane. The applied voltage was clamped at 10 mV.

Figure 8:
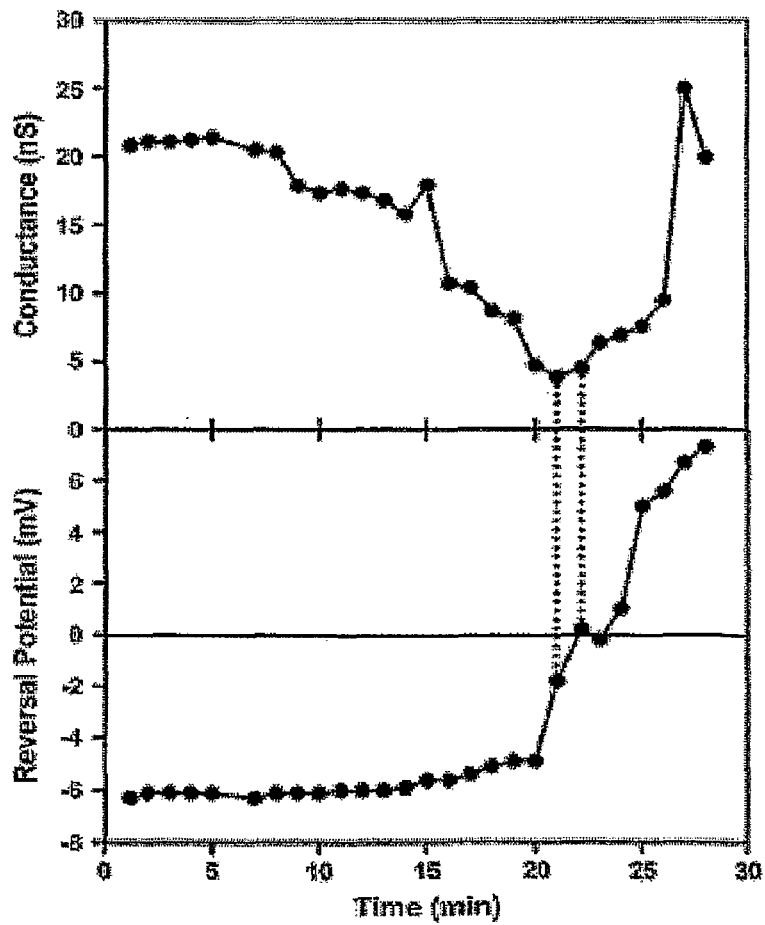

FIG. 8 shows that changes in reversal potential indicate changes in channel composition. A ceramide channel was formed after the addition of $C_2$-ceramide (3 µg/mL) to each side of the membrane. After channel growth slowed, KCl was added to the aqueous solution on the cis side of the membrane to a final concentration of 0.45 M. $MgCl_2$ and Pipes concentrations remained unchanged. The channel-containing membrane was then left undisturbed for 30 min. Sphingosine was added to a final concentration of 8 µg/mL at t=0 min. The conductance and reversal potential of the channel was measured periodically over the following 30 min. The presented data is one of three independent experiments.

Figure 9:
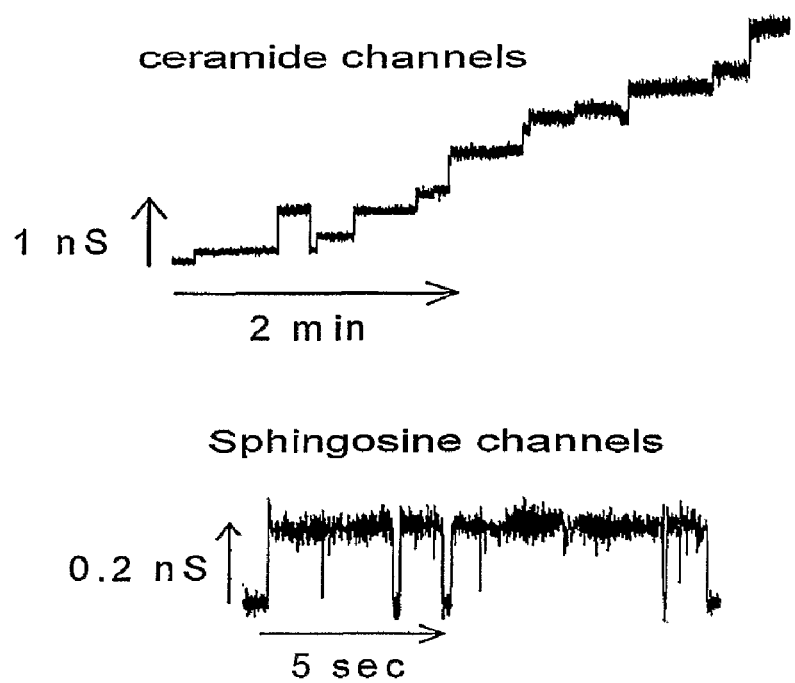

FIG. 9 shows a comparison of ceramide and sphingosine channels.

Figure 10:
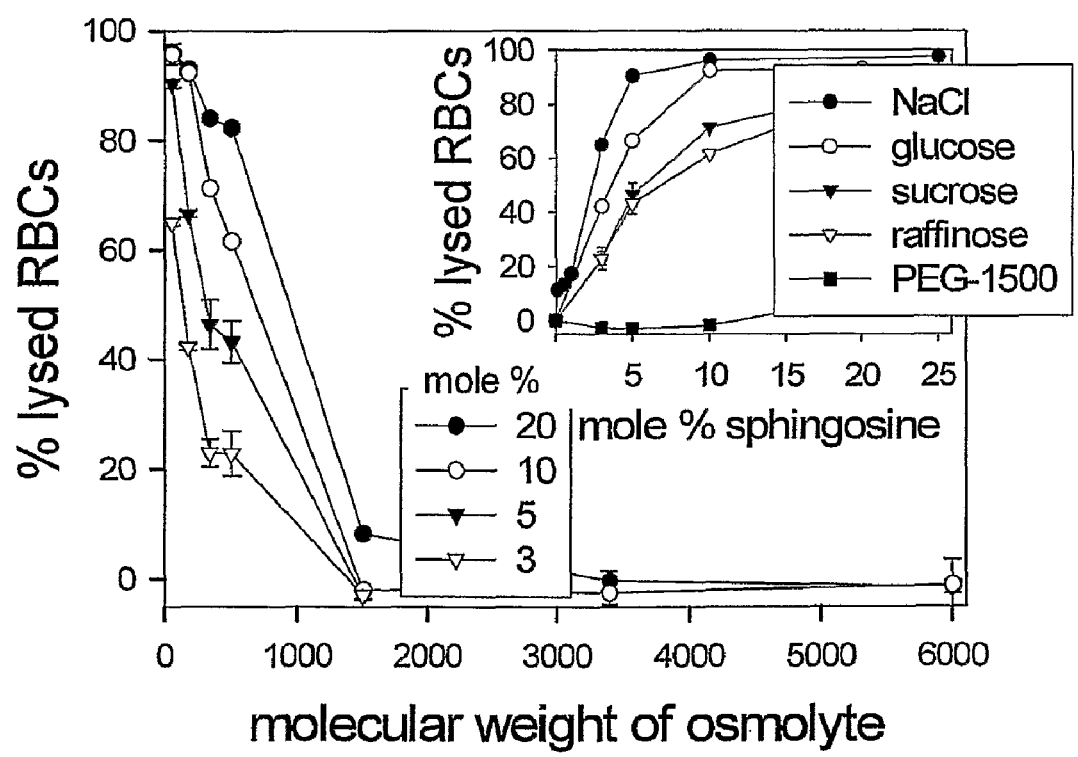

FIG. 10 shows that sphingosine channels in erythrocytes have a molecular weight cut off of 1 kDa. Main Figure: Erythrocytes in solutions of osmolytes with varying molecular weights were incubated with the indicated mole percent of sphingosine for 15 min. In the inset the data is expressed as a function of the mole percent of sphingosine.

Figure 11:
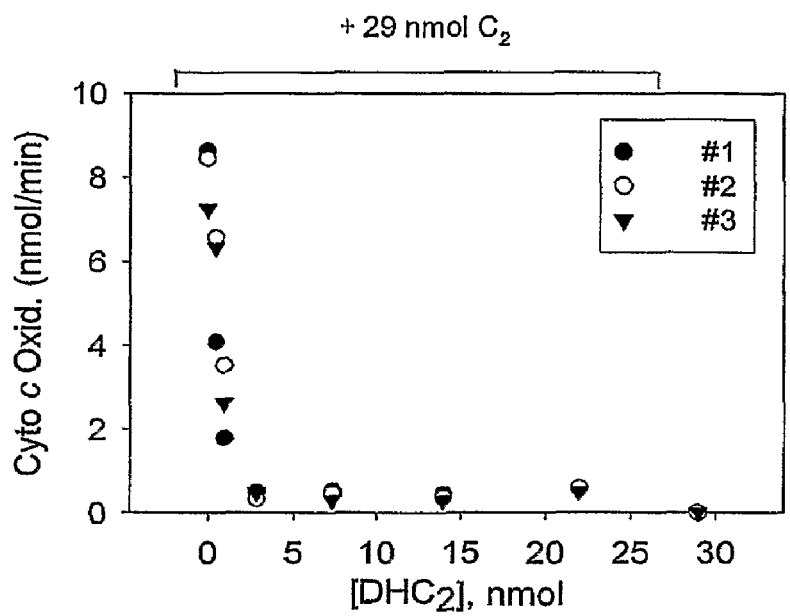

FIG. 11 shows the results of 3 experiments demonstrating the ability of dihydroceramide to inhibit the formation of ceramide channels in mitochondrial outer membranes. The permeability was monitored by recording the rate of oxidation of exogenously-added cytochrome c. Ceramide ($C_2$) was present at all data points except for the highest amount of dihydroceramide (DHC2) added (29 nmol).

Figure 12:
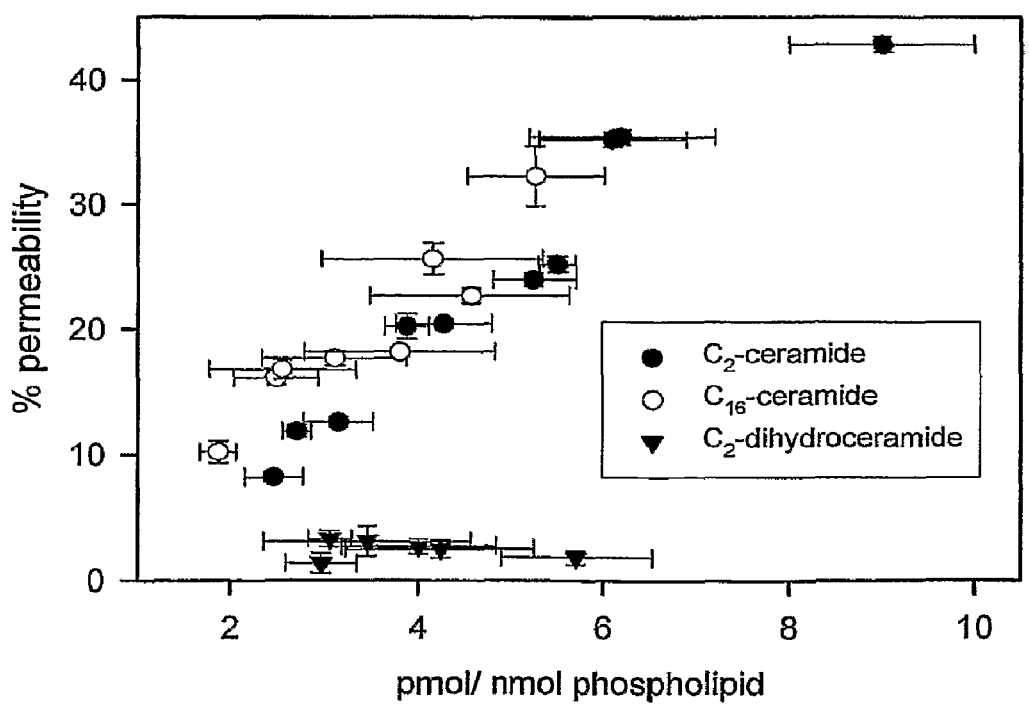

FIG. 12 shows the correlation of the permeability induced in the mitochondrial outer membrane with the amount of ceramide inserted into that membrane. This shows that ceramide forms channels in the mitochondrial outer membrane at physiologically-relevant concentrations.

Figure 13A:
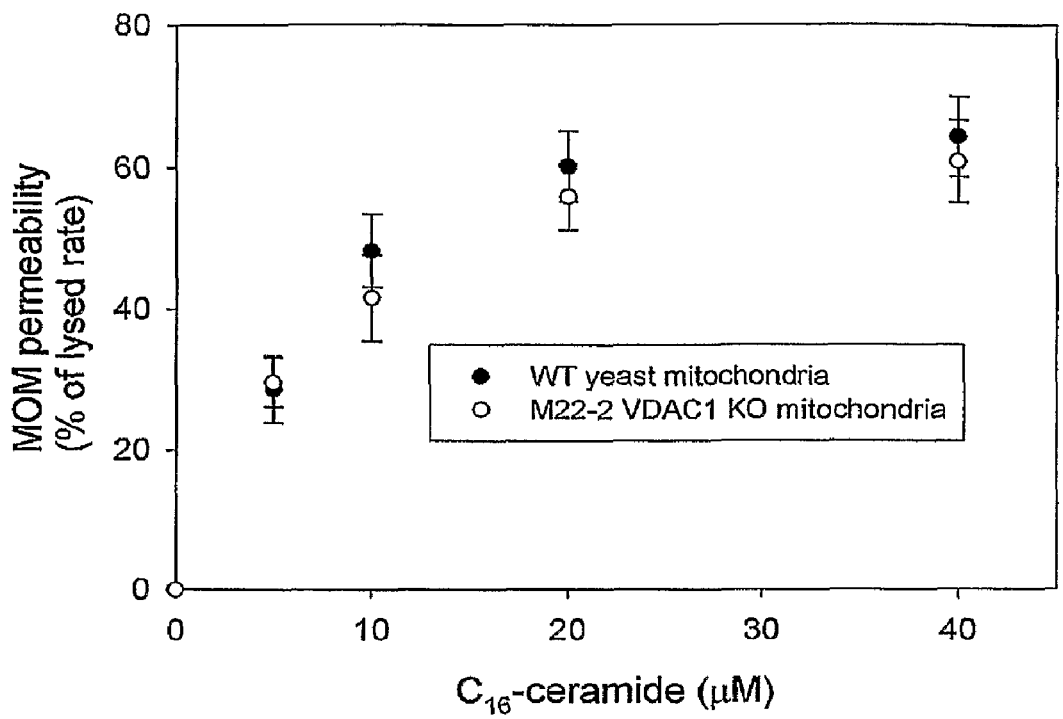
Figure 13B:
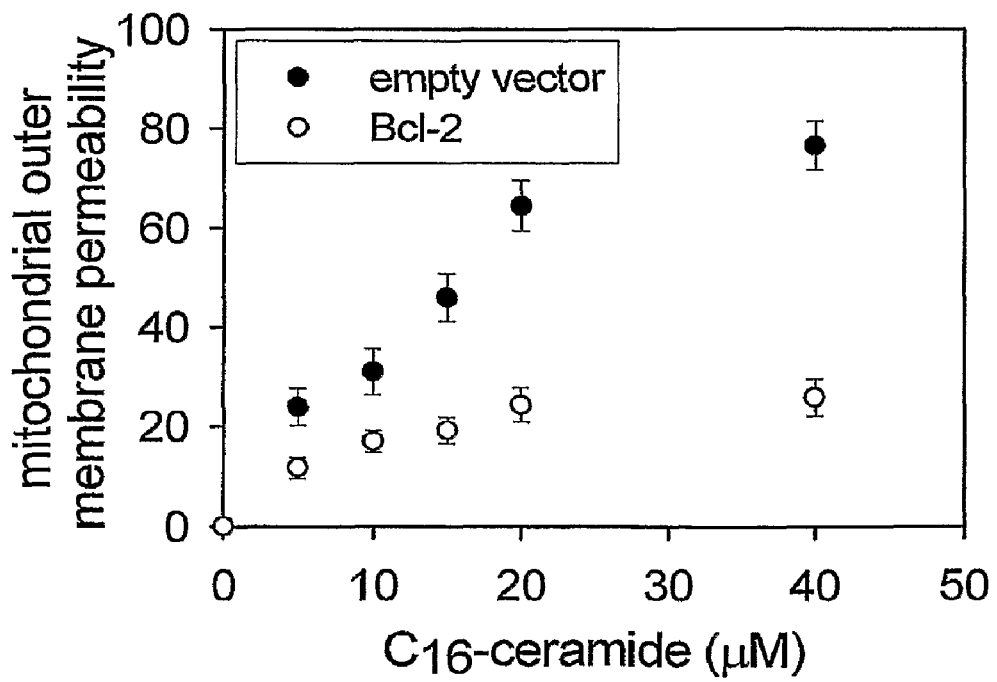
Figure 13C:
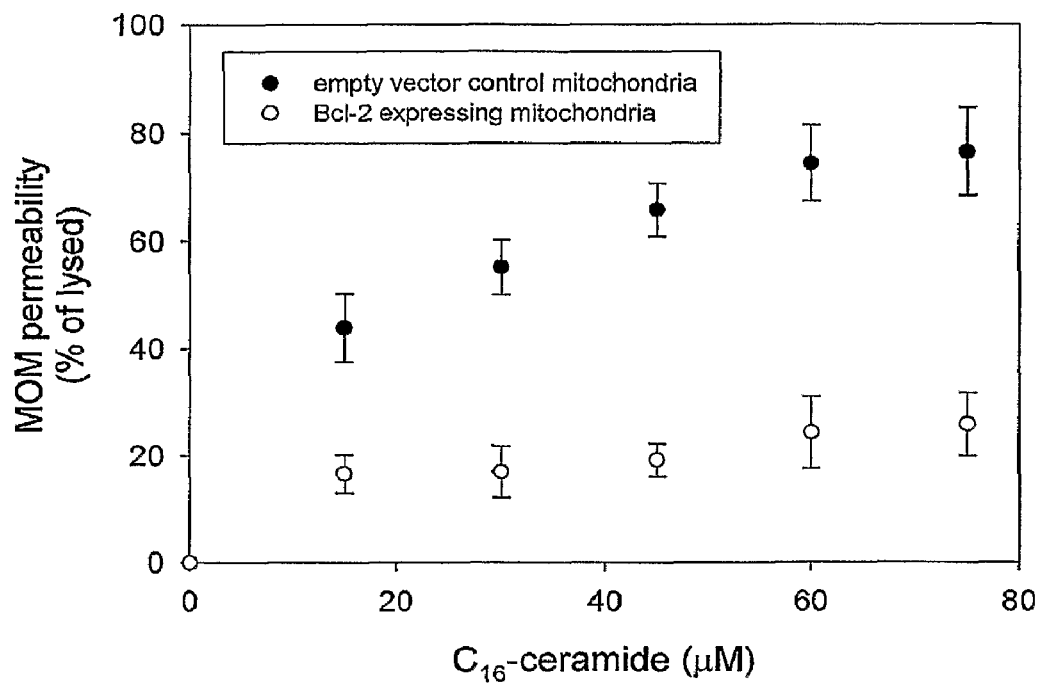
Figure 13D:
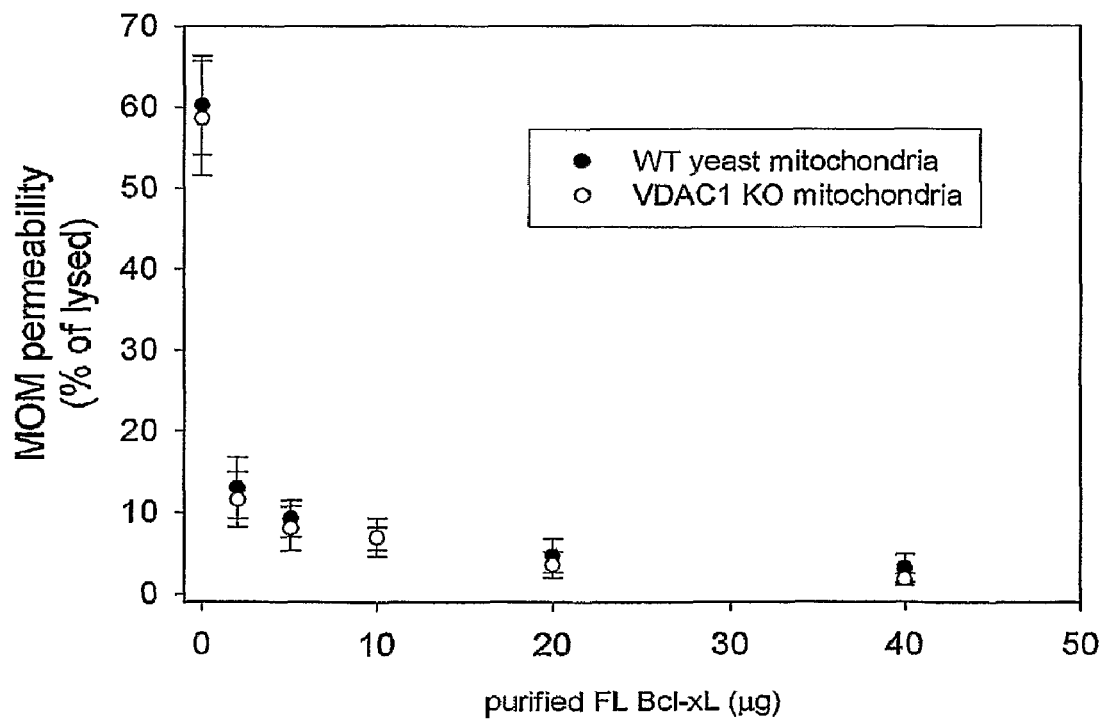
Figure 13E:
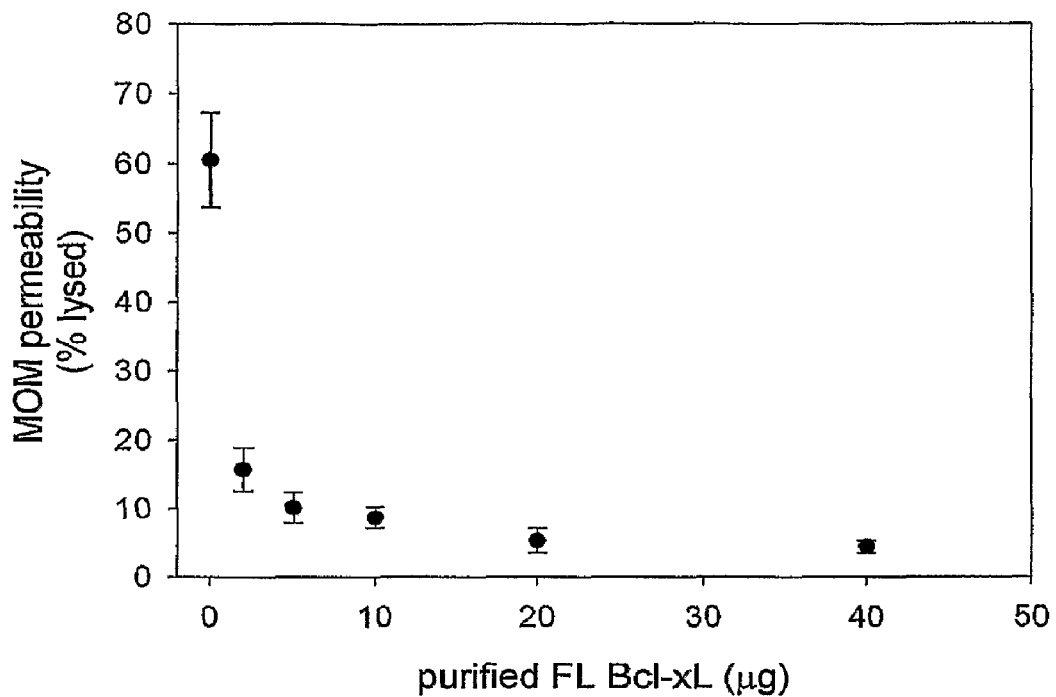
Figure 13F:
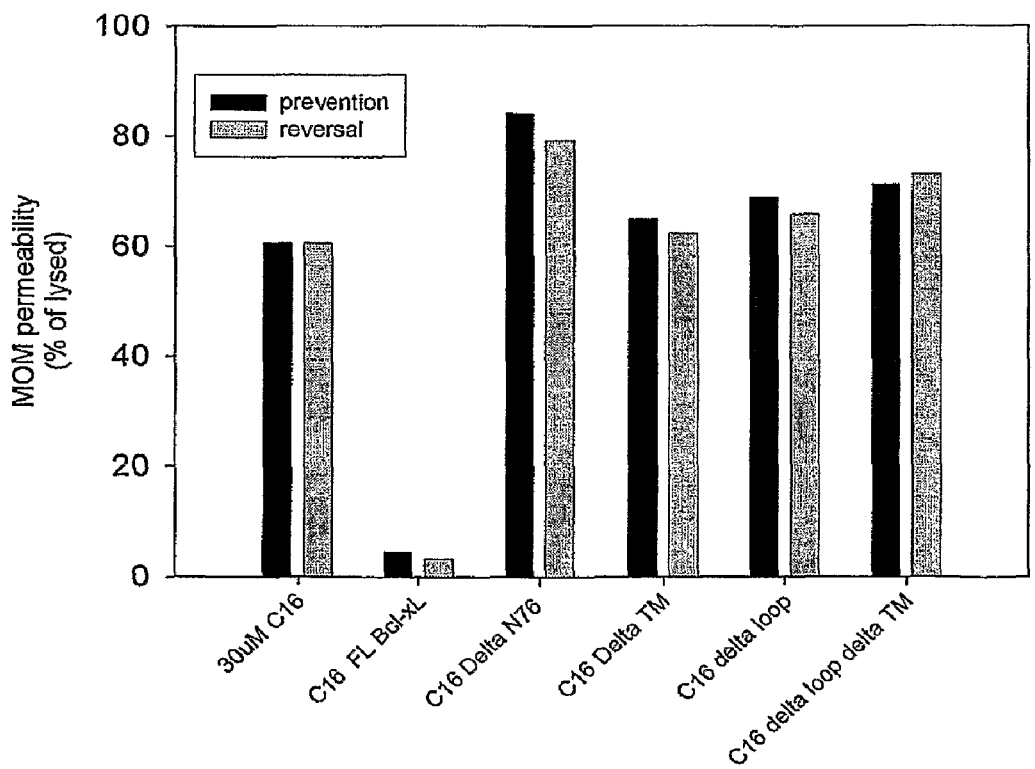

FIGS. 13A-13F show channel formation by $C_{16}$-ceramide in the outer membranes of isolated yeast mitochondria and inhibition by anti-apoptotic Bcl-2 proteins. FIG. 13A shows MOM permeability as a function of $C_{16}$-ceramide concentration for wild-type and VDAC1 deficient sock-out; "KO") yeast mitochondria. Mitochondria (80 µg) isolated from either wild-type (black circles) or VDAC1 KO (open circles) yeast were incubated with the indicated concentrations of $C_{16}$-ceramide for 10 min. The permeability of the MOM to exogenously-added reduced cytochrome c was assessed via the complex IV accessibility assay. Permeability is expressed as a percent of that observed in mitochondria whose outer membranes were lysed via hypotonic shock. Data is the mean of data obtained from three separate mitochondrial preparations and error bars represent the standard deviation. FIG. 13B and FIG. 13C show channel formation by $C_{16}$-ceramide in the outer membranes of isolated yeast mitochondria and inhibition by anti-apoptotic Bcl-2 proteins. FIG. 13B and FIG. 13C shows the results of experiments in which mitochondria were isolated from yeast expressing full length human Bcl-2 or empty vector cells and incubated with $C_{16}$-ceramide for 10 minutes. The permeability of the mitochondrial outer membrane was assessed by the complex IV accessibility assay. Rates are a percentage of the rate of mitochondria with damaged outer membranes. FIG. 13D shows the results of measurements of MOM permeability in isolated WT or VDAC1 KO yeast mitochondria incubated with the indicated amount of full-length Bcl-xL. FIG. 13E shows the effect of full length Bcl-xL on MOM permeability of $C_{16}$-ceramide treated isolated yeast mitochondria. FIG. 13F shows the results of experiments in which isolated wild type (WT) yeast mitochondria were incubated with the indicated treatments for 10 min each in the following order: prevention indicates that the mitochondria were incubated first with 20 µg of the specified protein followed by 20 µM $C_{16}$-ceramide, whereas reversal indicates an incubation with $C_{16}$-ceramide prior to the specified protein. MOM permeability was measured as described herein.

Figure 14:
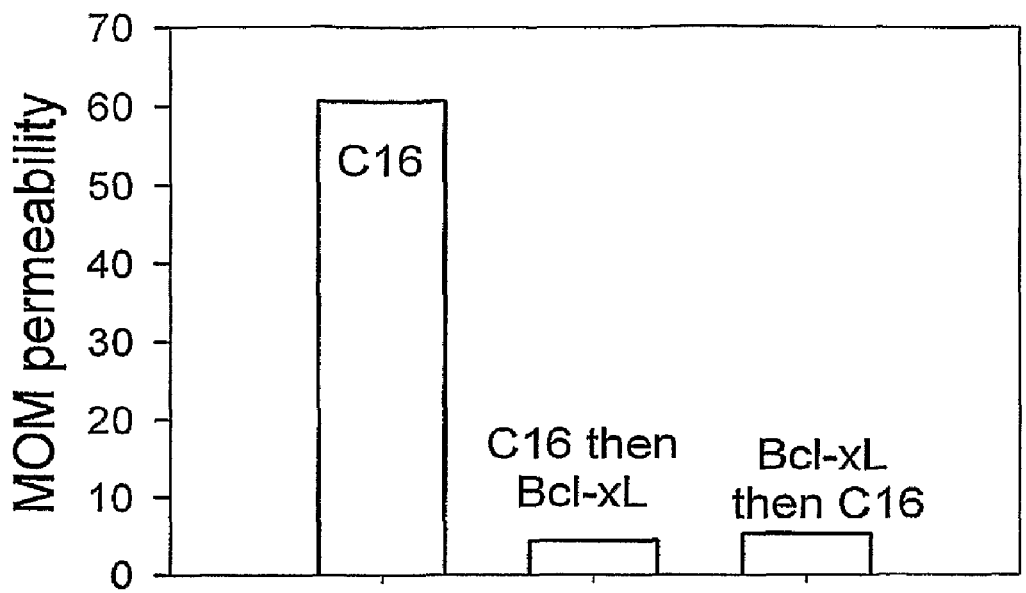

FIG. 14 shows the results of experiments in which isolated wild-type yeast mitochondria were incubated with 30 µM $C_{16}$-ceramide and 10 µg purified recombinant full-length Bcl-xL for 10 minutes where indicated. MOM permeability was assessed via the complex IV accessibility assay. Rates were expressed as a percentage of the rate of mitochondria with damaged MOM.

Figure 15A:
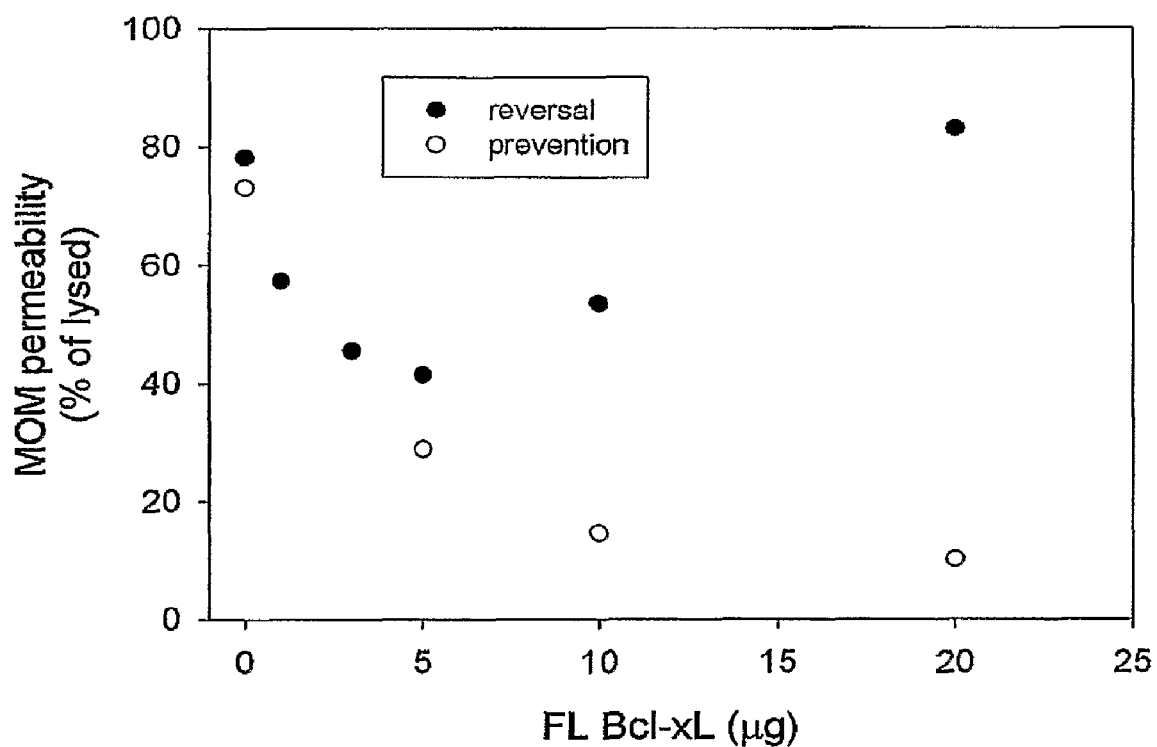
Figure 15B:
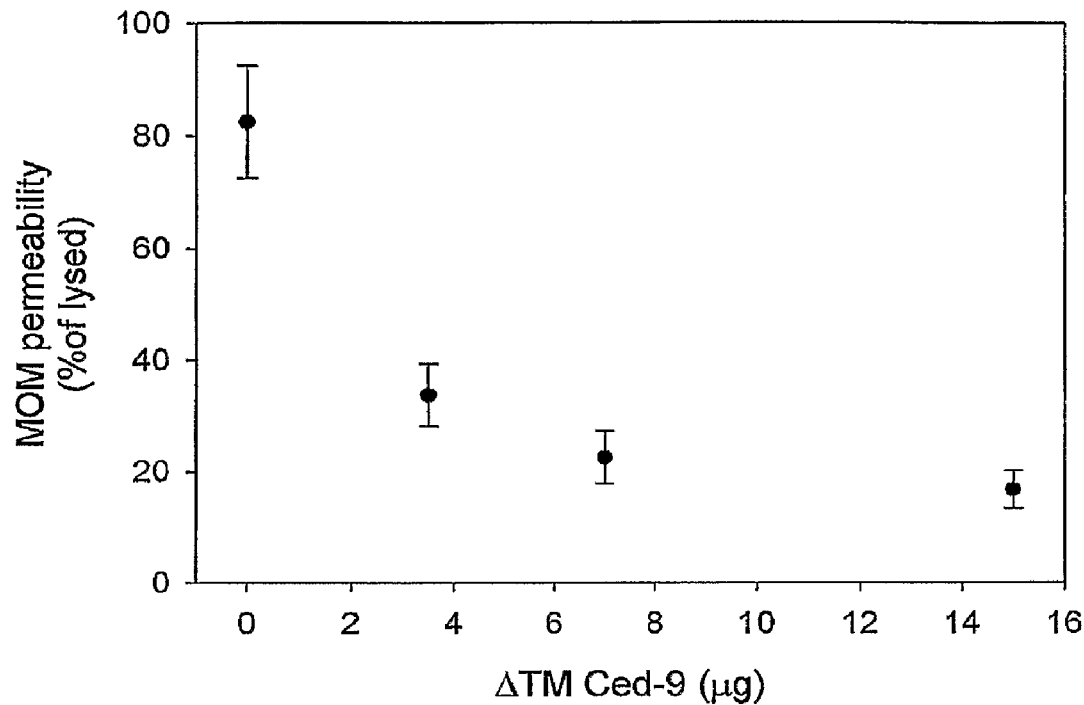

FIG. 15A and FIG. 15B show inhibition of $C_{16}$-ceramide channels by anti-apoptotic Bcl-2 proteins in isolated rat liver mitochondria. FIG. 15A shows the results of experiments in which isolated rat liver mitochondria were incubated separately for 10 minutes each of FL Bcl-xL and 20 µM $C_{16}$-ceramide. Reversal indicates that the $C_{16}$-ceramide incubation occurred prior to the addition of FL Bcl-xL (filled circles). Prevention indicates that the FL Bcl-xL incubation occurred prior to the addition of $C_{16}$-ceramide (open circles). MOM permeability was then measured via the complex IV accessibility assay and expressed as a percentage of the rate measured in mitochondria whose outer membranes were lysed via hypotonic shock. FIG. 15B shows the results of experiments in which isolated rat liver mitochondria were incubated for 10 min with the indicated amounts of purified ΔTM Ced-9 followed by a 10 min incubation with 20 μM $C_{16}$-ceramide. The MOM permeability was measured by measuring the release of adenylate kinase and was expressed as a percent of the release obtained in mitochondria with lysed outer membranes.

Figure 16A:
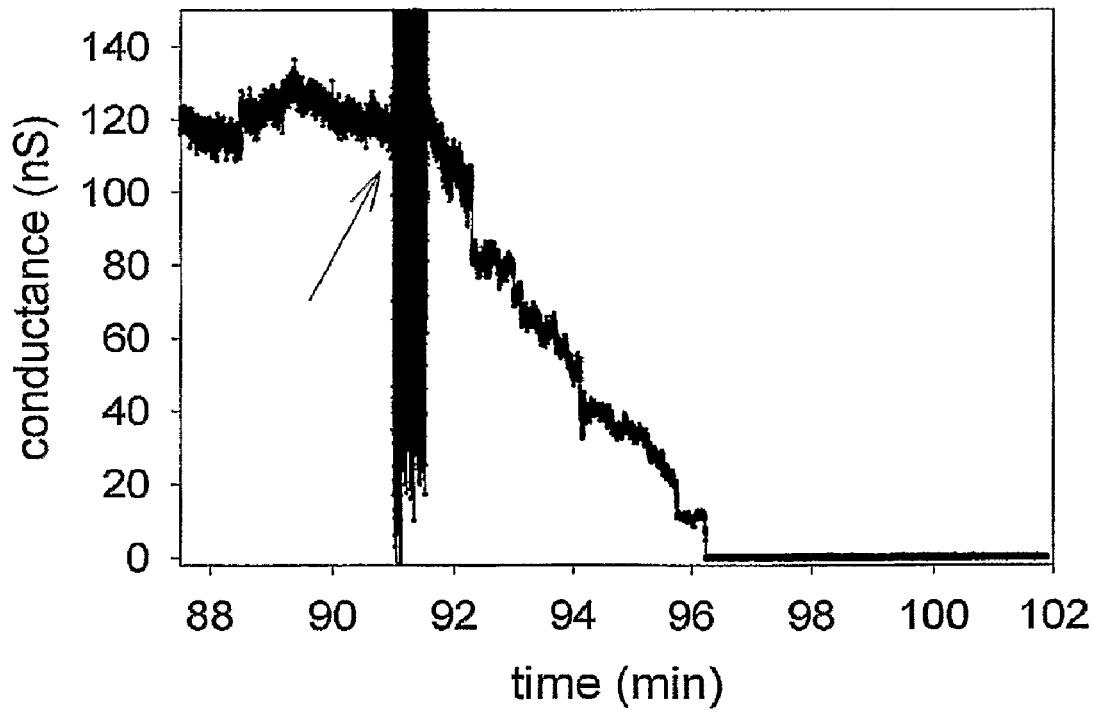
Figure 16B:
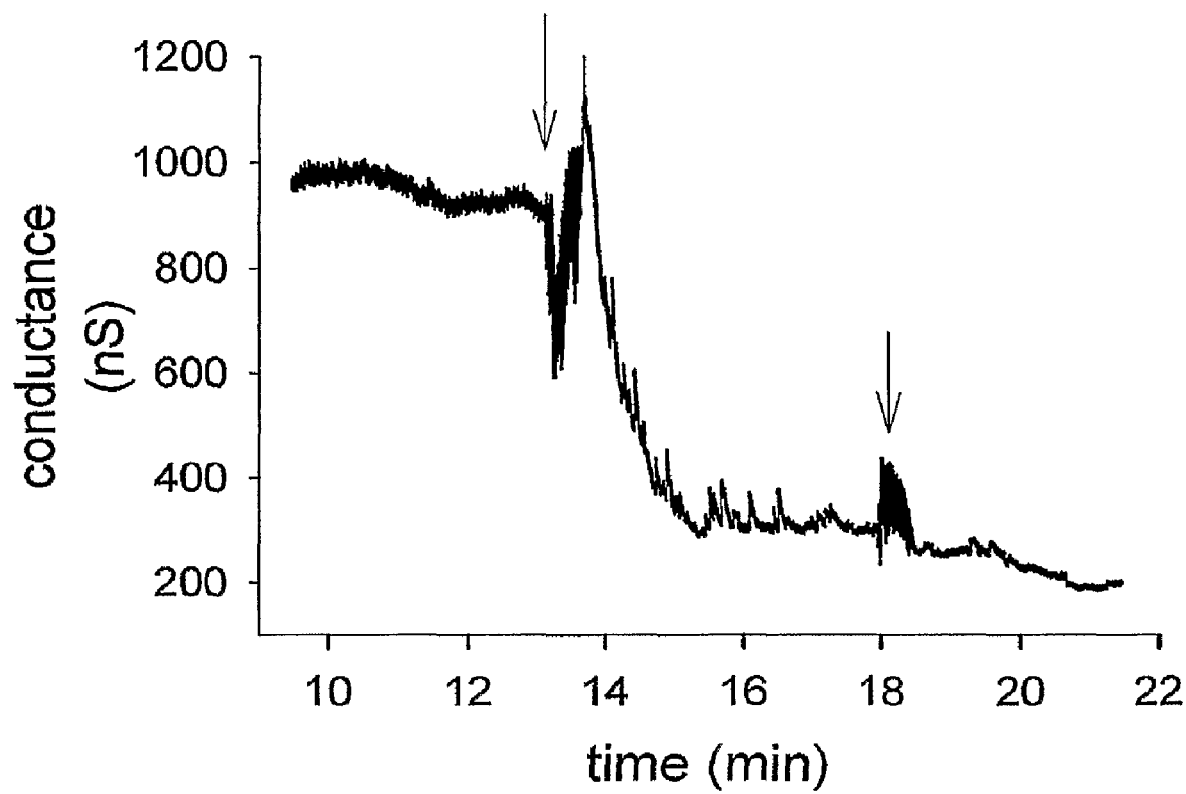

FIG. 16A and FIG. 16B show that $C_{16}$-ceramide channels are inhibited by anti-apoptotic Bcl-2 proteins in the defined system of planar phospholipid membranes. FIG. 16A shows the results of a representative experiment in which $C_{16}$-ceramide was added to the aqueous buffer on the cis side of a planar phospholipid membrane while stirring. Following the ceramide insertion and channel enlargement to a stable conductance state, 0.15 μM FL Bcl-xL was added to both sides of the planar phospholipid membrane while stirring. The current decreased to baseline in a stepwise fashion. FIG. 16B shows the results of a representative experiment in which $C_{16}$-ceramide was added to the aqueous buffer on the cis side of a planar phospholipid membrane while stirring. Following the ceramide insertion and channel enlargement to a stable conductance level, 0.15 μM ΔTM Ced-9 was added the trans side of the planar phospholipid membrane while stirring. The current decreased to baseline in a stepwise fashion.

DESCRIPTION OF THE PREFERRED EMBODIMENTS

The present invention relates to the identification of a novel target for controlling apoptosis, to novel methods for identifying compounds capable of affecting the apoptotic process (i.e., "apoptotic effector compounds"), and to the use of such compounds in the treatment of cancer, stroke, neurodegenerative diseases, viral diseases and other diseases (and conditions) involving apoptosis. The present invention derives in part from the recognition: (1) that cellular apoptosis involves the release of mitochondrial cytochrome c and other compounds; (2) that such release is mediated by ceramide channels that pierce the mitochondrial outer membrane (MOM); (3) and that compounds which assist in the formation or stabilization of such channels can be used to induce apoptosis. Conversely, compounds which inhibit ceramide channel formation or which destabilize such channels can be used to inhibit apoptosis.

Sphingolipids, Ceramides and Ceramide Channels

Sphingolipids are a class of lipids derived from the aliphatic amino alcohol sphingosine. The sphingosine backbone can be O-linked, usually to a charged head group such as choline. The backbone is also amide-linked to an acyl group such as a fatty acid:

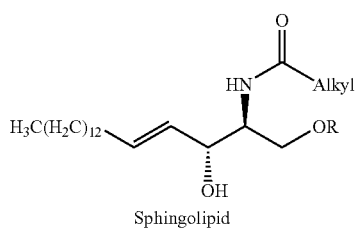

Sphingolipid

Ceramides are a class of sphingolipids in which the R substituent is hydrogen (e.g., N-hexanoyl-D-erythro-sphingosine ($C_{16}$-ceramide), which is a typical naturally occurring long-chain ceramide:

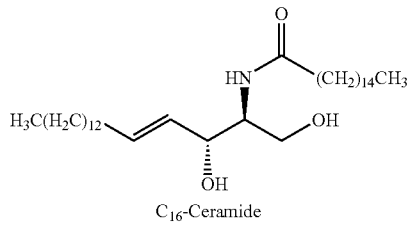

$C_{16}$-Ceramide

Ceramides are found in a variety of cell membranes in organisms ranging from yeast to humans. There are a number of observations that support a proapoptotic role for ceramide in apoptosis:

(1) Ceramide generation is a common cellular response of a variety of cell types following exposure to apoptosis-inducing agents. These include: TNFα (tumor necrosis factor-alpha; Garcia-Ruiz, C. Et al. (1997) "DIRECT EFFECT OF CERAMIDE ON THE MITOCHONDRIAL ELECTRON TRANSPORT CHAIN LEADS TO GENERATION OF REACTIVE OXYGEN SPECIES. ROLE OF MITOCHONDRIAL GLUTATHIONE," J. Biol Chem. 272:11369-11377; Obeid, L. M. et al. (1993) "PROGRAMMED CELL DEATH INDUCED BY CERAMIDE," Science 259:1769-1771; Modur, V. et al. (1996) "ENDOTHELIAL CELL INFLAMMATORY RESPONSES TO TUMOR NECROSIS FACTOR ALPHA. CERAMIDE-DEPENDENT AND INDEPENDENT MITOGEN-ACTIVATED PROTEIN KINASE CASCADES," J. Biol. Chem. 271:13094-13102; Geilen, C. C. et al. (1997) "1 ALPHA, 25-DIHYDROXYVITAMIN D3 INDUCES SPHINGOMYELIN HYDROLYSIS IN HACAT CELLS VIA TUMOR NECROSIS FACTOR ALPHA," J. Biol. Chem. 272:8997-9001); interleukin-1 (Masamune, A. et al. (1996) "REGULATORY ROLE OF CERAMIDE IN INTERLEUKIN (IL)-1 BETA-INDUCED E-SELECTIN EXPRESSION IN HUMAN UMBILICAL VEIN ENDOTHELIAL CELLS. CERAMIDE ENHANCES IL-1 BETA ACTION, BUT IS NOT SUFFICIENT FOR E-SELECTIN EXPRESSION," J. Biol. Chem. 271:9368-9375; Cifone, M. G. et al. (1994) "APOPTOTIC SIGNALING THROUGH CD95 (FAS/APO-1) ACTIVATES AN ACIDIC SPHINGOMYELINASE," J. Exp. Med. 180:1547-1552; Cremesti, A. et al. (2001) "CERAMIDE ENABLES FAS TO CAP AND KILL," J. Biol. Chem. 276:23954-61; Brenner, B. et al. (1998) "FAS/CD95/APO-I ACTIVATES THE ACIDIC SPHINGOMYELINASE VIA CASPASES," Cell Death Differ. 5:29-37; Gulbins, E. et al. (1995) "FAS-INDUCED APOPTOSIS IS MEDIATED VIA A CERAMIDE-INITIATED RAS SIGNALING PATHWAY," Immunity 2:341-351; Paris, F. et al. (2001) "NATURAL CERAMIDE REVERSES FAS RESISTANCE OF ACID SPHINGOMYELINASE (−/−) HEPATOCYTES," J. Biol. Chem. 276, 8297-8305; Tepper, A. D. et al. (1999) "ORDERING OF CERAMIDE FORMATION, CASPASE ACTIVATION, AND MITOCHONDRIAL CHANGES DURING CD95- AND DNA DAMAGE-INDUCED APOPTOSIS," J. Clin. Invest. 103:971-978; Birbes, H. et al. (2002) "MITOCHONDRIA AND CERAMIDE: INTERTWINED ROLES IN REGULATION OF APOPTOSIS," Advan. Enzyme Regul. 42:113-129); Nitrous Oxide (Takeda, Y. et al. (1999) "CERAMIDE GENERATION IN NITRIC OXIDE-INDUCED APOPTOSIS. ACTIVATION OF MAGNESIUM-DEPENDENT NEUTRAL SPHINGOMYELINASE VIA CASPASE-3," J. Biol. Chem. 274:10654-10660); Ionizing Radiation (Vit, J. P. et al. (2003) "ROLE OF THE CERAMIDE-SIGNALING PATHWAYS IN IONIZING RADIATION-INDUCED APOPTOSIS," Oncogene 22:8645-8652; Alphonse, G. et al. (2002) "CERAMIDE INDUCES ACTIVATION OF THE MITOCHONDRIAL/ CASPASES PATHWAY IN JURKAT AND SCC61 CELLS SENSITIVE TO Gamma-Radiation But Activation Of This Sequence Is Defective In Radioresistant SQ20B Cells," Int J Radiat Biol. 78:821-835); Serum Withdrawal (Caricchio, R. et al. (2002) "Fas, Ceramide And Serum Withdrawal Induce Apoptosis Via A Common Pathway In A Type II Jurkat Cell Line," Cell Death Differ. 9:574-580)); Heat (Jenkins, G. M. (2003) "The Emerging Role For Sphingolipids In The Eukaryotic Heat Shock Response," Cell Mol. Life Sci. 60:701-710)); Etoposide (Sawada M. et al. (2000) "Ordering Of Ceramide Formation, Caspase Activation, And Bax/Bcl-2 Expression During Etoposide-Induced Apoptosis In C6 Glioma Cells," Cell Death Differ. 7:761-772); Staurosporine (Wiesner, D. A. et al. (1996) "Staurosporine Induces Programmed Cell Death In Embryonic Neurons And Activation Of The Ceramide Pathway," J. Neurochem. 66:1418-1425); Daunorubicin (Come, M. G. et al. (1999) "Alteration Of The Daunorubicin-Triggered Sphingomyelin-Ceramide Pathway And Apoptosis In MDR Cells: Influence Of Drug Transport Abnormalities," Int. J. Cancer. 81:580-587); and the corticosteroid Dexamethasone (Cifone, M. G. et al. (1999) "Dexamethasone-Induced Thymocyte Apoptosis: Apoptotic Signal Involves The Sequential Activation Of Phosphoinositide-Specific Phospholipase C, Acidic Sphingomyelinase, And Caspases," Blood 93, 2282-96);

2. The effective doses of these agents required to induce ceramide generation closely matches the dose required to induce apoptosis (Kolesnick, R. N. et al. (1998) "Regulation Of Ceramide Production And Apoptosis," Annu. Rev. Physiol. 60:643-665);

3. Elevations in cellular ceramide in response to these agents occurs prior to the execution phase of apoptosis (Birbes, H. et al. (2002) "Mitochondria And Ceramide: Intertwined Roles In Regulation Of Apoptosis," Advan. Enzyme Regul. 42:113-129; Hannun, Y. A. (1996) "Functions Of Ceramide In Coordinating Cellular Responses To Stress," Science 274:1855-1859; Dbaibo, G. S. et al. (1997) "Cytokine Response Modifier A (CRMA) Inhibits Ceramide Formation In Response To Tumor Necrosis Factor (TNF)-Alpha: CRMA And BCL-2 Target Distinct Components In The Apoptotic Pathway," J Exp Med. 185:481-490);

4. Exogenous addition of cell-permeable ceramide analogues induces apoptosis in a variety of cell lines (for example, Cifone, M. G. et al. (1994) "Apoptotic Signaling Through CD95 (Fas/Apo-1) Activates An Acidic Sphingomyelinase," J. Exp. Med. 180:1547-1552; Jarvis, W. D. et al. (1994) "Induction Of Apoptotic DNA Damage And Cell Death By Activation Of The Sphingomyelin Pathway," Proc. Natl. Acad. Sci. U.S.A. 91:73-77; Obeid, L. M. et al. (1993) "Programmed Cell Death Induced By Ceramide," Science 259:1769-1771; Quintans, J. et al. (1994) "Ceramide Mediates The Apoptotic Response Of Wehi 231 Cells To Anti-Immunoglobulin, Corticosteroids And Irradiation," Biochem. Biophys. Res. Commun. 202:710-714);

5. Ceramide-induced apoptosis is very specific as the naturally occurring ceramide precursor dihydroceramide (lacks the 4-5 trans double bond present in ceramide) does not induce apoptosis (Obeid, L. M. et al. (1993) "Programmed Cell Death Induced By Ceramide," Science 259: 1769-1771) nor form channels in membranes (Siskind, L. J. et al. (2000) "The Lipids $C_2$- And $C_{16}$-Ceramide Form Large Stable Channels In Membranes: Implications For Apoptosis," J. Biol. Chem. 275:39640-39644); and 6. Apoptosis can be inhibited upon blockage of ceramide generation and cells that are incapable of generating ceramide are often incapable of undergoing apoptosis (Selzner, M. et al. (2001) "Induction Of Apoptotic Cell Death And Prevention Of Tumor Growth By Ceramide Analogues In Metastatic Human Colon Cancer," Cancer Res. 61:1233-1240; Alphonse, G. et al. (2004) "Overcoming Resistance To Gamma-Rays In Squamous Carcinoma Cells By Poly-Drug Elevation Of Ceramide Levels," Oncogene 23:2703-2715; Chmura, S. J. et al. (1997) "Loss Of Ceramide Production Confers Resistance To Radiation-Induced Apoptosis," Cancer Res. 57, 1270-1275; Chmura, S. J. et al. (1997) "Decreasing The Apoptotic Threshold Of Tumor Cells Through Protein Kinase C Inhibition And Sphingomyelinase Activation Increases Tumor Killing By Ionizing Radiation," Cancer Res. 57:4340-4347; Bruno, A. P. et al. (1998) "Lack Of Ceramide Generation In TF-1 Human Myeloid Leukemic Cells Resistant To Ionizing Radiation," Cell Death Differ. 5:172-182; Sautin, Y. et al. (2000) "Ceramide-Induced Apoptosis Of Human Thyroid Cancer Cells Resistant To Apoptosis By Irradiation," Thyroid 10:733-740; Riboni, L. et al. (2002) "Ceramide Levels Are Inversely Associated With Malignant Progression Of Human Glial Tumors," Glia 39:105-113).

There is accumulating evidence that ceramide is involved in neuronal cell death. In primary neuronal cell cultures, exogenous ceramide causes dose-dependent apoptotic cell death and ceramide levels are increased after various apoptotic stimuli (Lambeng, N. et al. (1999) "Mechanisms Of Apoptosis In PC12 Cells Irreversibly Differentiated With Nerve Growth Factor And Cyclic AMP," Brain Res. 821:60-68; Movsesyan, V. A. et al. (2002) "Ceramide Induces Neuronal Apoptosis Through The Caspase-9/Caspase-3 Pathway," Biochem. Biophys. Res. Commun. 299:201-207; Stoica, S. C. et al. (2003) "Heat Shock Protein, Inducible Nitric Oxide Synthase And Apoptotic Markers In The Acute Phase Of Human Cardiac Transplantation," Eur. J. Cardiothorac. Surg. 24:932-939; Taniwaki, T. et al. (1999) "Ceramide Induces Apoptosis To Immature Cerebellar Granule Cells In Culture," Neurochem Res. 24:685-690; Toman, R. E. et al. (2002) "Ceramide-Induced Cell Death In Primary Neuronal Cultures: Upregulation Of Ceramide Levels During Neuronal Apoptosis," J. Neurosci. Res. 68:323-330; and Willaime-Morawek, S. et al. (2005) "IGF-I Protects Cortical Neurons Against Ceramide-Induced Apoptosis Via Activation Of The PI-3K/AKT And ERK Pathways; Is This Protection Independent Of CREB And BCL-2"? Brain Res Mol Brain Res. 142:97-106). Ceramide has been shown to be involved in neuronal death during development (Bieberich, E. et al. (2003) "Regulation Of Cell Death In Mitotic Neural Progenitor Cells By Asymmetric Distribution Of Prostate Apoptosis Response 4 (PAR-4) And Simultaneous Elevation Of Endogenous Ceramide," J. Cell Biol. 162:469-479), as well as in models of acute or chronic neurodegenerative disorders such as cerebral ischemia (Nakane, M. et al. (2000) "Lethal Forebrain Ischemia Stimulates Sphingomyelin Hydrolysis And Ceramide Generation In The Gerbil Hippocampus," Neurosci Lett. 296:89-92), and Alzheimer's disease ("AD;" Lee, J. T. et al. (2004) "Amyloid-Beta Peptide Induces Oligodendrocyte Death By Activating The Neutral Sphingomyelinase-Ceramide Pathway," J. Cell Biol. 164:123-131; Han, X. M. et al. (2002) "Substantial Sulfatide Deficiency And Ceramide Elevation In Very Early Alzheimer's Disease: Potential Role In Disease Pathogenesis," J. Neurochem. 82:809-818; Gupta, A. et al. (2003) "Inflammation And Alzheimer's Disease," Int. J. Clin. Pract. 57:36-39). For example, transient focal cerebral ischemia induces large increases in acid sphingomyelinase activity (aSMase), ceramide levels and production of inflammatory cytokines in wild-type mice; mice deficient in aSMase or inhibition of ceramide production in wild-type mice with an aSMase inhibitor significantly reduced ischemic neuronal injury and improved behavioral outcome. Similarly, in CSF and brain tissue astroglia obtained from AD patients, there are increased levels of ceramide as well as the increase of intra- and extracellular ceramide levels in retinoic acid (RA)-induced neuronal apoptosis (Satoi, H. et al. (2005) "ASTROGLIAL EXPRESSION OF CERAMIDE IN ALZHEIMER'S DISEASE BRAINS: A ROLE DURING NEURONAL APOPTOSIS," Neuroscience 130:657-666). Cutler et al. (2004) ("INVOLVEMENT OF OXIDATIVE STRESS-INDUCED ABNORMALITIES IN CERAMIDE AND CHOLESTEROL METABOLISM IN BRAIN AGING AND ALZHEIMER'S DISEASE," Proc. Natl. Acad. Sci. USA 101(7):2070-2075) documented significant increases in levels of long-chain ceramides in brain cells during normal aging in mice, in AD patients, and in neurons exposed to Aβ and this intracellular accumulation of ceramides and the neurotoxicity of Aβ were blocked by an inhibitor of ceramide production. Studies have established a role for mitochondria specifically in ceramide-induced neuronal cell death. For example, mitochondrial depolarization and permeabilization occur after ceramide exposure (Stoica, S. C. et al. (2003) "HEAT SHOCK PROTEIN, INDUCIBLE NITRIC OXIDE SYNTHASE AND APOPTOTIC MARKERS IN THE ACUTE PHASE OF HUMAN CARDIAC TRANSPLANTATION," Eur. J. Cardiothorac. Surg. 24:932-939) and lead to activation of the intrinsic caspase cascade pathway (Movsesyan, V. A. et al. (2002) "CERAMIDE INDUCES NEURONAL APOPTOSIS THROUGH THE CASPASE-9/CASPASE-3 PATHWAY," Biochem. Biophys. Res. Commun. 299:201-207).

The addition of ceramide to isolated mitochondria results in the release of cytochrome c, apoptosis-inducing factor AIF, AK-2, and adenylate kinase (Siskind, L. J. et al. (2002) "CERAMIDE CHANNELS INCREASE THE PERMEABILITY OF THE MITOCHONDRIAL OUTER MEMBRANE TO SMALL PROTEINS," J. Biol. Chem. 277:26796-26803; Arora, A. S. et al. (1997) "CERAMIDE INDUCES HEPATOCYTE CELL DEATH THROUGH DISRUPTION OF MITOCHONDRIAL FUNCTION IN THE RAT," Hepatology 25:958-963; Ghafourifar, P. et al. (1999) "CERAMIDE INDUCES CYTOCHROME C RELEASE FROM ISOLATED MITOCHONDRIA. IMPORTANCE OF MITOCHONDRIAL REDOX STATE," J. Biol. Chem. 274:6080-6084; Di Paola, M. et al. (2000) "CERAMIDE INTERACTION WITH THE RESPIRATORY CHAIN OF HEART MITOCHONDRIA," Biochemistry 39:6660-6668; Di Paola, M. et al. (2004) "CERAMIDE INDUCES RELEASE OF PRO-APOPTOTIC PROTEINS FROM MITOCHONDRIA BY EITHER A CA2+-DEPENDENT OR A CA2+-INDEPENDENT MECHANISM," J. Bioenerg. Biomembr. 36:165-170). Both the short-chain model compound, N-acetyl-D-erythro-sphingosine ($C_2$-ceramide):

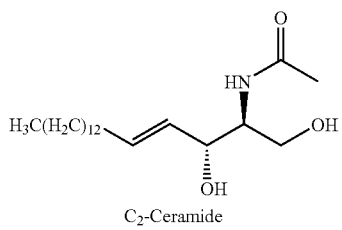
$C_2$-Ceramide and the naturally occurring N-hexanoyl-D-erythro-sphingosine ($C_{16}$-ceramide) discussed above, release these proteins.

The mechanism of this release is most likely the formation of large channels in the mitochondrial outer membrane (MOM) since a whole range of intermembrane space proteins are released up to a molecular mass cutoff of 60 kDa (Siskind, L. J. et al. (2002) "CERAMIDE CHANNELS INCREASE THE PERMEABILITY OF THE MITOCHONDRIAL OUTER MEMBRANE TO SMALL PROTEINS," J. Biol. Chem. 277:26796-26803). The exact nature of these large channels is unknown but the same ceramides form large channels >10 nm in diameter in phospholipids membranes lacking any proteins demonstrating that these lipids are sufficient, but other components are likely to be involved. The properties of ceramide channels are consistent with a barrel-stave structure (Siskind, L. J. et al. (2000) "THE LIPIDS $C_2$- AND $C_{16}$-CERAMIDE FORM LARGE STABLE CHANNELS. IMPLICATIONS FOR APOPTOSIS," J. Biol. Chem. 275:38640-38644; Siskind, L. J. et al. (2003) "ENLARGEMENT AND CONTRACTURE OF $C_2$-CERAMIDE CHANNELS," Biophys. J. 85:1560-1575).

The structurally related lipid, sphingosine:

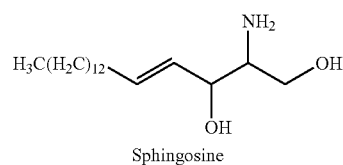
Sphingosine has also been shown to induce apoptosis (Cuvillier, O. et al. (2000) "INVOLVEMENT OF SPHINGOSINE IN MITOCHONDRIA-DEPENDENT FAS-INDUCED APOPTOSIS OF TYPE II JURKAT T CELLS," J. Biol. Chem. 275:15691-15700; Cuvillier, O. et al. (2001) "SPHINGOSINE GENERATION, CYTOCHROME C RELEASE, AND ACTIVATION OF CASPASE-7 IN DOXORUBICIN-INDUCED APOPTOSIS OF MCF7 BREAST ADENOCARCINOMA CELLS," Cell Death Differ. 8:162-171; Cuvillier, O. (2002) "SPHINGOSINE IN APOPTOSIS SIGNALING," Biochim. Biophys. Acta. 1585:153-162; Jarvis, W. D. et al. (1996) "INDUCTION OF APOPTOSIS AND POTENTIATION OF CERAMIDE-MEDIATED CYTOTOXICITY BY SPHINGOID BASES IN HUMAN MYELOID LEUKEMIA CELLS," J. Biol. Chem. 271:8275-8284; Sweeney, E. A. et al. (1998) "INHIBITION OF SPHINGOLIPID INDUCED APOPTOSIS BY CASPASE INHIBITORS INDICATES THAT SPHINGOSINE ACTS IN AN EARLIER PART OF THE APOPTOTIC PATHWAY THAN CERAMIDE," FEBS Lett. 425:61-65; Hung, W.-C. et al. (1999) "ACTIVATION OF CASPASE-3-LIKE PROTEASES IN APOPTOSIS INDUCED BY SPHINGOSINE AND OTHER LONG-CHAIN BASES IN HEP3B HEPATOMA CELLS," Biochem. J. 338:161-166).

The channels formed by ceramides in planar phospholipid and mitochondrial outer membranes are both large and sufficiently stable to mediate a regulatory function in apoptosis, including the release of cytochrome c and other proapoptotic factors from the mitochondrial intermembrane space (Siskind, L. J. (2005) "MITOCHONDRIAL CERAMIDE AND THE INDUCTION OF APOPTOSIS," J. Bioenerg. Biomem. 37:143-153; Siskind, L. J. et al. (2000) "THE LIPIDS $C_2$- AND $C_{16}$-CERAMIDE FORM LARGE STABLE CHANNELS IN MEMBRANES. IMPLICATIONS FOR APOPTOSIS," J. Biol. Chem. 275:39640-39644; Siskind, L. J. et al. (2003) "ENLARGEMENT AND CONTRACTURE OF $C_2$-CERAMIDE CHANNELS," Biophys. J. 85:1560-1575; Siskind, L. J. et al. (2005) "SPHINGOSINE FORMS CHANNELS IN MEMBRANES THAT DIFFER GREATLY FROM THOSE FORMED BY CERAMIDE," J. Bioenerg. Biomembr. 37:227-236; Siskind, L. J. et al. (2002) "CERAMIDE CHANNELS INCREASE THE PERMEABILITY OF THE MITOCHONDRIAL OUTER MEMBRANE TO SMALL PROTEINS," J. Biol. Chem. 277:26796-26803). The channels have estimated diameters of between 6 and 10 nm and open channel lifetimes of several minutes (Siskind, L. J. et al. (2002) "CERAMIDE CHANNELS INCREASE THE PERMEABILITY OF THE MITOCHONDRIAL OUTER MEMBRANE TO SMALL PROTEINS," J. Biol. Chem. 277:26796-26803; Siskind, L. J. et al. (2003) "ENLARGEMENT AND CONTRACTURE OF $C_2$-CERAMIDE CHANNELS," Biophys. J. 85:1560-1575; Siskind, L. J. et al. (2006) "CERAMIDE FORMS CHANNELS IN MITOCHON- DRIAL OUTER MEMBRANES AT PHYSIOLOGICALLY RELEVANT CONCENTRATIONS," Mitochondrion 6(3):118-125). Such attributes are extremely remarkable given that the channel structure is comprised of hundreds of ceramide monomers held together via a hydrogen bonded network lining the channel lumen (Siskind, L. J. et al. (2003) "ENLARGEMENT AND CONTRACTURE OF $C_2$-CERAMIDE CHANNELS," Biophys. J. 85:1560-1575; Anishkin, A. et al. (2006) "SEARCHING FOR THE MOLECULAR ARRANGEMENT OF TRANSMEMBRANE CERAMIDE CHANNELS," Biophys. J. 90:2414-2426). Even more remarkable is the recognition that these channels comprise a pathway through which proapoptotic proteins are released from mitochondria during the induction phase of apoptosis (Si skind, L. J. et al. (2005) "SPHINGOSINE FORMS CHANNELS IN MEMBRANES THAT DIFFER GREATLY FROM THOSE FORMED BY CERAMIDE," J. Bioenerg. Biomembr. 37:227-236).

Figure 1A:
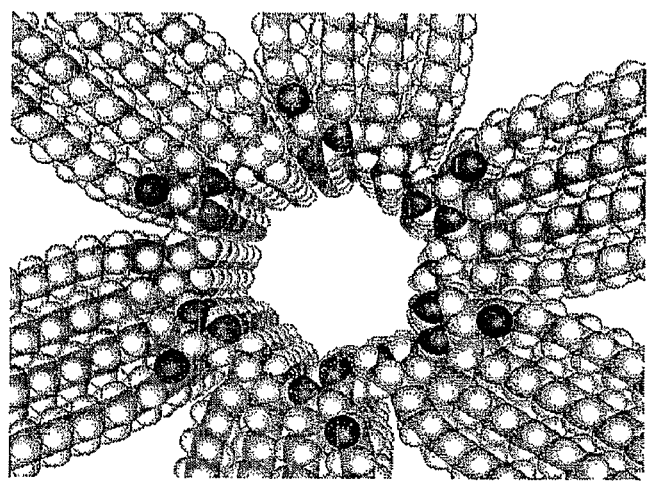
FIG. 1A shows a representation of a top-down view of a ceramide channel in the mitochondrial outer membrane.
Figure 1B:
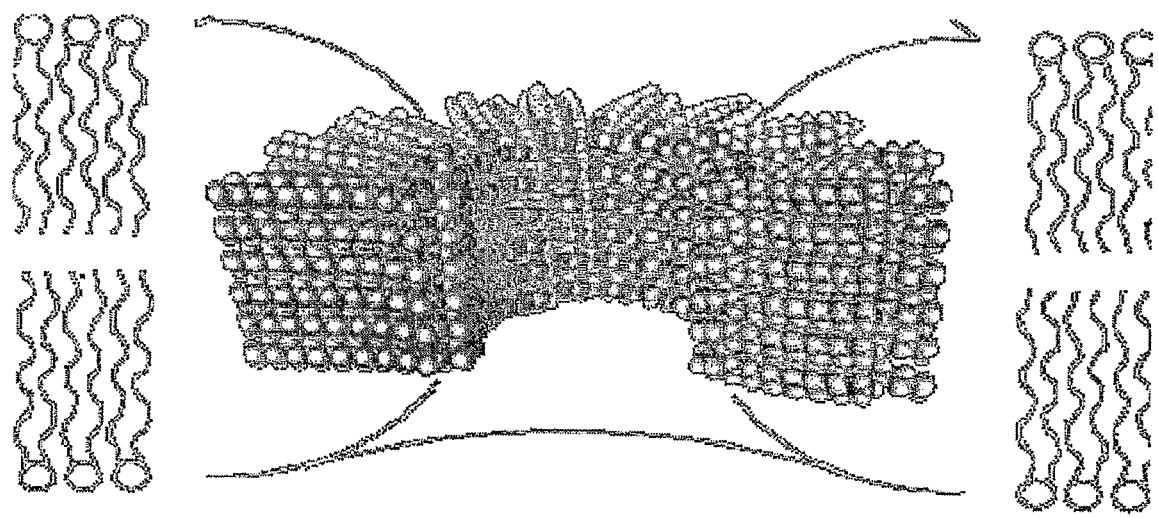
FIG. 1B shows a representation of a cross-sectional view of a ceramide channel in the mitochondrial outer membrane.

FIG. 1A and FIG. 1B illustrate the appearance of the ceramide channels. Significantly, the ceramide channels enlarge and contract in a dynamic fashion and thus form barrel-stave channels that are stable over a simulation of 10 nsec. The channels are in the shape of rigid cylinders; they are not defects in the membrane but organized channels (Siskind, L. J. et al. (2003) "ENLARGEMENT AND CONTRACTURE OF $C_2$-CERAMIDE CHANNELS," Biophys. J. 85:1560-1575; Siskind, L. J. et al. (2005) "SPHINGOSINE FORMS CHANNELS IN MEMBRANES THAT DIFFER GREATLY FROM THOSE FORMED BY CERAMIDE," J. Bioenerg. Biomembr. 37:227-236). The structure of individual ceramides in the channel assembly simultaneously generate 2 curvatures at the water/membrane interface: one negative in the x-y plane of the membrane allowing the ceramide to form a cylindrical structure and one positive in the z direction (normal to the plane of the membrane) allowing the channel to interface with the phospholipids, forming a continuous polar surface at the water interface. The trans double bond caused the acyl chains to be more rigid near the polar region allowing the tails to be compact and thus occupy less space in the z direction than the polar groups resulting in the aforementioned positive curvature.

Consistent with such conclusions is the observation that the ceramide channels can disassemble in a way which results in large conductance decrements that are multiples of 4.0 nS. Since a cylindrical channel with a large diameter will have a conductance that is proportional to its circumference (due to the access resistance), such conductance decrements strongly indicate that the disassembly involves multiples of 2 ceramide columns forming the wall of the channel. Without intending to limit the present invention, it is believed that the columns respond as pairs because they are aligned in an antiparallel fashion and held together by the attraction of dipoles (arising from the oriented amide linkages) oriented in opposite directions.

Bolstering the conclusion that channels formed in the MOM are composed of ceramide molecules as opposed to ceramide merely acting as a trigger for the formation of another pore was the observation that the impermeability of the MOM to proteins could be restored by removing ceramide. Fatty-acid-depleted albumin effectively reversed the permeabilization of the MOM by short-chain ceramide. Albumin binds this form of ceramide and thus the reversal indicates a dynamic equilibrium between ceramides in the channel with the rest of the ceramide in the membrane and, when ceramide is removed by binding to the albumin, the channels disassemble (Siskind, L. J. et al. (2002) "CERAMIDE CHANNELS INCREASE THE PERMEABILITY OF THE MITOCHONDRIAL OUTER MEMBRANE TO SMALL PROTEINS," J. Biol. Chem. 277:26796-26803). The fact that the same result was not achieved with $C_{16}$-ceramide is understandable due to the exceedingly low aqueous solubility of long-chain ceramide. In many respects, $C_2$-ceramide and $C_{16}$-ceramide behave similarly. For example, the permeabilization of the MOM was remarkably similar whether $C_2$-ceramide or $C_{16}$-ceramide was used in the experiment (Siskind, L. J. et al. (2002) "CERAMIDE CHANNELS INCREASE THE PERMEABILITY OF THE MITOCHONDRIAL OUTER MEMBRANE TO SMALL PROTEINS," J. Biol. Chem. 277:26796-26803).

Evidence of physiological relevance can be seen in the finding that ceramide levels become elevated early in the apoptotic process. Moreover, in MOMs, the ceramide channels have been found to be able to release proteins as large as 60 kDa from the intermembrane space. This cut-off is significant because it is in line with the size of proapoptotic proteins that are released from mitochondria during the induction phase of apoptosis. Ceramide channel formation in MOMs requires only 2 to 4 pmoles of ceramide per nmole mitochondrial phospholipids (Siskind, L. J. (2005) "MITOCHONDRIAL CERAMIDE AND THE INDUCTION OF APOPTOSIS," J. Bioenerg. Biomem. 37:143-153). A typical ceramide level at the early stages of apoptosis is 4 pmol ceramide/nmole phospholipids. At this molar ratio, ceramide effectively permeabilizes the outer membrane to cytochrome c (Siskind, L. J. et al. (2006) "CERAMIDE FORMS CHANNELS IN MITOCHONDRIAL OUTER MEMBRANES AT PHYSIOLOGICALLY RELEVANT CONCENTRATIONS," Mitochondrion 6(3):118-125). This level of ceramide is on the order of the level of mitochondrial ceramide increase found during the induction phase of apoptosis (before or at the time of cytochrome c release. Mitochondrial ceramide levels have been found to increase by about 6.5 pmol ceramide/nmol phospholipid in MCF7 cells treated with TNFα (Birbes, H. et al. (2005) "A MITOCHONDRIAL POOL OF SPHINGOMYELIN IS INVOLVED IN TNFALPHA-INDUCED BAX TRANSLOCATION TO MITOCHONDRIA," Biochem. J. 386:445-451). Garcia-Ruiz et al. (1997) ("DIRECT EFFECT OF CERAMIDE ON THE MITOCHONDRIAL ELECTRON TRANSPORT CHAIN LEADS TO GENERATION OF REACTIVE OXYGEN SPECIES. ROLE OF MITOCHONDRIAL GLUTATHIONE," J. Biol. Chem. 272:11369-11377) reported a similar increase in isolated mitochondria from TNF treated hepatocytes (an increase of about 4.5 pmol ceramide/nmole phospholipid). γ-radiation of Jurkat cells induced the formation of 4 pmol mitochondrial ceramide per mmole phospholipid (Rodriguez-Lafrasse, C. et al. (2002) "INCREASING ENDOGENOUS CERAMIDE USING INHIBITORS OF SPHINGOLIPID METABOLISM MAXIMIZES IONIZING RADIATION-INDUCED MITOCHONDRIAL INJURY AND APOPTOTIC CELL KILLING," Int. J. Cancer 101:589-598). Thus controlling the rate of ceramide synthesis, ceramide hydrolysis, ceramide delivery to mitochondria, or the propensity for ceramide channel formation may all be ways to control the onset of mitochondria-mediated apoptosis and thus treat a variety of diseases. Finally, the enzymes catalyzing the metabolic pathways leading to both ceramide synthesis and breakdown are known to be present in mitochondria (El Bawab, S. et al. (2000) "MOLECULAR CLONING AND CHARACTERIZATION OF A HUMAN MITOCHONDRIAL CERAMIDASE," J. Biol. Chem. 275:21508-21513; Shimeno, H. et al. (1998) "PARTIAL PURIFICATION AND CHARACTERIZATION OF SPHINGOSINE N-ACYLTRANSFERASE CERAMIDE SYNTHASE FROM BOVINE LIVER MITOCHONDRION-RICH FRACTION," Lipids 33:601-605; Bionda, C. et al. (2004) "SUBCELLULAR COMPARTMENTALIZATION OF CERAMIDE METABOLISM: MAM (MITOCHONDRIA-ASSOCIATED MEMBRANE AND/OR MITOCHONDRIA"? Biochem. J. 382:527-533). Taken together, these facts indicate that the ceramide channel is the permeability pathway through the mitochondrial outer membrane for protein flux.

In contrast, significantly higher ceramide:phospholipids ratios are needed to permeabilize the cell's plasma membranes (e.g., a 20 fold higher ratio is needed to permeabilize an erythrocyte membrane). Thus ceramide channel formation shows high specificity for the MOM. The specificity is not due to differential partitioning of ceramide in these membranes, but to intrinsic differences between these membranes. The high concentration of ceramide required for formation of channels in planar phospholipid membranes, such as erythrocyte membranes, suggests that such membranes contain an inhibitor which inhibits the formation of ceramide channels (for example, sphingomyelin). Sphingomyelin is known to interact with ceramide and can thus divert ceramide from channel formation.

It is clear that apoptosis is fundamental to a variety of normal and disease processes and that ceramide is a key signaling molecule in apoptosis. The present invention provides a means for controlling the apoptotic process, and thus provides agents that can inhibit or induce apoptosis in a variety of cell types for treatment of a variety of pathological conditions. Cells that initiate the apoptotic pathway are already weakened and targeting downstream events such as the activation of caspases with small molecular weight caspase inhibitors does not prevent the release of cytochrome c and other proteins from the mitochondria. Loss of these proteins from the mitochondria only weakens the cell further. If the goal is to prevent apoptosis or necrosis, then it is desirable to address that goal in a manner which minimizes cell damage. The process should therefore be inhibited early, upstream of mitochondrial release of cytochrome c and other proteins. The present invention provides a molecular target for apoptotic induction or intervention that relates to the release of cytochrome c from mitochondria, a step that precedes the activation of most caspases. Thus, the present invention provides an advantage over therapeutic approaches that focus on controlling or preventing apoptosis through caspase inhibition.

Methods for the Identification of Apoptotic Inhibitors

Compounds that can cross membranes and have specific effects on ceramide channel formation are useful both to the importance of ceramide channel formation in various forms of apoptosis and as drugs to treat diseases involving apoptosis (e.g. cancer, stroke, neurodegenerative diseases, viral diseases, etc.). The present invention, by providing a molecular mechanism for apoptosis, permits the identification of compounds that potentiate or inhibit the apoptotic process. Thus, one aspect of the present invention relates to methods of identifying novel compounds capable of affecting apoptosis. Such identification can be accomplished by:
  (A) incubating a phospholipid membrane under conditions sufficient to permit the formation of ceramide channels through said membrane;
  (B) incubating said phospholipid membrane in the presence of a candidate apoptotic effector compound; and
  (C) determining whether the presence of said candidate apoptotic effector compound affects the formation or stability of said ceramide channels, relative to the extent of such formation or stability observed in the absence of said candidate apoptotic effector compound;
  wherein a compound that affects the formation or stability of said ceramide channels is an apoptotic effector compound.

In one embodiment, such methods comprise screening compounds for their ability to influence the formation of ceramide channels in liposomes or planar membranes. A variety of small molecules that effect ceramide channels have been identified in this manner (for example, sugars, such as trehalose, have been found to exhibit a potent inhibitory effects at 50 mM; sphingosine has been found to be a very potent inhibitor at 5 μM). Such liposomes or planar membranes can be produced using any of a variety of lipids. Preferably, however, the constituents of the liposomes or planar membranes will be selected to mimic those of the MOM, or to have relevance to such membranes (see, Weissig, V. et al. (2006) "LIPOSOMES AND LIPOSOME-LIKE VESICLES FOR DRUG AND DNA DELIVERY TO MITOCHONDRIA," J. Liposome Res. 16(3):249-264; Torchilin, V. P. (2006) "RECENT APPROACHES TO INTRACELLULAR DELIVERY OF DRUGS AND DNA AND ORGANELLE TARGETING," Annu. Rev. Biomed. Eng. 8:343-375; Elrick, M. J. et al. (2006) "SPHINGOSINE, A PRODUCT OF CERAMIDE HYDROLYSIS, INFLUENCES THE FORMATION OF CERAMIDE CHANNELS," Biophys. J. 1; 91(5):1749-1756; Bathori, G. et al. (2006) "CA2+-DEPENDENT CONTROL OF THE PERMEABILITY PROPERTIES OF THE MITOCHONDRIAL OUTER MEMBRANE AND VOLTAGE-DEPENDENT ANION-SELECTIVE CHANNEL (VDAC)," J. Biol. Chem. 281(25): 17347-17358; Stiban, J. et al. (2006) "DIHYDROCERAMIDE HINDERS CERAMIDE CHANNEL FORMATION: IMPLICATIONS ON APOPIOSIS," Apoptosis 11(5):773-780; Stover, T. C. et al. (2005) "SYSTEMIC DELIVERY OF LIPOSOMAL SHORT-CHAIN CERAMIDE LIMITS SOLID TUMOR GROWTH IN MURINE MODELS OF BREAST ADENOCARCINOMA," Clin. Cancer Res. 11(9):3465-3474).

In an alternative embodiment, candidate compounds can be screened for their effect on ceramide channel formation using mitochondrial membranes. Such membranes can be produced from their constituent compositions, or more preferably, whole mitochondria may be isolated and employed (especially mitochondria that lack Bcl-2 proteins). Yeast and mammalian mitochondria are particularly preferred. For example, isolated mitochondria may be treated with ceramide for a period of time (e.g., 10 min) followed by addition of a candidate compound and the effect of the candidate compound on ceramide-induced MOM permeability determined. Such a screening assay has been validated using sphingosine, which is able to close ceramide channels after they have formed (dihydroceramide did not exhibit this effect during a similar time span). This difference is important in applications in which a compound is being screened for its ability to stop an ongoing apoptotic process.

In a further alternative embodiment, candidate compounds can be screened for their effect on ceramide channel formation using the membranes of cells (i.e., "cellular membranes"). Such membranes can be produced from their constituent compositions, or more preferably, whole cells may be isolated and employed. Although any of a variety of cell types may be employed for this purpose, it is particularly desirable to employ eukaryotic cells, especially yeast or mammalian cells. Kidney epithelial cells (e.g., baby mouse kidney epithelial (BMK) cells) are preferred. It is moreover desirable to employ parental and/or Bax/Bak deficient (e.g., knock-out) variants. Mitochondria from such cell lines are sensitive to ceramide-induced permeabilization of the outer membrane. In accordance with such an assay, apoptosis is induced with TNF-alpha, hypoxia, and/or by addition of either $C_2$-ceramide or $C_6$-ceramide and the test compound, and the effect of the test compound on channel formation or channel stability is determined.

In a preferred embodiment, the assays of the present invention will be high-throughput assays, designed to process large numbers (e.g., >50) of candidate compounds simultaneously, for example, by conducting such assays using microtiter plates. As will be appreciated, candidate compounds may be tested alone or in conjunction with other compounds. For example, a candidate compound may be used alone to determine if it will stabilize or inhibit ceramide channel formation, or it may be used in combination with a known effector (e.g., sphingosine, trehalose, etc.), or a non-effector (e.g., dihydroceramide), or with one or more additional candidate compound(s) to determine or identify an antagonistic or synergistic effect.

Applications of Apoptotic Inhibitors and Inducers

Apoptotic effector compounds have therapeutic potential (see, Solary, E. et al. (1996) "THE ROLE OF APOPTOSIS IN THE PATHOGENESIS AND TREATMENT OF DISEASES," Eur. Respir. J. 9:1293-1305). Apoptotic effector compounds that act to inhibit or reverse apoptosis have therapeutic application in the treatment of diseases in which apoptosis is undesired. In stroke, for example, there is a combination of necrotic cell death and apoptotic cell death. Compounds that inhibit apoptosis by inhibiting ceramide channel formation have the ability to rescue cells that would otherwise die through apoptosis. An increased rate of cell death underlies multiple neurodegenerative diseases (such as Alzheimer's disease, Huntington's disease, Parkinson's disease, etc.) (Deigner, H-P. et al. (2000) "APOPTOSIS MODULATORS IN THE THERAPY OF NEURODEGENERATIVE DISEASES," Exp. Opin. Invest. Drugs 9(4): 747-764). Apoptotic effector compounds capable of inhibiting or reversing apoptosis thus may be used in the treatment of such diseases.

Viruses, for example, Kaposi sarcoma-associated herpes virus (KSHV), herpesvirus saimiri (HVS), and Epstein-Barr virus (EBV) contain viral genes that mimic those that the host uses to regulate cell growth and apoptosis (Hardwick, J. M. (1998) "VIRAL INTERFERENCE WITH APOPTOSIS," Semin. Cell Dev. Biol. 9:339-349). Such viruses are able to survive in the host cell and successfully replicate by interfering with the host cell's death and survival machinery. KSHV, HVS, and EBV encode Bcl-2 homologs called KsBcl-2, ORF16, and BHRF1, respectively. In gene transfer studies, these proteins have been shown to block apoptosis induced by various stimuli (Henderson, S. et al. (1993) "EPSTEIN BARR VIRUS-CODED BHRF1 PROTEIN, A VIRAL HOMOLOG OF BCL-2, PROTECTS HUMAN B CELLS FROM PROGRAMMED CELL DEATH," Proc. Natl. Acad. Sci. U.S.A. 90:8479-8483; Takayama, S. et al. (1994) "EVOLUTIONARY CONSERVATION OF FUNCTION AMONG MAMMALIAN, AVIAN, AND VIRAL HOMOLOGS OF THE BCL-2 ONCOPROTEIN," DNA Cell Biol. 13:679-692; Tarodi, B. et al. (1994) "EPSTEIN-BARR VIRUS BHRF1 PROTEIN PROTECTS AGAINST CELL DEATH INDUCED BY DNA-DAMAGING AGENTS AND HETEROLOGOUS VIRAL INFECTION," Virology 201:404-407). One aspect of the present invention derives from the recognition that such proteins protect against apoptosis through inhibition of ceramide channels (whether by interacting directly with ceramide or decreasing the local mitochondrial ceramide concentration). As such apoptotic effector compounds capable of inducing apoptosis may be used in the treatment of such viral infections.

Likewise, defects in the apoptosis process appear to be responsible for the ability of cancer cells to escape control and develop into tumors (Lowel, S. W. (2000) "APOPTOSIS IN CANCER," Carcinogenesis 21(3):485-495). Indeed, it has been proposed that chemotherapy mediates its anti-cancer effect by initiating apoptosis in the malignant cells, and that cells resistant to chemotherapy have damaged apoptotic response processes (Schmitt, C. A. et al. (1999) "APOPTOSIS AND THERAPY," J. Pathol. 187(1):127-137, Johnstone. R. W. et al. (2002) "APOPTOSIS: A LINK BETWEEN CANCER GENETICS AND CHEMOTHERAPY," Cell 108(2):153-164). Accordingly, apoptotic effector compounds capable of inducing apoptosis may be used in the treatment of cancer (including breast cancer, head and neck cancer, lung cancer, colon cancer, skin cancer, pancreatic cancer, prostate cancer, stomach cancer, brain cancer, etc.).

Pharmaceutical Compositions

The apoptotic effector compounds of the present invention may be employed as pharmaceutical agents, provided in therapeutically effective amounts, to effect the treatment of diseases and conditions. The term "treatment" as used herein covers any treatment of a disease, especially in a mammal, and particularly in a human, and includes: (i) preventing the disease from occurring in a subject which may be predisposed to the disease but has not yet been diagnosed as having it; (ii) inhibiting the disease, i.e. arresting its development; or (iii) relieving the disease, i.e. causing regression of the disease. As used herein, the term "therapeutically effective amount" refers to that amount of an apoptotic effector compound which, when administered to a mammal in need thereof, is sufficient to effect treatment (as defined above). The amount that constitutes a "therapeutically effective amount" will vary depending on the apoptotic effector compound being administered, the condition or disease and its severity, and the mammal to be treated, its weight, age, etc., but may be determined routinely by one of ordinary skill in the art with regard to contemporary knowledge and to this disclosure.

Accordingly, another aspect of the invention relates to pharmaceutical compositions and methods of treating a mammal in need thereof by administering therapeutically effective amounts of one or more apoptotic effector compound(s), or pharmaceutically acceptable salt(s) thereof. By "pharmaceutically acceptable salt" is intended to mean a salt that retains the biological effectiveness and properties of the apoptotic effector compound. Salts may be derived from acids or bases. Acid addition salts are derived from inorganic acids, such as hydrochloric acid, hydrobromic acid, sulfuric acid (giving the sulfate and bisulfate salts), nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, salicylic acid, p-toluenesulfonic acid, and the like. Base addition salts may be derived from inorganic bases, and include sodium, potassium, lithium, ammonium, calcium, magnesium salts, and the like. Salts derived from organic bases include those formed from primary, secondary and tertiary amines, substituted amines including naturally-occurring substituted amines, and cyclic amines, including isopropylamine, trimethylamine, diethylamine, triethylamine, tripropylamine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, N-ethylpiperidine, and the like. Preferred organic bases are isopropylamine, diethylamine, ethanolamine, piperidine, tromethamine, and choline.

The pharmaceutical compositions will typically include a conventional pharmaceutical carrier or excipient and an apoptotic effector compound of the present invention and, in addition, may include other medicinal agents, pharmaceutical agents, carriers, adjuvants, etc. Carriers can be selected from the various oils, including those of petroleum, animal, vegetable or synthetic origin, for example, peanut oil, soybean oil, mineral oil, sesame oil, and the like. Water, saline, aqueous dextrose, and glycols are preferred liquid carriers, particularly for injectable solutions. Suitable pharmaceutical carriers include starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like. Other suitable pharmaceutical carriers and their formulations are described in Gennaro, A. R. ("REMINGTON: THE SCIENCE AND PRACTICE OF PHARMACY," 21st Ed., Lippincott Williams & Wilkins (2005)) and Allen, L. V. et al. ("ANSEL'S PHARMACEUTICAL DOSAGE FORMS AND DRUG DELIVERY SYSTEMS," Lippincott Williams & Wilkins (2004)). Such pharmaceutical compositions may provide site-specific release of the apoptotic effector compounds.

The percentage of the active ingredient contained in such compositions is highly dependent on the specific nature thereof, as well as the activity of the compound and the needs of the subject. However, percentages of effector compound of 0.001% to 10% in solution are employable, and will be higher if the composition is a solid which will be subsequently diluted to the above percentages. Preferably the composition will comprise 0.002-8% of the active ingredient in solution.

Administration can be via any accepted systemic or local route, for example, via parenteral, oral (particularly for infant formulations), intravenous, nasal, bronchial inhalation (i.e., aerosol formulation), intraocular, intra-aural, transdermal or topical routes, in the form of solid, semi-solid or liquid or aerosol dosage forms, such as, for example, tablets, pills, capsules, powders, liquids, solutions, emulsion, injectables, suspensions, suppositories, aerosols or the like. Parenteral administration is generally characterized by injection, either subcutaneously, intramuscularly or intravenously, and can include intradermal or intraperitoneal injections as well as intrasternal injection or infusion techniques. The apoptotic effector compounds of the present invention can also be administered in sustained or controlled release dosage forms, including depot or bolus injections, infusions, osmotic pumps, pills, transdermal (including electrotransport) patches, and the like, for the prolonged administration of the polypeptide at a predetermined rate, preferably in unit dosage forms suitable for single administration of precise dosages. A typical daily dose of an apoptotic effector compound of the present invention can be administered by one infusion, or by a series of infusions spaced over periodic intervals. For parenteral administration there are especially suitable aqueous solutions of an active ingredient in water-soluble form, for example in the form of a water-soluble salt, or aqueous injection suspensions that contain viscosity-increasing substances, for example sodium carboxymethylcellulose, sorbitol and/or dextran, and, if desired, stabilizers. The active ingredient, optionally together with excipients, can also be in the form of a lyophilisate and can be made into a solution prior to parenteral administration by the addition of suitable solvents. A more recently devised approach for parenteral administration employs the implantation of a slow-release or sustained-release system, such that a constant level of dosage is maintained. See, e.g., U.S. Pat. Nos. 3,710,795, 5,714,166 and 5,041,292, which are hereby incorporated by reference.

Aerosol administration is an effective means for delivering the apoptotic inhibitors of the present invention directly to the respiratory tract. Some of the advantages of this method are: 1) it circumvents the effects of enzymatic degradation, poor absorption from the gastrointestinal tract, or loss of the therapeutic agent due to the hepatic first-pass effect; 2) it administers active ingredients which would otherwise fail to reach their target sites in the respiratory tract due to their molecular size, charge or affinity to extra-pulmonary sites; 3) it provides for fast absorption into the body via the alveoli of the lungs; and 4) it avoids exposing other organ systems to the active ingredient, which is important where exposure might cause undesirable side effects. For these reasons, aerosol administration is particularly advantageous for treatment of asthma, local infections of the lung, and other diseases or disease conditions of the lung and respiratory tract. There are three types of pharmaceutical inhalation devices, nebulizers inhalers, metered-dose inhalers and dry powder inhalers. Nebulizer devices produce a stream of high velocity air that causes the protein derivative (which has been formulated in a liquid form) to spray as a mist that is carried into the patient's respiratory tract. Metered-dose inhalers typically have the formulation packaged with a compressed gas and, upon actuation, discharge a measured amount of the polypeptide by compressed gas, thus affording a reliable method of administering a set amount of agent. Dry powder inhalers administer the polypeptide in the form of a free flowing powder that can be dispersed in the patient's air-stream during breathing by the device. In order to achieve a free flowing powder, the protein derivative is formulated with an excipient, such as lactose. A measured amount of the protein derivative is stored in a capsule form and is dispensed to the patient with each actuation. All of the above methods can be used for administering apoptotic effector compounds of the present invention.

Pharmaceutical formulations based on liposomes are also suitable for use with the polymer-modified synthetic bioactive proteins of this invention. See, e.g., U.S. Pat. Nos. 5,631, 018, 5,723,147, and 5,766,627. The benefits of liposomes are believed to be related to favorable changes in tissue distribution and pharmacokinetic parameters that result from liposome entrapment of drugs, and may be applied to the polypeptides of the present invention by those skilled in the art. Controlled release liposomal liquid pharmaceutical formulations for injection or oral administration can also be used.

For systemic administration via suppository, traditional binders and carriers include, for example, polyethylene glycols or triglycerides, for example PEG 1000 (96%) and PEG 4000 (4%). Such suppositories may be formed from mixtures containing the active ingredient in the range of from about 0.5 w/w % to about 10 w/w %; preferably from about 1 w/w % to about 2 w/w %.

Having now generally described the invention, the same will be more readily understood through reference to the following examples, which are provided by way of illustration and are not intended to be limiting of the present invention unless specified.

EXAMPLE 1

Influence of Sphingosine on Ceramide-Dependent Release of Adenylate Kinase from Isolated Mitochondria A. Materials and Methods:

1. Electrophysiological Recordings

Planar phospholipid membranes were produced by the monolayer method (Montal, M. et al. (1972) "FORMATION OF BIMOLECULAR MEMBRANES FROM LIPID MONOLAYERS AND A STUDY OF THEIR ELECTRICAL PROPERTIES," Proc. Natl. Acad. Sci. USA 69:3561-3566) as modified by Colombini, M. (1987) ("CHARACTERIZATION OF CHANNELS ISOLATED FROM PLANT MITOCHONDRIA," Methods Enzymol. 148:465-475), across a 100-μm-diameter hole in a Saran partition. Monolayers were produced using a solution of 0.5% w/v asolectin, 0.5% w/v DiPhyPC, 0.1% w/v cholesterol in hexane. This technique produces solvent-free phospholipid membranes whose lipid composition (focusing on the polar head-groups) is similar to that found in the mitochondrial outer membrane. It differs from the natural membrane in lacking proteins.

The aqueous solutions contained 1 mM $MgCl_2$, and 5 mM Pipes pH 6.8 with KCl varying from 0.10 M to 1.0 M. The KCl concentration on one side of the membrane, referred to as the "trans" side, was always 0.10 M, whereas the other side (the "cis" side) was adjusted as needed. The transmembrane voltage was electronically clamped and the current through the membrane was recorded. The voltage values indicated are the voltage differences across the membrane cis side minus trans side.

$C_2$-ceramide was stirred into the aqueous solution on each side of the membrane from a solution in DMSO, generally 0.5 mg/ml. Single or multiple additions, typically 20 l each, yielding a final concentration of 2 µg/ml, were made to achieve a desired level of conductance. Sphingosine additions of 5 µl were made from a solution in DMSO (4 mg/mL) yielding a final concentration of 4 µg/mL.

2. Adenylate Kinase Release Assay

Rat liver mitochondria were isolated by differential centrifugation of tissue homogenate essentially as described by Parsons, D. F. et al. (1966) ("CHARACTERISTICS OF ISOLATED AND PURIFIED PREPARATIONS OF THE OUTER AND INNER MEMBRANES OF MITOCHONDRIA," Ann. N.Y. Acad. Sci. 137:643-666). The preparation yielded a mitochondrial suspension containing 10 mg of protein per mL. 20 µl of a mitochondrial suspension were diluted into 1.2 ml of 70 mM sucrose, 210 mM mannitol, 0.1 mM EGTA, 1 mM Tris-HCl, pH 7.4 yielding a final protein concentration of 0.15 mg/mL. The mitochondria were incubated for 10 min at room temperature with varying amounts of ceramide added from a 4 mg/ml DMSO solution to determine the amount of ceramide that resulted in a 50% release of adenylate kinase. The mitochondria were then pelleted at 14,000 g for 5 min at 4° C. and the supernatant was kept on ice until assayed. 100 µl of supernatant was added to 700 µl of adenylate kinase reaction mixture: 50 mM Tris-HCl, pH 7.5, 5 mM MgSO4, 10 mM glucose, 5 mM ADP, 0.2 mM NADP, 10 units of hexokinase, and 10 units of glucose-6-phosphate dehydrogenase (Sottocasa, G. L. et al. (1967) "SEPARATION AND SOME ENZYMATIC PROPERTIES OF THE INNER AND OUTER MEMBRANES OF RAT LIVER MITOCHONDRIA," Methods Enzymol. 10:448-463). The enzymes were added to the rest of the reaction mixture 1 min before the addition of the mitochondrial supernatant to allow a trace of ATP to be consumed. The activity of adenylate kinase was detected as an increase in absorbance at 340 nm. Since the activity of the kinase decays with time, even on ice, experiments were performed in sets and the activity of the first supernatant was assayed again at the end of the set. The values were fitted to a first order decay and all values within the set were corrected for the decay of the activity, based on the time delay before assay.

To determine the effect of sphingosine pretreatment on ceramide permeabilization of the mitochondrial outer membrane, mitochondria were incubated at room temperature in the presence of varying concentrations of sphingosine for S min before addition of ceramide and incubation for 10 min. Untreated mitochondria and mitochondria hypotonically lysed (20 µl into 1.2 ml water) served as negative and positive controls, respectively.

Experiments with $C_{16}$-ceramide were performed in a similar way except as follows. The mitochondria were suspended in the above medium except that the 1 mM Tris buffer was replaced by 5 mM HEPES. To 1.0 mL of this medium at room temperature (RT) was added 17 µL of mitochondrial suspension that had been kept on ice at a concentration of 4 mg/mL. The final mitochondrial protein concentration during the experiment was 80 µg/mL. In the case of shocked mitochondria, the 1.0 mL of medium was replaced by water. Sphingosine was added, where appropriate, from a 0.25 mg/mL solution in DMSO. Typically 4-7 incubations were run in parallel. All samples were incubated for 5 min at RT. Then some samples received 0.4 mL of fatty acid depleted bovine serum albumin (BSA), 25 mg/mL, followed immediately by 20 µL of $C_{16}$-ceramide dissolved in isopropanol at 2 mg/mL. After a 10-min incubation at RT, 10 µL of 4 mM PMSF was added followed by centrifugation. In these experiments 0.3 mL of mitochondrial supernatant was added to the adenylate kinase reaction mixture.

3. Liposome Experiments

The polar extract of soybean phospholipids (Avanti Polar Lipids, Alabaster, Ala.) and cholesterol (Sigma Chemical, St. Louis, Mo.) were mixed in a 93:7 molar ratio in chloroform and dried under nitrogen followed by drying in vacuo overnight. This mixture resembles the lipid content of mammalian mitochondrial outer membranes. Five mg of this mixture were dispersed in 1 mL of 39 mM NaCl, 6 mM DPX (Molecular Probes, Eugene, Oreg.), 1.5 mM carboxyfluorescein (Acros Organics, Geel, Belgium) and subjected to four freeze-thaw/sonication cycles. After extrusion through a 0.2 µm filter (Avanti Polar Lipids) for 13 passes it was run through a gel filtration column equilibrated and eluted with 50 mM NaCl, 10 mM HEPES, 1 mM EDTA, pH 7.0. The liposomes were used within 30 h. Twenty-five microliters of liposomes were dispersed into 2.0 mL of the elution buffer and placed into a quartz fluorescence cuvette. The fluorescence was monitored using a Deltascan Spectrofluorometer (Photon Technology Instruments, West Sussex, UK) using excitation at 495 nm and emission at 520 nm. Forty microliters of $C_{16}$-ceramide (2 mg/mL of isopropanol) were added while stirring. Sphingosine was added from either a 1 mg/mL or a 0.1 mg/mL solution in DMSO.

B. Results and Analysis:

1. Influence on Ceramide-Dependent Release of Adenylate Kinase from Isolated Mitochondria Ceramide has been previously shown to increase the permeability of the MOM to small intermembrane space proteins such as cytochrome c and adenylate kinase (Siskind, L. J. et al. (2002) "CERAMIDE CHANNELS INCREASE THE PERMEABILITY OF THE MITOCHONDRIAL OUTER MEMBRANE TO SMALL PROTEINS," J. Biol. Chem. 277:26796-26803; Arora, A. S. et al. (1997) "CERAMIDE INDUCES HEPATOCYTE CELL DEATH THROUGH DISRUPTION OF MITOCHONDRIAL FUNCTION IN THE RAT," Hepatology 25:958-963; Ghafourifar, P. et al. (1999) "CERAMIDE INDUCES CYTOCHROME C RELEASE FROM ISOLATED MITOCHONDRIA. IMPORTANCE OF MITOCHONDRIAL REDOX STATE," J. Biol. Chem. 274: 6080-6084; Di Paola, M. et al. (2000) "CERAMIDE INTERACTION WITH THE RESPIRATORY CHAIN OF HEART MITOCHONDRIA," Biochemistry 39:6660-6668; Di Paola, M. et al. (2004) "CERAMIDE INDUCES RELEASE OF PRO-APOPTOTIC PROTEINS FROM MITOCHONDRIA BY EITHER A CA2+-DEPENDENT OR A CA2+-INDEPENDENT MECHANISM," J. Bioenerg. Biomembr. 36:165-170). Sphingosine has been reported to form channels but these are small and incapable of allowing proteins to cross membranes (Siskind, L. J. et al. (2005) "SPHINGOSINE FORMS CHANNELS IN MEMBRANES THAT DIFFER GREATLY FROM THOSE FORMED BY CERAMIDE," J. Bioenerg. Biomembr. 37:227-236). Thus the presence of both ceramide and sphingosine in a membrane may result in hybrid structures that may or may not be conductive. The release of adenylate kinase was used as a measure of MOM permeabilization to small proteins.

To look for interaction between sphingosine and ceramide, isolated rat liver mitochondria were treated with varying levels of sphingosine for 5 min, and then exposed to $C_2$-ceramide (29 µg/mL final) for 10 min at room temperature. The mitochondria were sedimented and the supernatant assayed for adenylate kinase activity. Under these conditions only 1% of this ceramide inserts into mitochondria (Siskind, L. J. et al. (2006) "CERAMIDE FORMS CHANNELS IN MITOCHONDRIAL OUTER MEMBRANES AT PHYSIOLOGICALLY RELEVANT CONCENTRATIONS," Mitochondrion 6(3):118-125, Siskind, L. J. et al. (2005) "SPHINGOSINE FORMS CHANNELS IN MEMBRANES THAT DIFFER GREATLY FROM THOSE FORMED BY CERAMIDE," J. Bioenerg. Biomembr. 37:227-236). The initial rates of these reactions were plotted in FIG. 2 after normalization for the amount of adenylate kinase activity released after hypotonic shock. Essentially total inhibition was observed by exposure to 0.3-0.6 µg/mL sphingosine, depending on the batch of isolated mitochondria. In the concentration range of sphingosine examined (up to 6 µg/mL), sphingosine alone did not induce the release of adenylate kinase (FIG. 2). Thus sphingosine could either destabilize ceramide channels or convert them to much smaller structures, incapable of allowing the passage of proteins.

These results, obtained with $C_2$-ceramide, differ somewhat from the results obtained with $C_{16}$-ceramide. As shown in FIG. 3, the use of $C_{16}$-ceramide resulted in a biphasic relationship for the permeabilization of the mitochondrial outer membrane and release of adenylate kinase. Adenylate kinase activity was determined by measuring the initial rate of increase in the level of NADPH in the medium. Mitochondria were preincubated with the indicated amount of sphingosine for 5 min. This was followed by the addition of $C_{16}$-ceramide to a final total concentration of 40 µg/mL. After a 10-min incubation, the supernatant was assayed for adenylate kinase activity as described above. At low concentration, sphingosine potentiated the permeabilization effect of ceramide whereas at higher concentrations it inhibited the formation of the ceramide channels, as in the case of $C_2$-ceramide. The actual initial rate of NADPH production was plotted and the rates observed with vehicle alone and after hypotonic shock are shown as horizontal lines in FIG. 3.

The potentiation might arise from metabolic conversion of sphingosine to ceramide by mitochondria. It has been reported that nearly half of the added sphingosine is converted to ceramide (Siskind, L. J. et al. (2005) "SPHINGOSINE FORMS CHANNELS IN MEMBRANES THAT DIFFER GREATLY FROM THOSE FORMED BY CERAMIDE," J. Bioenerg. Biomembr. 37:227-236); this is probably by the action of reverse ceramidase. Thus, the ceramide produced from the sphingosine might combine with the added ceramide to reach a critical level resulting in channel formation. Excess sphingosine overwhelms the system resulting in the same inhibition observed with $C_2$-ceramide.

This hypothesis was tested by determining whether sphingosine converted to ceramide would be capable of permeabilizing the MOM to adenylate kinase. Mitochondria were incubated with 2.4 µg/mL sphingosine for 5 min followed by addition of 10 mg of fatty acid depleted bovine serum albumin BSA to remove the unconverted sphingosine. The release of adenylate kinase is evident in FIG. 4 (S versus SB) indicating that the removal of excess sphingosine allowed the ceramide formed to permeabilize the MOM. Significantly, the combination of added ceramide and sphingosine converted to ceramide (SBC . . . after BSA was used to remove excess sphingosine) resulted in complete release of adenylate kinase. The long-chain ceramide produced from sphingosine cannot be removed from the mitochondrial membranes by BSA addition (Siskind, L. J. et al. (2002) "CERAMIDE CHANNELS INCREASE THE PERMEABILITY OF THE MITOCHONDRIAL OUTER MEMBRANE TO SMALL PROTEINS," J. Biol. Chem. 277:26796-26803). BSA alone did not result in any release of adenylate kinase. The addition of BSA to intact mitochondria or mitochondria treated with osmotic shock did not alter the level of adenylate kinase activity showing that BSA does not influence either adenylate kinase or the coupled enzyme assay.

An alternative hypothesis for the ability of low levels of sphingosine to enhance ceramide permeabilization of the MOM is a direct effect of low-levels of sphingosine on ceramide channel stabilization. To test this hypothesis, L-threo sphingosine was used instead of the natural D-erythro sphingosine. This optical isomer is not metabolized as readily as the natural isomer. Preincubation with the L-threo sphingosine resulted in the same biphasic effect on ceramide permeabilization of the MOM (FIG. 5). Thus the conversion to ceramide may not be necessary for the potentiating effect of sphingosine. Conversion was checked by removing excess L-threo sphingosine with BSA to see if there was a permeabilization of the MOM as observed with the same treatment with the D isomer. In this case, no penneabilization of the MOM to adenylate kinase was observed. This is consistent with the conclusion that the D but not the L isomer is converted to ceramide and that both the L and D isomers act to favor ceramide permeabilization of the MOM when present at low concentrations.

2. Sphingosine Enhances the Ability of Ceramide To Permeabilize Liposomal Membranes If the ability of low levels of sphingosine to enhance ceramide channel formation is a direct action on the channels, this influence should also be observed on ceramide channels formed in liposomes lacking proteins. In these liposomes there is no possibility of metabolism or indirect effects on protein factors.

FIG. 6A shows the fluorescence increase resulting from the release of carboxyfluorescein from liposomes after the addition of $C_{16}$-ceramide. FIG. 6B shows the fluorescence levels 100 seconds after ceramide addition. Pretreatment with sphingosine causes a biphasic enhancement of the ceramide-induced permeabilization. At the low doses of sphingosine, the formation of sphingosine channels is sufficiently minimal, allowing ceramide channel formation to dominate. At the higher doses the sphingosine-induced carboxyfluorescein release is high enough to mask the expected inhibition of ceramide channel formation. In any case, the biphasic enhancement is evident and closely mirrors the results obtained with mitochondria. The defined nature of the liposome experiments indicates that the observed effects of sphingosine on ceramide channel formation arise from a direct interaction of sphingosine with the ceramide in the membrane.

The ability of sphingosine to potentiate channel formation by long-chain ceramide but not by short-chain ceramide may lie in the fundamental structure of the channel. Molecular dynamics simulations (Anishkin, A. et al. (2006) "SEARCHING FOR THE MOLECULAR ARRANGEMENT OF TRANSMEMBRANE CERAMIDE CHANNELS," Biophys. J. 90:2414-2426) have provided evidence for dual curvature in ceramide monomers packed into the channel. Negative curvature in the plane of the membrane allows for formation of the annulus. Positive curvature normal to that plane allows for effective articulation between ceramides and the phospholipid bilayer. This articulation involves distortion of both ceramides and the phospholipids and would be ameliorated by the presence of lipids with positive curvature. Short-chain ceramide already has the low hydrocarbon bulk that would aid in generating the positive curvature. Low concentrations of sphingosine may serve the same function. At the high concentrations, sphingosine may intercalate into the ceramide channels resulting in their destabilization because sphingosine lacks the amide linkage (believed to be critical to channel stability) and has a net charge that would lead to electrostatic repulsion.

3. Sphingosine Promotes Disassembly of Ceramide Channels in Planar Membranes The observations of sphingosine induced suppression of ceramide permeabilization of mitochondrial and liposomal membranes could have a variety of mechanistic explanations. The higher levels of sphingosine might prevent the formation of ceramide channels from monomers (e.g., by forming non-conducting complexes with these monomers) or sphingosine might induce the disassembly of ceramide channels. Direct demonstration of sphingosine-induced ceramide channel disassembly was achieved by experiments on channel-formation in planar phospholipids membranes. Ceramide channel conductance increases in a stepwise fashion, and these conductance increases have been demonstrated to represent the growth of a single channel in the membrane (Siskind, L. J. et al. (2003) "ENLARGEMENT AND CONTRACTURE OF $C_2$-CERAMIDE CHANNELS," Biophys. J. 85:1560-1575) as opposed to many small channels acting in parallel (Kaulin, Y. A. et al. (1998) "CLUSTER ORGANIZATION OF ION CHANNELS FORMED BY THE ANTIBIOTIC SYRINGOMYCIN E IN BILAYER LIPID MEMBRANES," Biophys. J. 74:2918-2925). The increases in conductance in the left half of FIG. 7 are thus increases in the size of a single channel. The typical ceramide channel grows in this way over a period of time until it reaches a fairly stable size. At this point, sphingosine was added (FIG. 7) and the membrane conductance decreased over the next 15-20 min. The conductance declined until it reached the level of the unmodified membrane, indicating that the ceramide channel was completely disassembled. Six minutes later, the conductance increased once again but the nature of this conductance differed from that of a typical ceramide channel.

The signal observed during the earlier half of this experiment, representing the flow of current through the membrane, is characteristic of ceramide channels. These characteristics include the growth of the channel in a steady, stepwise fashion and a relatively high signal/noise. These characteristics continued through the phase of the experiment during which the conductance was decreasing, with the channel shrinking steadily, periodically punctuated with sharp decrements, and with the current signal showing a low level of noise. In contrast to this, the increase in conductance that followed showed no large increments and was highly noisy. The appearance of this particular type of noise is characteristic of sphingosine channels (Siskind, L. J. et al. (2005) "SPHINGOSINE FORMS CHANNELS IN MEMBRANES THAT DIFFER GREATLY FROM THOSE FORMED BY CERAMIDE," J. Bioenerg. Biomembr. 37:227-236), reflecting the fact that sphingosine forms multiple channels in the planar membrane and that these channels exist only transiently, thus explaining the wide fluctuations in the current.

4. Selectivity Change Corresponds to Transition from Ceramide Channel to Sphingosine Channels To test the interpretation of FIG. 7, selectivity experiments were performed to distinguish between ceramide conductance and sphingosine conductance. Ceramide and sphingosine channels differ in their ion selectivities. Ceramide channels are weakly cation selective (Siskind, L. J. et al. (2003) "ENLARGEMENT AND CONTRACTURE OF $C_2$-CERAMIDE CHANNELS," Biophys. J. 85:1560-1575), and the magnitude of this selectivity decreases as the channel size conductance increases. Sphingosine channels have a preference for anions, likely owing to the positive charge on the sphingosine molecule (Siskind, L. J. et al. (2005) "SPHINGOSINE FORMS CHANNELS IN MEMBRANES THAT DIFFER GREATLY FROM THOSE FORMED BY CERAMIDE," J. Bioenerg. Biomembr. 37:227-236), and thus they exhibit a positive reversal potential. Therefore, by monitoring the reversal potential one can distinguish between conductance arising from ceramide channels and that due to sphingosine channels.

FIG. 8 shows an experiment in which both the conductance and the reversal potential were measured at regular intervals. The applied voltage was changed in steps allowing the conductance to be measured. The reversal potential was calculated: reversal potential=applied voltage−[current/conductance]. The data in FIG. 8 was obtained after the conductance of the ceramide channel had stabilized and sphingosine was added. The conductance declined with time reaching a minimum at 20 min. Then the reversal potential changed rapidly from negative to positive values indicating a change from cation to anion selectivity and thus a change from ceramide channel conductance to the conductance of sphingosine channels. Significantly, a further rise in conductance resulted in little change in reversal potential because the selectivity of sphingosine channels remained fairly steady irrespective of the number of channels present or the magnitude of the overall conductance.

The timing of the change of reversal potential corresponded with the point at which the conductance of the membrane began to increase, as indicated by the dashed lines in FIG. 8. This behavior is indicative of a changeover in the primary source of the membrane selectivity from a single ceramide channel to many sphingosine channels.

Other features of note in data of FIG. 8 provide insight into the process of channel disassembly. The gradual loss of ceramide conductance is expected to reflect the shrinkage of the ceramide channel. As the channel becomes smaller the ion selectivity should increase as previously described (Siskind, L. J. et al. (2003) "ENLARGEMENT AND CONTRACTURE OF $C_2$-CERAMIDE CHANNELS," Biophys. J. 85:1560-1575). However, as the ceramide conductance declined the reversal potential of the membrane stayed roughly constant, and eventually moves toward zero. Therefore, the presence of sphingosine in the membrane prevents the expected selectivity increase. One possibility is that sphingosine channels may have already begun to form in parallel with the ceramide channel, and that the formation of these anion selective channels negates and eventually overcomes the increase in cation selectivity expected from the shrinking ceramide channel. Another possibility is that some of the sphingosine incorporates itself into the ceramide channels, and thus not only destabilizes them, but also changes their characteristic selectivity by introducing positive charge near the inner wall of the channel. These two possibilities are, of course, not mutually exclusive and could be occurring simultaneously. The dominance of one over the other may also depend on how much sphingosine was added.

These results demonstrate the ability of sphingosine to markedly reduce the ceramide-induced permeability of the outer mitochondrial membrane to intermembrane space proteins. In whole mitochondria this could be due to a variety of mechanisms but in view of the results obtained in planar membranes, simple disassembly of ceramide channels is the simplest explanation.

When experiments performed on mitochondria isolated from different animals are pooled, the error bars are fairly large because there is variability of the response from one mitochondrial preparation to another. However, the changes were always in the same direction and the reported effects are statistically significant. The relative response under different conditions also depended on the potency of the ceramide-induced permeabilization, again this varied from one batch of mitochondria to another.

The effects described here might be subject to a variety of criticisms. First of all one might be concerned that sphingosine might form micelles in the medium that would act as sinks for the ceramide resulting in the trapping of ceramide and thus inhibition of ceramide channel formation. However, the published CMC for sphingosine is more than 30 µg/mL (Deguchi, H. et al. (2004) "SPHINGOLIPIDS AS BIOACTIVE REGULATORS OF THROMBIN GENERATION," J. Biol. Chem. 279:12036-12042), far greater than the amounts used. In addition, by using radiolabeled sphingosine, it was found that more than 80% of added sphingosine partitioned into mitochondria and thus the amount of sphingosine in the medium is far less than that indicated in the results presented herein. Thus the possibility of an artifact from sphingosine micelles is unrealistic. Another criticism is the amounts of sphingolipids used in the present Example as compared to levels found in cells. Again the use of radioisotopes shows that most of the ceramide added does not insert into mitochondria (Siskind, L. J. et al. (2006) "CERAMIDE FORMS CHANNELS IN MITOCHONDRIAL OUTER MEMBRANES AT PHYSIOLOGICALLY RELEVANT CONCENTRATIONS," Mitochondrion 6(3):118-125). The amount that does insert is within the physiological range (approximately 4 pmoles $C_2$-ceramide per nmole of phospholipids over 5-30 minutes; from approximately 2.5 pmoles to approximately 5 pmoles $C_{16}$-ceramide per nmole of phospholipids over 5-30 minutes), the level measured early in apoptosis in mitochondria. The physiological levels of sphingosine in mitochondria during apoptosis are not well defined. Cellular levels increase to an equivalent of 1.5-3 µg/mL (Cuvillier, O. (2002) "SPHINGOSINE IN APOPTOSIS SIGNALING," Biochim. Biophys. Acta. 1585:153-162) but the level in the mitochondrial outer membrane is unascertained. However, the action of ceramidase would generate sphingosine and local levels may indeed be high enough to favor ceramide disassembly. Significantly, after correcting for differences in insertion of ceramide and sphingosine, the levels used herein are rather comparable as would be expected in the mitochondrial membrane when active turnover is occurring.

In sum, the observed-disassembly of ceramide channels in the presence of sphingosine demonstrates amplification of the negative regulation of ceramide channels through the action of ceramidase. This enzyme, found in mitochondrial membranes, hydrolyzes ceramide to produce sphingosine (El Bawab, S. et al. (2000) "MOLECULAR CLONING AND CHARACTERIZATION OF A HUMAN MITOCHONDRIAL CERAMIDASE," J. Biol. Chem. 275:21508-21513; Bionda, C. et al. (2004) "SUBCELLULAR COMPARTMENTALIZATION OF CERAMIDE METABOLISM: MAM (MITOCHONDRIA-ASSOCIATED MEMBRANE AND/OR MITOCHONDRIA"? Biochem. J. 382:527-533), thus reducing the concentration of ceramide in the membrane and leading to channel shrinkage or disassembly. This disassembly process could be hastened by the presence of the reaction product, sphingosine, which amplifies the effect of the decreasing concentration of ceramide on the size of the ceramide channel by direct interaction with the channel to destabilize it. It depends on the local sphingosine level because if the level is too low there is potentiation rather than inhibition. As ceramidase continues to act, the concentration of sphingosine relative to ceramide continues to increase, thus accelerating the disassembly process. This putative self-amplifying regulatory mechanism thus is an anti-apoptotic regulatory step. The potentiating effect of sphingosine at lower concentrations is also physiologically important and is consistent with the reported pro-apoptotic effect of sphingosine. The local concentration of sphingosine determines how it will act:

EXAMPLE 2

Ability of Sphingosine to Create Channels

The present invention establishes that sphingosine is capable of directly disassembling ceramide channels, thus proving the existence of this novel anti-apoptotic regulatory step. The ability of sphingosine, sphingosine-1-phosphate (S-1-P) and ceramide-1-phosphate the ability to form channels was investigated.

Of these only sphingosine produced real channels. S-1-P destabilized membranes and C-1-P was without reproducible effect. The channels formed by sphingosine are very different from those formed by ceramide (FIG. 9; Siskind, L. J. et al. (2005) "SPHINGOSINE FORMS CHANNELS IN MEMBRANES THAT DIFFER GREATLY FROM THOSE FORMED BY CERAMIDE," J. Bioenerg. Biomembr. 37:227-236). They are much smaller and more dynamic with much shorter open times. They show a weak selectivity for anions, which is independent of membrane conductance (small ceramide channels favor cations but the selectivity drops to nil as the channel grows in size). From a histogram of conductance increments and decrements, we calculated that the sizes of the sphingosine channels are less than 2 nm in diameter. Also, unlike ceramide, the conductance increments and decrements are virtually identical indicating that sphingosine channels do not enlarge in size like ceramide, but form de novo and disappear in a stochastic manner. These results support the contention that the amide linkage in the ceramide molecule is essential for the formation of large stable channels. Sphingosine lacks that linkage. Furthermore, unlike ceramide, sphingosine forms channels in erythrocytes with a molecular weight cut-off of 1,000 (FIG. 10; Siskind, L. J. et al. (2005) "SPHINGOSINE FORMS CHANNELS IN MEMBRANES THAT DIFFER GREATLY FROM THOSE FORMED BY CERAMIDE," J. Bioenerg. Biomembr. 37:227-236). Thus sphingosine also lacks the specificity for channel formation in the MOM. Interestingly, the cut-off is somewhat dependent on the mole percent of sphingosine indicating that the channel size varies slightly depending on the membrane concentration of sphingosine monomers. Sphingosine channels also behave very differently from ceramide channels in isolated mitochondria. Sphingosine partitions better into the membranes than does ceramide (85% insertion as compared to only 4% with ceramide), but results in very little protein release. The small release of cytochrome c (maximum of 15%) can be accounted for by metabolism of sphingosine to ceramide because almost half of the radiolabeled sphingosine was converted to ceramide in 10 min. Considering the amount of ceramide formed, one would have expected much more cytochrome c release to be detected. Thus, it was hypothesized that sphingosine can inhibit ceramide channel formation (Siskind, L. J. et al. (2005) "SPHINGOSINE FORMS CHANNELS IN MEMBRANES THAT DIFFER GREATLY FROM THOSE FORMED BY CERAMIDE," J. Bioenerg. Biomembr. 37:227-236).

For the outer membrane, rich with VDAC channels, the extra effect of forming sphingosine channels should not be a problem. Indeed, if these channels were capable of facilitating the flux of ATP/ADP through the outer membrane, they may actually be anti-apoptotic. It has been shown that a reduction in the outer membrane permeability to metabolites precedes the release of pro-apoptotic proteins from mitochondria (Vander Heiden, M. G. et al. (2000) "OUTER MITOCHONDRIAL MEMBRANE PERMEABILITY CAN REGULATE COUPLED RESPIRATION AND CELL SURVIVAL," Proc. Natl. Acad. Sci. U.S.A. 97:4666-4671). From a physiological standpoint, having a product of ceramide metabolism be anti-apoptotic is significant. By elevating the mitochondrial ceramidase activity, cells would inhibit apoptosis in 3 ways: reduce the steady-state level of ceramide and thus the propensity of ceramide channel formation and increase the permeability of the outer membrane to metabolites with sphingosine, and inhibition of ceramide channel formation through the action of sphingosine. Consistent with reports that sphingosine is pro-apoptotic, a large fraction of added radiolabeled sphingosine was found to be rapidly converted to ceramide (Siskind, L. J. et al. (2005) "SPHINGOSINE FORMS CHANNELS IN MEMBRANES THAT DIFFER GREATLY FROM THOSE FORMED BY CERAMIDE," J. Bioenerg. Biomembr. 37:227-236).

Thus, although sphingosine has the ability to form channels, the channels were found to be too small to permit the passage of intermembrane space proteins and thus sphingosine itself does not induce apoptosis by permeabilizing the outer membrane to proteins (Siskind, L. J. et al. (2005) "SPHINGOSINE FORMS CHANNELS IN MEMBRANES THAT DIFFER GREATLY FROM THOSE FORMED BY CERAMIDE," J. Bioenerg. Biomembr. 37:227-236). Experiments with whole cells indicate that sphingosine induces apoptosis by acting on specific proteins (Suzuki, E. et al. (2004) "SPHINGOSINE-DEPENDENT APOPTOSIS: A UNIFIED CONCEPT BASED ON MULTIPLE MECHANISMS OPERATING IN CONCERT," Proc. Natl. Acad. Sci. USA 10141:14788-14793). Nevertheless, addition of sphingosine to mitochondria results in rapid conversion to ceramide (Bionda, C. et al. (2004) "SUBCELLULAR COMPARTMENTALIZATION OF CERAMIDE METABOLISM: MAM (MITOCHONDRIA-ASSOCIATED MEMBRANE AND/OR MITOCHONDRIA"? Biochem. J. 382:527-533; Siskind, L. J. et al. (2005) "SPHINGOSINE FORMS CHANNELS IN MEMBRANES THAT DIFFER GREATLY FROM THOSE FORMED BY CERAMIDE," J. Bioenerg. Biomembr. 37:227-236; Woodcock, J. (2006) "SPHINGOSINE AND CERAMIDE SIGNALING IN APOPTOSIS," IUBMB Life 58(8): 462-466). Siskind et al. (2005) ("SPHINGOSINE FORMS CHANNELS IN MEMBRANES THAT DIFFER GREATLY FROM THOSE FORMED BY CERAMIDE," J. Bioenerg. Biomembr. 37:227-236) also noted that the ability of ceramide, generated from added sphingosine, to cause the release of cytochrome c was less than when the same quantities of ceramide were introduced into the mitochondrial membranes by direct addition of ceramide to the medium (no exogenous sphingosine). This observation supports the conclusions of the present invention that sphingosine destabilizes ceramide channels.

EXAMPLE 3

Treatments that Augment or Inhibit Ceramide Channel Formation

Both precursors and products of the ceramide metabolic pathway inhibit ceramide channel formation. Sphingosine is both precursor and product because ceramidase can both hydrolyse and synthesize ceramide. Unidentified conditions could bias the system in one direction or the other. Nevertheless, it was found that low levels of sphingosine (1-2 μM) actually stimulated ceramide induced permeabilization of the mitochondrial outer membrane to proteins, whereas higher levels (5-10 μM) strongly inhibited this channel formation. This was observed in both isolated mitochondria and in a liposome permeability assay. In addition, a ceramide channel formed in a planar membrane is disassembled by sphingosine (FIG. 9). Note the stepwise increase in conductance that is the formation of a single large ceramide channel. Following the addition of sphingosine the conductance declines as the channel disassembles. In this experiment the conductance went to background. A little later, a noisy conductance was seen, which is the formation of many sphingosine channels. The experiments were repeated in the presence of a salt gradient so that the selectivity of the conductance could be measured. As expected the initial ceramide conductance favored cations and this selectivity inverted to one favoring anions when the noisy sphingosine conductance formed.

Further observations made on isolated mitochondria provided additional support for the inhibition of sphingosine. For example, the non-physiological optical isomer of sphingosine, L-sphingosine gave the same results as D-sphingosine. Also since some of the sphingosine is converted to ceramide one might expect that removal of the excess sphingosine would allow the ceramide to form channels and permeabilize the outer membrane to proteins. This was indeed the case when fatty acid depleted albumin was used to remove the unconverted sphingosine.

In the de novo synthesis pathway, dihydroceramide is made first and then a desaturase uses oxygen and NADH to insert a trans double bond at the 4,5 position to generate ceramide. The dihydroceramide is generally regarded as inactive because it does not induce apoptosis nor does it form channels. However, it was found that dihydroceramide inhibits ceramide channel formation at 10% the ceramide level (FIG. 11). This was found both in liposomes as well as isolated mitochondria. Dihydroceramide may be incorporating into the ceramide assemblies on the membrane surface producing structures that fail to assemble into channels. Unlike sphingosine, once the channels are formed, dihydroceramide does not induce channel disassembly. Thus it is a kinetically-limited phenomenon.

From a physiological standpoint, the activation of the ceramide de novo synthesis pathway would produce a bolus of dihydroceramide that would then be converted to ceramide. The dihydroceramide may keep the ceramide from forming channels until a critical level of ceramide is achieved. Further conversion would both remove the inhibition and produce more ceramide for the self-assembly of channels. This could cause an explosive increase in channel formation and release of pro-apoptotic factors. This could be a contributing factor in the almost all-or-none response to apoptotic induction.

As indicated above, most observations made on defined systems (planar membranes and vesicles) also resulted in corresponding effects in isolated mitochondria. However, differences were observed with two agents. Both propranolol and dibucaine inhibit ceramide $C_2$- and ceramide $C_{16}$-induced permeabilization of mammalian MOM with an $IC_{50}$ for $C_{16}$-ceramide of 410 and 230 μM, respectively (doses similar to those used to inhibit Bax permeabilization). In yeast mitochondria, propranolol and dibucaine inhibited ceramide $C_2$-induced permeabilization, but somewhat potentiated the effect of ceramide $C_{16}$. Similar results were obtained in liposome experiments. These results indicate that inhibition of channel formation by long-chain ceramide involves a factor found in mammalian cells but not in the other systems.

EXAMPLE 4

Physiological Relevance and Specificity of Ceramide Channel Formation

The amount of ceramide that needs to be added to mitochondria to achieve permeabilization of the MOM to proteins is high compared to physiological levels. However, it is not the absolute ceramide concentration in solution that is important, but rather the concentration of ceramide in the membrane. In addition, only a small percentage of the ceramide added to the solution actually inserts into the membrane. This issue was directly addressed by using radiolabeled ceramide and simultaneously measuring how much ceramide inserts into rat liver mitochondria and how much permeabilization is achieved in the MOM by measuring the accessibility of exogenously added cytochrome c. It was found that as little as 2 pmoles of ceramide inserted per nmole of phospholipid is sufficient to permeabilize the outer membrane to cytochrome c (FIG. 12). Levels measured in mitochondria in the early stages of apoptosis are 4 pmoles per nmole. Thus, the results are well within the physiological range. Note that after correcting for the membrane partitioning, long and short-chain ceramide have equal potency as expected from the model of the ceramide channel. Also note the lack of effect of dihydroceramide despite the fact that it inserts into mitochondrial membranes to the same degree as ceramide.

EXAMPLE 5

Relationship between Ceramide and Members of the Bcl-2 Family

The Bcl-2 family of proteins is pivotal to the regulation of mitochondrial-mediated apoptosis (Antonsson, B. (2004) "MITOCHONDRIA AND THE BCL-2 FAMILY PROTEINS IN APOPTOSIS SIGNALING PATHWAYS," Mol. Cell Biochem. 256:141-155; Danial, N. N. et al. (2004) "CELL DEATH: CRITICAL CONTROL POINTS," Cell 116:205-219). This family of proteins includes anti-apoptopic (for example, Bcl-2 and Bcl-xL) and pro-apoptotic (for example, Bax, Bad, Bid, and Bak) members. The Bcl-2 family of proteins thus function either as bodyguards or assassins to positively or negatively control apoptosis (Green D. R. et al. (2004) "THE PATHOPHYSIOLOGY OF MITOCHONDRIAL CELL DEATH," Science 305:626-629; Cory, S. et al. (2003) "THE BCL-2 FAMILY: ROLES IN CELL SURVIVAL AND ONCOGENESIS," Oncogene. 22:8590-8607; Kirkin, V. et al. (2004) "THE ROLE OF BCL-2 FAMILY MEMBERS IN TUMORIGENESIS," Biochim. Biophys. Acta 1644:229-249; Packham, G. et al. (2005) "BODYGUARDS AND ASSASSINS: BCL-2 FAMILY PROTEINS AND APOPTOSIS CONTROL CHRONIC LYMPHOCYTIC LEUKAEMIA," Immunology. 114:441-449). Proteins in this family contain up to four sequence motifs termed Bcl-2 homology (BH) domains and are classically subdivided into three categories based on their function and structure. Proteins in the anti-apoptotic family include Bcl-2 and Bcl-xL and contain all four BH domains. There are multidomain proapoptotic proteins that contain BH domains 1-3 (for example, Bax, Bak, and Bok) and BH3 domain only proapoptotic proteins that include Bim, Bad, and Bid. Anti-apoptotic Bcl-2 members tend to block the release of proapoptotic proteins from the mitochondrial intermembrane space, whereas proapoptotic members tend to promote it.

Ceramide is a Bcl-2- and Bcl-xL-sensitive apoptotic stimulus. Ceramide-induced cytochrome c release is inhibited by preincubation with or overexpression of the anti-death protein Bcl-2 (Ghafourifar, P. et al. (1999) "CERAMIDE INDUCES CYTOCHROME C RELEASE FROM ISOLATED MITOCHONDRIA. IMPORTANCE OF MITOCHONDRIAL REDOX STATE," J. Biol. Chem. 274: 6080-6084; Zhang, J. et al. (1996) "BCL-2 INTERRUPTS THE CERAMIDE-MEDIATED PATHWAY OF CELL DEATH," Proc. Natl. Acad. Sci. U.S.A. 93:5325-5328; Geley, S. et al. (1997) "CERAMIDES INDUCE A FORM OF APOPTOSIS IN HUMAN ACUTE LYMPHOBLASTIC LEUKEMIA CELLS THAT IS INHIBITED BY BCL-2, BUT NOT BY CRMA," FEBS Lett. 400:15-18), or transfection of cells with BCl-$X_L$ (Gottschalk, A. et al. (1994) "IDENTIFICATION OF IMMUNOSUPPRESSANT-INDUCED APOPTOSIS IN A MURINE B-CELL LINE AND ITS PREVENTION BY BCL-X BUT NOT BCL-2," Proc. Natl. Acad. Sci. U.S.A. 91, 7350-7354; Wiesner, D. A. et al. (1997) "ANTI-IMMUNOGLOBULIN-INDUCED APOPTOSIS IN WEHI 231 CELLS INVOLVES THE SLOW FORMATION OF CERAMIDE FROM SPHINGOMYELIN AND IS BLOCKED BY BCL-$_{XL}$," J. Biol. Chem. 272:9868-9876).

The ability of the apoptotic Bcl-2 family members Bcl-2 and Bcl-xL to inhibit ceramide channel formation is therefore investigated. For this purpose, yeast are employed because they lack any known Bcl-2 family proteins (Polcic, P. et al. (2003) "RESPONSE OF YEAST TO THE REGULATED EXPRESSION OF PROTEINS IN THE BCL-2 FAMILY," Biochem. J. 374:393-402) and the genes encoding these proteins can be added to yeast cells one at a time. Pro-apoptotic Bcl-2 family members when expressed in yeast result in cell death, which is suppressed by coexpression of Bcl-xL (Priault, M. et al. (1999) "ROLE OF C-TERMINAL DOMAIN OF BAX AND BCL-XL IN THEIR LOCALIZATION AND FUNCTION IN YEAST CELLS," FEBS Lett. 443:225-228; Greenhalf, W. et al. (1996) "ROLE OF MITOCHONDRIA AND C-TERMINAL MEMBRANE ANCHOR OF BCL-2 IN BAX INDUCED GROWTH ARREST AND MORTALITY IN SACCHAROMYCES CEREVISIAE," FEBS Lett. 380:169-175; Minn, A. J. et al. (1999) "BCL-XL REGULATES APOPTOSIS BY HETERODIMERIZATION-DEPENDENT AND-INDEPENDENT MECHANISMS," EMBO J. 18:632-643). In addition, when Bax or Bcl-xL are expressed in yeast, they localize to mitochondria indicating that these proteins recognize yeast mitochondria.

The ability of the naturally-occurring $C_{16}$-ceramide to form channels in the mitochondrial outer membranes of isolated yeast mitochondria was assessed via the complex IV accessibility assay. This assay measures the bidirectional flux of cytochrome c across the mitochondrial outer membrane (MOM) by monitoring its oxidation by complex IV of the mitochondrial inner membrane electron transport chain. The initial rate of cytochrome c oxidation when expressed as a percent of the rate measured in mitochondria with damaged outer membranes is a good measure of the permeability of the MOM to proapoptotic proteins. This method has an advantage over simply looking for the release of cytochrome c because both channel prevention and reversal by a potential inhibitor can be evaluated.

Thus, mitochondria are isolated from wild type yeast and yeast strains expressing either human Bcl-2 or Bcl-xL according to previously published methods (Lee, A. et al. (1998) "THE ROLE OF YEAST VDAC GENES ON THE PERMEABILITY OF THE MITOCHONDRIAL OUTER MEMBRANE," J. Membr. Biol. 161:173-181). Isolated yeast mitochondria are incubated with the naturally occurring $C_{16}$-ceramide and its ability to form channels is evaluated according to the complex IV accessibility assay (Siskind, L. J. et al. (2002) "CERAMIDE CHANNELS INCREASE THE PERMEABILITY OF THE MITOCHONDRIAL OUTER MEMBRANE TO SMALL PROTEINS," J. Biol. Chem. 277: 26796-26803). This assay measures the CN-sensitive oxidation of exogenously-added reduced cytochrome c by cytochrome c oxidase of the inner membrane. It measures the permeability of the mitochondrial outer membrane (MOM) to cytochrome c. Only mitochondrial preparations with greater than 90% MOM intactness are utilized and the level of intactness is checked regularly during the experiment. Mitochondria are incubated with test agents (e.g., $C_{16}$-ceramide) for a predetermined period of time (e.g., 5-20 minutes), reduced cytochrome c is added and the absorbance is monitored at 550 nm. $C_{16}$-ceramide is added from a solution of isopropanol.

The results of such experiments indicate that $C_{16}$-ceramide forms channels in the MOM of isolated wild-type yeast mitochondria in a dose dependent manner (FIG. 13A). As the voltage dependent anion channel (VDAC) has been implicated in playing a role in mitochondrial-mediated apoptosis, we determined whether $C_{16}$-ceramide could form channels in the MOMs of mitochondria isolated from VDAC1 knock-out yeast. $C_{16}$-ceramide forms channels to the same extent in mitochondria isolated from VDAC1 knock-out yeast as it does in mitochondria isolated from wild-type (FIG. 13A). Thus, the ability of $C_{16}$-ceramide to form protein permeable channels in isolated mitochondria is not dependent on the presence of proteins in the Bcl-2 family nor VDAC The complex IV accessibility measures of the permeability of the MOM. The initial rate is expressed as a percentage of the rate of cytochrome c oxidation in mitochondria whose outer membranes are ruptured by hypotonic shock. A similar method, the complex III accessibility assay (Degli Esposti, M. et al. (1982) "KINETICS AND SIDEDNESS OF UBIQUINOL-CYTOCHROME C REDUCTASE IN BEEF-HEART MITOCHONDRIA," FEBS Lett. 146:101-105; as modified by Kluck, R. M. et al. (1999) "THE PRO-APOPTOTIC PROTEINS, BID AND BAX, CAUSE A LIMITED PERMEABILIZATION OF THE MITOCHONDRIAL OUTER MEMBRANE THAT IS ENHANCED BY CYTOSOL," J. Cell. Biol. 147:809-822), may be employed to ensure that any observed changes in the rate of cytochrome c oxidation in the complex IV accessibility assay is actually due to changes in channel formation and not due to an altered activity of cytochrome c oxidase.

The cytochrome c accessibility assays differ from the measurement of cytochrome c release because they measure the permeability of the MOM at that point in time. The cytochrome c release assay detects the result of a permeabilization that may still exist, may have passed or was merely due to short transient events. This explains why ceramide addition to isolated mitochondria results in clear permeabilization of MOM to cytochrome c whereas Bax and tBid can allow cytochrome c release without measurable increase in MOM permeability. Bax and iBid may only form transient channels.

Experiments were conducted in order to determine whether the anti-apoptotic proteins Bcl-2 and Bcl-xL influence ceramide channel formation in isolated yeast mitochondria. Purification of full-length Bcl-2 is difficult because of its extremely insoluble nature. Thus, full-length human Bcl-2 was expressed in yeast cells. Mitochondria isolated from Bcl-2 expressing cells are resistant to $C_{16}$-ceramide channel formation as compared to mitochondria isolated from empty vector control cells (FIG. 13B; FIG. 13C). In addition, purified full length Bcl-xL (FL Bcl-xL) inhibits $C_{16}$-ceramide channels in isolated wild-type yeast mitochondria and in yeast mitochondria isolated from VDAC1 knock-out cells. The MOM permeability was measured in isolated WT or VDAC1 KO yeast mitochondria incubated with the indicated amount of full-length Bcl-xL for 10 min followed by a 10 min incubation with 2 µM $C_{16}$-ceramide (FIG. 13D). FL Bcl-xL can prevent ceramide channel formation when it is added to mitochondria before C16-ceramide (FIG. 13E). Thus, when C16-ceramide is added to mitochondria and allowed to form channels prior to the addition of FL Bcl-xL, it can also induce the disassembly (reversal) of the ceramide channels. MOM permeability was measured in isolated WT yeast mitochondria incubated first with 20 µM C16-ceramide for 10 min followed by a 10 min incubation with FL Bcl-xL (FIG. 13E). Full length (FL) Bcl-xL was purified by two different laboratories that utilized two different purification protocols and in both cases prevention and reversal of the $C_{16}$-ceramide channels was observed. Thus, inhibition of $C_{16}$-ceramide channel formation by FL Bcl-xL in MOMs does not depend on the presence of pro-apoptotic Bcl-2 proteins, the purification protocol, or VDAC1. Prevention and reversal of ceramide channel formation by Bcl-xL was however dependent on the full length version of the protein as deletion mutants lacking the C-terminal hydrophobic transmembrane domain (ΔTM Bcl-xL), the flexible loop region (Δloop Bcl-xL), both the transmembrane domain and the flexible loop region (ΔTM Δloop Bcl-xL), and N-terminal amino acids 2-76 (ΔN76 Bcl-xL) are all unable to prevent or reverse the ceramide channels in the MOM of isolated yeast mitochondria (FIG. 13F). The Bcl-xL deletion mutant ΔN76 Bcl-xL is known to be proapoptotic instead of anti-apoptotic and actually activates $C_{16}$-ceramide channel formation (FIG. 13F). As shown in FIG. 13F, isolated WT yeast mitochondria were incubated with the indicated treatments for 10 min each in the following order: prevention indicates that the mitochondria were incubated first with 20 µg of the specified protein followed by 20 µM $C_{16}$-ceramide, whereas reversal indicates an incubation with $C_{16}$-ceramide prior to the specified protein. MOM permeability was measured as described above. MOM permeability was measured as described above. The data thus show that when $C_{16}$-ceramide is added to mitochondria and allowed to form channels prior to the addition of FL Bcl-xL, it can also induce the disassembly (reversal) of the ceramide channels. All Bcl-xL deletion mutants were utilized at neutral as well as at acidic pH, where they have been shown to more effectively insert into membranes. Regardless of pH, none of the deletion mutants were capable of preventing or reversing the ceramide channels.

The results show that mitochondria isolated from Bcl-2 expressing yeast (FIG. 13B; FIG. 13C) require a much higher dose of ceramide to achieve the same degree of MOM permeabilization. Mitochondria from empty vector transfected yeast are used as a transfection control. Western blots are performed to ensure that the mitochondria indeed contain Bcl-2 or Bcl-xL. To determine if the decreased sensitivity of the yeast to ceramide is indeed due to an inhibition of ceramide channels and not due to a decreased insertion of ceramide, $^{14}$C-labeled ceramide is be used. Human Bad (purchased from Chemicon, Temecula, Calif.) and/or monomeric Bax (isolated according to the method of Suzuki, A. et al. (1997) "SEQUENTIAL OPERATION OF CERAMIDE SYNTHESIS AND ICE CASCADE IN CPT-11-INITIATED APOPTOTIC DEATH SIGNALING," Exp. Cell Res. 233:41-47) is added to the Bcl-2 expressing mitochondria to evaluate whether the ceramide channel inhibition by Bcl-2 or Bcl-xL can be reversed by binding up Bcl-2 with a proapoptotic Bcl-2 family member.

In order to gain insight into the mechanism by which Bcl-2 or Bcl-xL might reduce ceramide-induced MOM permeabilization, experiments are performed to determine if these proteins decrease the number or size of the ceramide channels. The cut-off for the channels formed in mitochondria will be measured as in Siskind et al. (2002) ("CERAMIDE CHANNELS INCREASE THE PERMEABILITY OF THE MITOCHONDRIAL OUTER MEMBRANE TO SMALL PROTEINS," J. Biol. Chem. 277:26796-26803) by incubating mitochondria with C16-ceramide, pelleting the mitochondria, and separating the proteins released on SDS-PAGE. The cut-off size for ceramide channels in rat liver mitochondria is 60,000. This is done in mitochondria isolated from yeast expressing Bcl-2 or Bcl-xL as well as empty vector controls. Full length Bcl-2 and Bcl-xL proteins are purified (Thuduppathy, G. R. et al. (2006) "EVIDENCE THAT MEMBRANE INSERTION OF THE CYTOSOLIC DOMAIN OF BCL-X(L) IS GOVERNED BY AN ELECTROSTATIC MECHANISM," J. Molec. Biol. 359:1045-1058; Garcia, C. et al. (2003) "ANTIMYCIN A(3) INHIBITS SINGLE ION CHANNELS FORMED BY BCL-2," Biophys. J. 84:204A) and tested for their effects on ceramide channel formation in isolated mitochondria.

Experiments show that purified full-length Bcl-xL can both prevent and reverse $C_{16}$-ceramide channels in mitochondria from rat liver and yeast (FIG. 14). Each batch of purified Bcl-2 or Bcl-xL is characterized by SDS-PAGE followed by Coomassie stain and western blot. Alkaline treatment of the mitochondria following their incubation with the recombinant proteins is performed to determine if they are actually inserting into the membrane or merely loosely associated with the MOM. Experiments are performed to determine if the recombinant proteins inhibit ceramide insertion into the mitochondrial membrane as opposed to acting by interfering with channel formation.

Experimental results indicate that Bcl-2 and Bcl-xL inhibit the ceramide channels. Such inhibition may be direct or indirect. A direct effect would be mediated through a direct physical interaction between Bcl-2 and/or Bcl-xL and ceramide whether in the monomeric form or preassembled into channels. Bcl-2 and/or Bcl-xL could bind ceramide monomers and cause channel disassembly by mass action. Alternatively, these proteins could interact only with preassembled ceramide channels. The data indicate that Bcl-xL in isolated mitochondria interacts with ceramide monomers. When Bcl-xL is added to the mitochondria before ceramide, it is able to prevent ceramide channels from ever forming. In addition, when ceramide is added to the mitochondria first and allowed to form channels prior to the addition of Bcl-xL, the protein can disassemble the preformed ceramide channels (FIG. 14). Thus, it may be concluded that Bcl-xL interacts with ceramide in the monomeric form or stabilizes some non-conducting assembly or mediates its effect by activating a mitochondrial ceramidase.

The anti-apoptotic proteins: Bcl-2 and Bcl-xL have homologous BH (Bcl-2 homology)-1, BH2, BH3, and BH4 domains. The BH1, BH2, and BH4 domains have been shown to be essential for the anti-apoptotic function. These proteins also have a transmembrane C-terminal domain. The three-dimensional structures show a 60-amino acid flexible loop domain between helices 1 and 2 that may be important. These attributes indicate that a specific region of Bcl-2 and/or Bcl-xL is responsible for their ability to inhibit ceramide channels. The transmembrane region of Bcl-xL is found to be important for the inhibition of the ceramide channels. In addition, a mutant version of Bcl-xL (delta N76 Bcl-xL) that is actually proapoptotic, activates the ceramide channels rather then inhibiting them.

One of the pro-survival functions of Bcl-2 and Bcl-xL is the inhibition of the activities of the pro-apoptotic members of the Bcl-2 family by binding to them. In fact the rheostat model for apoptosis proposes that cell death and survival are regulated by the balance between proapoptotic and antiapoptotic classes of Bcl-2 proteins (Korsmeyer, S. J. et al. (1993) "BCL-2/BAX: A RHEOSTAT THAT REGULATES THE ANTI-OXIDANT PATHWAY AND CELL DEATH," Semin. Cancer Biol. 4:327-332). Cell death must be actively induced by both inhibition of the antiapoptotic function of Bcl-2 and Bcl-xL and engaging the proapoptotic members (Kuwana, T. et al. (2002) "BID, BAX, AND LIPIDS COOPERATE TO FORM SUPRAMOLECULAR OPENINGS IN THE OUTER MITOCHONDRIAL MEMBRANE," Cell. 111:331-342). Ceramide has many functions. In addition to form protein permeable channels, ceramide is able to induce apoptosis in part by binding to Bcl-2 and/or Bcl-xL and preventing the binding of and/or induce the dissociation of bound proapoptotic Bcl-2 family members. Thus, ceramide interaction with Bcl-2 and/or Bcl-xL shifts the balance toward the proapoptotic Bcl-2 family members.

The phosphorylation state of Bcl-2 proteins appears to be important to their mode of action on ceramide channels; in the phosphorylated form, Bcl-2 may better inhibit ceramide channels. Alternatively, the dephosphorylated form of Bcl-2 could actually promote ceramide channel formation. Likewise, the phosphorylation status of Bad and Bax may be important to their effects on ceramide channels; upon their dephosphorylation, Bax and Bad could promote ceramide channel formation and/or form hybrid channels with ceramide. Data indicate that mitochondria isolated from Bcl-2 expressing yeast are resistant to ceramide channel formation.

Evidence indicates that pro-apoptotic Bcl-2 family members act in concert with ceramide. For example, exogenously-added ceramide potentiates the ability of Bax to initiate apoptosis (Pastorino, J. G. et al. (1999) "FUNCTIONAL CONSEQUENCES OF THE SUSTAINED OR TRANSIENT ACTIVATION BY BAX OF THE MITOCHONDRIAL PERMEABILITY TRANSITION PORE," J. Biol. Chem. 274:31734-31739). It has been reported that for some cell types and tissues, Bax translocation from the cytosol to mitochondria occurs following ceramide production (Kim, H. J. et al. (2001) "BAX-DEPENDENT APOPTOSIS INDUCED BY CERAMIDE IN HL-60 CELLS," FEBS Lett. 505:264-268) Treatment of MCF7 cells with TNF resulted in increased mitochondrial ceramide levels that were associated with Bax translocation to mitochondria (Birbes, H. et al. (2005) "A MITOCHONDRIAL POOL OF SPHINGOMYELIN IS INVOLVED IN TNFALPHA-INDUCED BAX TRANSLOCATION TO MITOCHONDRIA," Biochem. J. 386:445-451). Additionally, the addition of $C_{16}$-ceramide to isolated mitochondria stimulated Bax translocation to mitochondria and subsequent cytochrome c/Smac release. Ceramide-induced Bax conformational change was found to occur in isolated mitochondria fractions and not in mitochondrial protein lysates or cytosolic fractions (Kashkar, H. et al. (2005) "ACID SPHINGOMYELINASE IS INDISPENSABLE FOR UV LIGHT-INDUCED BAX CONFORMATIONAL CHANGE AT THE MITOCHONDRIAL MEMBRANE," J. Biol. Chem. 280(21): 20804-20813). While ceramide can clearly induce cytochrome c release and apoptosis under Bax deficient conditions, the presence of Bax often enhances ceramide-induced apoptosis (Von Haefen, C. et al. (2002) "CERAMIDE INDUCES MITOCHONDRIAL ACTIVATION AND APOPTOSIS VIA A BAX-DEPENDENT PATHWAY IN HUMAN CARCINOMA CELLS," Oncogene 21:4009-4019). Clearly Bax is not required for ceramide channel formation (Siskind, L. J. et al. (2000) "The Lipids $C_2$- And $C_{16}$-Ceramide Form Large Stable Channels In Membranes: Implications For Apoptosis," J. Biol. Chem. 275: 39640-39644; Siskind, L. J. et al. (2002) "Ceramide Channels Increase The Permeability Of The Mitochondrial Outer Membrane To Small Proteins," J. Biol. Chem. 277:26796-26803; Siskind, L. J. et al. (2003) "Enlargement And Contracture Of $C_2$-Ceramide Channels," Biophys. J. 85:1560-157) as ceramide channels are observed in planar phospholipid membranes free of proteins and ceramide channels allow the release of intermembrane space proteins less than 60 kDa in size from isolated rat liver mitochondria (reported to lack Bax, Polster, B. M. et al. (2001) "BH3 DEATH DOMAIN PEPTIDE INDUCES CELL TYPE-SELECTIVE MITOCHONDRIAL OUTER MEMBRANE PERMEABILITY," J. Biol. Chem.276(41): 37887-37894). Results of the present invention indicate that ceramide forms large protein permeable channels in the outer membranes of mitochondria isolated from Bax/Bak double knock-out cells just as well as in mitochondria from wild-type cells. However, it is possible that in vivo Bax and ceramide may form hybrid channels. Alternatively, Bax could promote the enlargement or stabilization of ceramide channels (or vice versa) or ceramide could promote the insertion of Bax into mitochondrial membranes.

The observations obtained with yeast mitochondria apply as well to mammalian mitochondria. When isolated rat liver mitochondria were incubated with FL Bcl-xL for 10 min prior to incubation with $C_{16}$-ceramide for 10 min, almost complete prevention of $C_{16}$-ceramide channel formation was observed at levels of FL Bcl-xL as low as 1.5 µg (FIG. 15A). Disassembly of preformed $C_{16}$-ceramide channels by FL Bcl-xL was observed at even lower levels of FL Bcl-xL (5 µg or less;

FIG. 15A). Unlike the simple dose dependent channel prevention that was observed when the mitochondria were exposed to FL Bcl-xL prior to $C_{16}$-ceramide, a biphasic effect was observed when the ceramide was allowed to form channels in the MOMs of the isolated mitochondria prior to the addition of Bcl-xL (FIG. 15A). Bcl-xL deletion mutants in isolated rat liver mitochondria were unable to prevent or reverse $C_{16}$-ceramide channel formation. As was the case in isolated yeast mitochondria, the proapoptotic ΔN76 Bcl-xL activated rather than inhibited the $C_{16}$-ceramide channels in isolated rat liver mitochondria. The inhibition of the $C_{16}$-ceramide channels by the FL-Bcl-xL in rat liver mitochondria correlates with the inhibition observed in yeast mitochondria and thus does not involve proapoptotic proteins in the Bcl-2 family.

Ced-9, the C. elegans Bcl-2 homologue, also inhibits ceramide channel formation (FIG. 15B). The purified Ced-9 protein requires the presence of thiol reducing agents, DTT, for it to remain in its monomer form. However, DTT interferes with the complex IV accessibility assay. An assay was therefore utilized which measures the release of adenylate kinase from the mitochondrial intermembrane space. As was the case with Bcl-2, Ced-9 inhibited $C_{16}$-ceramide channel formation in a dose dependent manner in rat liver mitochondria (FIG. 15B).

The observation that anti-apoptotic Bcl-2 family proteins inhibit ceramide channel formation in isolated yeast and rat liver mitochondria correlates with previous reports showing inhibition of ceramide-induced apoptosis in whole cells by these proteins. Thus the results directly tie ceramide-induced mitochondrial-mediated apoptosis with the Bcl-2 family of proteins known to regulate these events. To address whether the antiapoptotic proteins act directly on ceramide channels or work by an indirect action, their affects on ceramide channels in solvent-free planar phospholipid membranes was tested. This is a defined system free of other proteins. When $C_{16}$-ceramide is added to the aqueous solution bathing one side of a planar phospholipid membrane, it results in discontinuous increases in conductance under voltage-clamp conditions, the defining characteristic of channel formation in membranes. These conductance increments are the enlargement of one ceramide channel rather than the formation of multiple ceramide channels in parallel (Siskind, L. J. et al. (2003) "ENLARGEMENT AND CONTRACTURE OF $C_2$-CERAMIDE CHANNELS," Biophys. J. 85:1560-1575). Once the $C_{16}$-ceramide channel enlarged in size and reached a steady conductance level, incubation was continued for at least 5 minutes to ensure that the channel was indeed stable. Bcl-xL was then added while stirring to the opposite side of the membrane from the side to which $C_{16}$-ceramide was added. This resulted in a dramatic decrease in the ceramide conductance to baseline (FIG. 16A). Vehicle controls resulted in no conductance change. Addition of the ΔN76 Bcl-xL to the planar phospholipids membrane containing $C_{16}$-ceramide channel did not result in channel inhibition (FIG. 16B), showing that inhibition of $C_{16}$-ceramide channels is specific to the version of the protein that is anti-apoptotic. Similar experiments were performed with Ced-9, which also inhibited the $C_{16}$-ceramide channels. Unlike the FL Bcl-xL, Ced-9 did not decrease the conductance completely to baseline. The very small remaining conductance is most likely due to the Ced-9, which has been shown to increase the permeability of liposomes and may form small channels by itself.

The inhibition of the $C_{16}$-ceramide channels by FL Bcl-xL and Ced-9 in planar phospholipid membranes shows for the first time a direct interaction between ceramide channels and anti-apoptotic Bcl-2 proteins. The results have profound implications on multiple levels. First, channel inhibitors are relied on as a means of identifying a particular permeability change as being due to a particular channel. The fact the FL Bcl-xL and Ced-9 inhibit $C_{16}$-ceramide channels in planar phospholipid membranes proves unequivocally that the increase in permeability of the MOM and protein release from isolated mitochondria that is observed with $C_{16}$-ceramide is in fact due to its ability to form channels. The level of mitochondrial ceramide that is achieved during the induction phase of apoptosis (Birbes, H. et al. (2005) "A MITOCHONDRIAL POOL OF SPHINGOMYELIN IS INVOLVED IN TNFALPHA-INDUCED BAX TRANSLOCATION TO MITOCHONDRIA," Biochem. J. 386:445-451) Garcia-Ruiz et al. (1997) ("DIRECT EFFECT OF CERAMIDE ON THE MITOCHONDRIAL ELECTRON TRANSPORT CHAIN LEADS TO GENERATION OF REACTIVE OXYGEN SPECIES. ROLE OF MITOCHONDRIAL GLUTATHIONE," J. Biol. Chem. 272:11369-11377; Rodriguez-Lafrasse, C. et al. (2002) "INCREASING ENDOGENOUS CERAMIDE USING INHIBITORS OF SPHINGOLIPID METABOLISM MAXIMIZES IONIZING RADIATION-INDUCED MITOCHONDRIAL INJURY AND APOPTOTIC CELL KILLING," Int. J. Cancer 101:589-598) is consistent with the level of ceramide required for the formation of protein permeable channels (Siskind, L. J. et al. (2006) "CERAMIDE FORMS CHANNELS IN MITOCHONDRIAL OUTER MEMBRANES AT PHYSIOLOGICALLY RELEVANT CONCENTRATIONS," Mitochondrion 6(3): 118-125 (Epub 2006 Mar. 29)). Secondly, the results are important because they show that the ability of ceramide to induce mitochondrial-mediated apoptosis is at least in part due to its ability to form channels. Thirdly, the inhibition of ceramide channels by anti-apoptotic Bcl-2 proteins at least partially explains their ability to inhibit ceramide-induced apoptosis in whole cell systems. Fourthly, the inhibition of ceramide channels by anti-apoptotic Bcl-2 proteins directly ties ceramide-induced mitochondrial-mediated apoptosis in with the Bcl-2 system of regulation of these events. Additionally, inhibition of ceramide channels by anti-apoptotic Bcl-2 proteins make these channels good candidates for the pathway through which proapoptotic proteins are released from mitochondria during the induction phase of apoptosis.

EXAMPLE 6

Ceramide Channel Stabilizers and Inhibitors

As discussed above, ceramide addition to whole cells or isolated mitochondria results in the release of proapoptotic proteins from mitochondria and this release is inhibited by the anti-apoptotic proteins Bcl-2 and Bcl-xL. However, the mechanism for the ceramide-induced release of proapoptotic proteins from mitochondria is still highly debated despite the fact that ceramide channels are indeed large enough to allow for the passage of proapoptotic proteins and the levels of mitochondrial ceramide required for channel formation matches the level achieved during the induction phase of apoptosis (Siskind, L. J. et al. (2006) "CERAMIDE FORMS CHANNELS IN MITOCHONDRIAL OUTER MEMBRANES AT PHYSIOLOGICALLY RELEVANT CONCENTRATIONS," Mitochondrion 6(3):118-125). Nevertheless, the general consensus is that the protein efflux pathway is generated by the pro-apoptotic Bcl-2 proteins: Bax, Bak, and Bid. Thus ceramide permeabilize the mitochondria outer membrane by favoring the formation of a channel by Bcl-2 proapoptotic proteins All publications and patents mentioned in this specification are herein incorporated by reference to the same extent as if each individual publication or patent application was specifically and individually indicated to be incorporated by reference in its entirety.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A method for identifying an apoptotic effector compound, wherein said method comprises the steps of:
   (A) incubating a phospholipid membrane under conditions sufficient to permit the formation of ceramide channels through said membrane;
   (B) incubating said phospholipid membrane in the presence of a candidate apoptotic effector compound; and
   (C) determining whether the presence of said candidate apoptotic effector compound affects the formation or stability of said ceramide channels, relative to the extent of such formation or stability observed in the absence of said candidate apoptotic effector compound;
   wherein a compound that affects the formation or stability of said ceramide channels is an apoptotic effector compound.

2. The method of claim 1, wherein said step (B) is performed prior to performing said step (A).

3. The method of claim 1, wherein said conditions (A) sufficient to permit the formation of ceramide channels comprise providing a ceramide to said phospholipid membrane.

4. The method of claim 3, wherein said ceramide is $C_{16}$-ceramide.

5. The method of claim 1, wherein said phospholipid membrane is of defined composition and is a planar membrane or a liposome membrane.

6. The method of claim 5, wherein said conditions (A) sufficient to permit the formation of ceramide channels comprise providing an agent selected from the group consisting of: nitrous oxide, etoposide, staurosporine, daunorubicin and dexamethasone.

7. The method of claim 1, wherein said phospholipid membrane is a membrane of a mitochondrion, or a cellular membrane of a yeast or mammalian cell.

8. The method of claim 7, wherein said conditions (A) sufficient to permit the formation of ceramide channels comprise providing an agent selected from the group consisting of: TNF-alpha, interleukin-1, nitrous oxide, etoposide, staurosporine, daunorubicin and dexamethasone.

9. The method of claim 7, wherein said conditions (A) sufficient to permit the formation of ceramide channels comprise subjecting said membrane to ionizing radiation, hypoxia or heat.

10. The method of claim 7, wherein said conditions (A) sufficient to permit the formation of ceramide channels comprise subjecting said cell to serum withdrawal.

11. The method of claim 7, wherein said phospholipid membrane is a membrane of a mitochondrion.

12. The method of claim 11, wherein said mitochondrion lacks Bcl-2 proteins.

13. The method of claim 7, wherein said phospholipid membrane is a cellular membrane of a yeast or mammalian cell.

14. The method of claim 13, wherein said cell is Bax or Bak deficient.

15. The method of claim 13, wherein said cell is a mammalian cell.

16. The method of claim 1, wherein said candidate apoptotic effector compound inhibits the formation or stability of said ceramide channels, relative to the extent of such formation or stability observed in the absence of said candidate apoptotic effector compound.

17. The method of claim 16, wherein said candidate apoptotic effector compound inhibits the formation of ceramide channels but does not affect the stability of formed ceramide channels, relative to the extent of such formation or stability observed in the absence of said candidate apoptotic effector compound.

18. The method of claim 1, wherein said candidate apoptotic effector compound induces the formation of, or enhances the stability of, said ceramide channels, relative to the extent of such formation or stability observed in the absence of said candidate apoptotic effector compound.

19. The method of claim 1, wherein said candidate apoptotic effector compound inhibits the formation induces the formation of, or enhances the stability of, said ceramide channels, relative to the extent of such formation or stability observed in the absence of said candidate apoptotic effector compound.

20. A method of measuring the apoptotic effect of an apoptotic effector compound said method comprising the steps of:
   (A) incubating a phospholipid membrane under conditions sufficient to permit the formation of ceramide channels through said membrane;
   (B) additionally incubating said phospholipid membrane in the presence of said apoptotic effector compound; and
   (C) measuring said compound's apoptotic effect by determining the affect of said compound on the formation or stability of said ceramide channels, relative to the extent of such formation or stability observed in the absence of said compound.

* * * * *